US007794230B2

(12) United States Patent
Lakin et al.

(10) Patent No.: US 7,794,230 B2
(45) Date of Patent: *Sep. 14, 2010

(54) MATHEMATICAL CIRCULATORY SYSTEM MODEL

(75) Inventors: William D. Lakin, Johnson, VT (US); Scott A. Stevens, Erie, PA (US)

(73) Assignee: University of Vermont and State Agricultural College, Burlington, VT (US)

( * ) Notice: Subject to any disclaimer, the term of this patent is extended or adjusted under 35 U.S.C. 154(b) by 1182 days.

This patent is subject to a terminal disclaimer.

(21) Appl. No.: 11/387,397

(22) Filed: Mar. 23, 2006

(65) Prior Publication Data

US 2006/0166176 A1 Jul. 27, 2006

Related U.S. Application Data

(63) Continuation-in-part of application No. 10/658,638, filed on Sep. 9, 2003, now Pat. No. 7,182,602.

(60) Provisional application No. 60/409,551, filed on Sep. 10, 2002, provisional application No. 60/416,508, filed on Oct. 7, 2002, provisional application No. 60/664,723, filed on Mar. 24, 2005.

(51) Int. Cl.
*G09B 23/28* (2006.01)
*A61B 5/02* (2006.01)

(52) U.S. Cl. .................. 434/270; 434/262; 434/267; 600/481; 600/500

(58) Field of Classification Search ................ 434/236, 434/262, 270; 600/481, 500
See application file for complete search history.

(56) References Cited

U.S. PATENT DOCUMENTS

| 4,003,141 | A | * | 1/1977 | Le Roy ................. 434/270 |
| 4,858,619 | A | * | 8/1989 | Toth ................... 600/561 |
| 5,199,877 | A | * | 4/1993 | Page .................. 434/262 |
| 5,622,170 | A | * | 4/1997 | Schulz ................ 600/424 |
| 5,839,438 | A |   | 11/1998 | Graettinger et al. ...... 128/630 |
| 5,920,395 | A | * | 7/1999 | Schulz ................ 356/622 |
| 5,947,899 | A |   | 9/1999 | Winslow et al. ......... 600/410 |
| 5,987,349 | A | * | 11/1999 | Schulz ................ 600/427 |
| 6,194,899 | B1 | * | 2/2001 | Ishihara et al. ......... 600/412 |
| 6,273,728 | B1 | * | 8/2001 | van Meurs et al. ....... 434/268 |
| 7,191,110 | B1 | * | 3/2007 | Charbel et al. ........... 703/11 |
| 2002/0161304 | A1 | * | 10/2002 | Eide ................... 600/485 |
| 2004/0110117 | A1 |   | 6/2004 | van Oostrom et al. |
| 2009/0069647 | A1 | * | 3/2009 | McNames et al. ........ 600/301 |

(Continued)

OTHER PUBLICATIONS

Stevens et al. Local Compliance Effects on the Global Pressure-Volume Relationship In Models of Intracranial Dynamics. Mathematical and Computer Modeling of Dynamical Systems (2000), vol. 6, No. 4, pp. 445-465.*

(Continued)

*Primary Examiner*—Xuan M Thai
*Assistant Examiner*—Nikolai A Gishnock
(74) *Attorney, Agent, or Firm*—Downs Rachlin Martin PLLC

(57) ABSTRACT

A system and method of modeling a circulatory system including a regulatory mechanism parameter. In one embodiment, a regulatory mechanism parameter in a lumped parameter model is represented as a logistic function. In another embodiment, the circulatory system model includes a compliant vessel, the model having a parameter representing a change in pressure due to contraction of smooth muscles of a wall of the vessel.

39 Claims, 16 Drawing Sheets

U.S. PATENT DOCUMENTS

| | | | |
|---|---|---|---|
| 2009/0292198 A1* | 11/2009 | Kleiven et al. | 600/416 |
| 2010/0049082 A1* | 2/2010 | Hu et al. | 600/561 |
| 2010/0063405 A1* | 3/2010 | Kashif et al. | 600/485 |

OTHER PUBLICATIONS

Stevens, S. Mean Pressures and Flows in the Human Intracranial System, Determined by Mathematical Simulations of a Steady State Infusion Test. Neurological Research, vol. 22, pp. 809-814, (2000).*

Lakin, et al. A Whole-Body Mathematical Model for Intracranial Pressure Dynamics. J. Math. Biol. vol. 46, pp. 347-383 (2003).*

Stevens et al. A Mathematical Model of the Systemic Circulatory System with Logistically Defined Nervous System Regulatory Mechanisms. Mathematical and Computer Modeling of Dynamical Systems, vol. 12, No. 6, Dec. 2006, pp. 555-576.*

Stevens et al. A Differentiable, Periodic Function For Pulsatile Cardiac Output Based on Heart Rate and Stroke Volume. Math. Biosciences, vol. 182, pp. 201-211 (2003), (revised Sep. 18, 2002).*

Stevens et al. Idiopathic Intracranial Hypertension and Transverse Sinus Stenosis: A Modeling Study. Math. Med. and Biol. vol. 24, pp. 85-109 (2007).*

Weisstein, E. W. "Logistic Equation." Retrieved online from MathWorld—A Wolfram Web Resource [Retrieved online Sep. 20, 2009]<URL:http://mathworld.wolfram.com/LogisticEquation.html>.*

International Search Report and Written Opinion dated Jul. 8, 2008, for PCT International Application No. PCT/US2006/010800.

Agarwal GC, Berman BM, and Stark LA: A lumped parameter model of the cerebrospinal fluid system. IEEE Trans Biomed Eng 45-53, Jan. 1969.

Albeck MJ, Gjerris F, Sorenson PS, et al: Intracranial pressure and cerebrospinal fluid outflow conductance in healthy subjects. J. Neurosurgery 74:597-600, 1991.

Chemla D, Herbert JL, Coirault C, Zamani K, Suard I, Colin P, and LeCarpentier Y: Total arterial compliance estimated by stroke volume-to-aortic pulse pressure ratio in humans. Am J Physiol 274 (Heart Circ Physiol 43): 500-505, 1998.

Chopp M and Portnoy HD: Systems analysis of intracranial pressure. J Neurosurgery 53:516-527, 1980.

Czosnyka M, Piechnik S, Koszewski W, Laniewski P, Maksymowicz W, Paluszek K, Smielewski P, Zabolotny W, and Zaworski W: The dynamics of cerebral blood perfusion pressure and CSF circulation—a modelling study. In Avezaat et al. (eds.), Intracranial Pressures VIII. Berlin-Heidelberg, Springer, 699-706, 1993.

Czosnyka M, Piechnik S, Richards S, Kirkpatrick P, Smielewski P, and Pickard JD: Contribution of mathematical modelling to the interpretation of bedside tests of cerebrovascular autoregulation. J Neurol Neurosurg Psychiatry 63:721-731, 1997.

Friden H and Ekstedt J: Volume/Pressure relationships of the cerebrospinal space in humans. Neurosurgery 4:351-366, 1983.

Hakim S, Venegas JG, and Burton JD: The physics of the cranial cavity, hydrocephalus and normal pressure: Mechanical interpretation and mathematical models. Surg Neurol 5:187-210, 1976.

Heldt, Thomas, Shim, Eu Bo, Kamm, Roger D., Mark, Roger G.; *Computational Model of Cardiovascular Function For Analysis of Orthostatic Intolerance.* BED-vol. 50, 2001 Bioengineering Conference; ASME 2001; pp. 895-896.

Hoffmann O: Biomathematics of intracranial CSF and haemodynamics. Simulation and analysis with the aid of a mathematical model. Acta Neurochir Suppl 40:117-130, 1987.

Kadas ZM, Lakin WD, Yu J, and Penar PL: A mathematical model of the intracranial system including autoregulation. Neurological Research 19:441-450, 1997.

Karni Z, Bear J, Sorek S, and Pinczewski Z: A quasi-steady state compartmental model of intracranial fluid dynamics. Med Biol Engng Comput 25:167-172, 1987.

Karni Z, Ivan LP, and Bear J: An outline of continuum modelling of brain tissue mechanics. J Child Neuro 1:119-125, 1986.

Lakin WD and Gross CE: A nonlinear haemodynamic model for the arterial pulsatile component of the intracranial pulse wave. Neurol Res 14:219-225, 1992.

Lakin WD, Yu J, and Penar P: Mathematical modeling of pressure dynamics in the intracranial system. Nova Journal of Mathematics, Game Theory and Algebra 5-2, 1996.

Lakin WD, Yu J, and Penar P: Analysis and validation of a mathematical model for intracranial pressure dynamics. Mathematical and Computer Modelling of Dynamical Systems 3:54-73, 1999.

Lewer AK and Bunt EA: Dysfunction of the fluid mechanical cerebrospinal systems as revealed by stress/strain diagrams. S Afr Mech Eng 28:159-166, 1978.

Miller JD: Volume and pressure in the craniospinal axix. Clin Neurosurg 22:76-105, 1975.

Murgo JP, Westerhof N, Giolma JP, and Altobelli SA: Aortic input impedance in normal man: relationship to pressure wave forms. Circulation 62:105-115, 1980.

Nylin G, Hedlund S, and Regnstrom O: Studies of the cerebral circulation with labeled erythrocytes in healthy man. Circ Res 9:664-674, 1961.

Parazynski SE, Hargens AR, Tucker B, Aratow M, Styf J, and Crenshaw A: Transcapillary fluid shifts in the tissues of the head and neck during and after simulated microgravity. J. Appl. Physiol. 71(6): 2469-2475, 1991.

Rekate HL, Brodkey JA, El-Sakka W, and Ko WH: Ventricular vol. regulation: a mathematical model and computer simulation. Pediat Neurosci 14:77-84, 1988.

Renkin EM, Watson PD, Sloop CH, Joyner WM, and Curry FE: Transport pathways for fluid and large molecules in microvascular endothelium of the dog's paw. Microvasc. Res. 14:205-214, 1977.

Sorek S, Bear J, and Karni Z: A non-steady compartmental flow model of the cerebrovascular system. J Biomechanics 21:695-704, 1988.

Stevens SA: Mean Pressures and Flows of the Human Intracranial System as Determined by Mathematical Simulations of a Steady-State Infusion Test. Neurological Research, 22:809-814, 2000.

Stevens SA, Lakin WD, and Goetz W: A differentiable, periodic function for pulsatile cardiac output based an on heart rate and stroke volume. Mathematical Biosciences, 2003 (to appear).

Stevens SA, and Lakin WD: Local Compliance Effects on the Global CSF Pressure-Volume Relationship in Models of Intracranial Pressure Dynamics. Mathematical and Computer Modelling of Dynamical Systems, vol. 1, No. 1, pp. 000-111, 1996.

Sullivan H, and Allison J: Physiology of cerebrospinal fluid. In: Wilkins R, and Rengachary S, eds. New York: McGraw Hill Book Co. Neurosurgery 3:2125-2135, 1985.

Taylor AE, Granger DN, and Brace RA: Analysis of lymphatic protein flux data. I. Estimation of the reflection coefficient and permeability surface area product for total protein. Microvasc. Res. 13:297-313, 1977.

Thoman, William James—A Computer Model of Intracranial Dynamics, Oct. 30-Nov. 2, 1997, Proceedings—19th International Conference—IEEE/EMBS, pp. 2197-2200.

Ursino, Mauro; *A Mathematical Study of Human Intracranial Hydrodynamics Part 1—The Cerebrospinal Fluid Pulse Pressure*; Annals of Biomedical Engineering, vol. 16, Issue 4, pp. 379-401, 1988.

Ursino, Mauro; *A Mathematical Study of Human Intracranial Hydrodynamics Part 2—Simulation of Clinical Tests*; Annals of Biomedical Engineering, vol. 16, Issue 4, pp. 403-416, 1988.

Ursino, M., Lodi, C.A., Rossi, S. and Stocchetti, N.; *Intracranial Pressure Dynamics in Patients with Acute Brain Damage*; American Physiological Society 0161-7567/97; pp. 1270-1282; 1997.

Ursino, Mauro, Lodi, Carlo Alberto; *A Simple Mathematical Model of the Interaction Between Intracranial Pressure and Cerebral Hemodynamics*; Journal of Applied Physiology 82:, pp. 1256-1269, 1997.

Wang, Eryu—A Model of the Dynamics of Intracranial Pressure During Conditions of Intact and Loss of Cerebral Vascular Tone, 1995 IEEE/EMBC and CMBEC, pp. 1515-1516.

Watenpaugh DE, Breit GA, Ballard RE, Zietz S, and Hargens AR: Vascular compliance in the leg is lower than that in the neck of humans. Medicine and Science in Sports and Exercise (Suppl. 5):S26(137), 1993.

* cited by examiner

MATHEMATICAL CIRCULATORY SYSTEM MODEL

RELATED APPLICATION DATA

This application claims the benefit of U.S. Provisional Patent Application No. 60/664,723, filed Mar. 24, 2005, entitled "Mathematical Circulatory System Model." This application is a continuation-in-part of, U.S. patent application Ser. No. 10/658,638, filed Sep. 9, 2003, now U.S. Pat. No. 7,182,602 entitled "Whole-Body Mathematical Model for Simulating Intracranial Pressure Dynamics," which claims the benefit of U.S. Provisional Patent Application No. 60/409,551, filed Sep. 10, 2002, entitled "A Mathematical Model for Human Intracranial Pressure and Flow Dynamics," and U.S. Provisional Patent Application No. 60/416,508, filed Oct. 7, 2002, entitled "A Mathematical Model for Human Intracranial Pressure and Flow Dynamics." Each of these four prior applications are incorporated herein by reference in their entirety.

GOVERNMENT LICENSE RIGHTS

The U.S. Government may have a paid-up license in this invention and the right in limited circumstances to require the patent owner to license others on reasonable terms as provided for by the terms of Grant No. DMS-96-26391 awarded by the National Science Foundation; and under Grant No. NGT5-40110, Grant No. NNG05GH16H, and Cooperative Agreement No. NCC5-581 awarded by NASA.

FIELD OF THE INVENTION

The present invention relates generally to mathematical circulatory system models and more particularly relates to a mathematical circulatory system model including a regulatory mechanism parameter.

BACKGROUND

Lumped-parameter models represent an attractive method for examining pressure dynamics involving complicated human physiology. In a lumped-parameter modeling approach, the physiological system is subdivided into a number of linked, interacting subunits termed "compartments." In general, each compartment contains a single physical constituent, e.g., blood, cerebrospinalfluid (CSF), or tissue and interstitial fluid. However, depending on the model's complexity, a given constituent may appear in more than one compartment of the model. Dynamics in each compartment is specified by lumped, time-dependent functions giving compartmental pressures, while incremental changes in flows and compartmental volumes are obtained by associating resistance and compliance parameters with adjacent compartments. In particular, interaction between adjacent subunits is assumed to take place at the interfaces of the model's compartments.

With few exceptions, previous models of this type have adopted restrictions known as the "Kellie-Monro Doctrine" to reduce complexity. The Kellie-Monro framework considers the intracranial system to be completely enclosed within the intracranial vault, which is assumed to be rigid. A specified inflow of blood to the intracranial arteries provides a forcing for the system, and outflow from the jugular bulb is assumed to instantaneously equate to this inflow. These restrictions yield a closed system with constant total volume. Strictly intracranial models have produced a number of important results that illuminate the mechanisms of intracranial pressure adjustments in situations involving both normal and pathophysiology. However, the ability of these closed-system models to incorporate the influence of important extracranial factors on intracranial pressure dynamics is clearly limited. For example, the important buffering effects of the spinal CSF space on intracranial pressure cannot be directly included. From a mathematical point of view, the constant volume constraint also produces an over determined system of equations that requires special handling to avoid singular behavior.

Lumped-parameter compartmental models of the present type have a long history, dating to the earliest such model of the intracranial system formulated by Monro in 1783. This first model was bi-compartmental, considering incompressible brain matter and blood as its two constituents. In the work of Monro's student Kellie 40 years later, the vascular compartment was further subdivided into arterial and venous blood to produce a three-compartment model. Since the pioneering work of Monroe and Kellie, increasingly more complex models of the intracranial compartment have been posited in order to more realistically describe the relationship between intracranial pressures and volumes. There has been a steady increase in the number of fluid compartments, the introduction of a separate cerebrospinal fluid compartment, the inclusion of cardiovascular input, and a relaxation of the treatment of system constituents as incompressible fluids and matter. As noted in prior art studies, the intracranial system involves a number of subsystems, which interact through complex mechanisms, and the classical piecewise approach, which often considers CSF dynamics separately, is not suited to studying multiple parameter changes and the effects of interconnected subsystems on each other. By contrast, lumped-parameter models of the intracranial system are capable of including and linking different subsystems, so that such interactions can be examined.

When considering lumped parameter models, it is important to realize that a compartment does not necessarily correspond to a precise physical location in the body. For example, with a single CSF compartment in a model, CSF in the ventricles cannot be distinguished from CSF in the subarachnoid and spinal spaces. This is one of the main limitations of the lumped-parameter approach. Additional spatial resolution can be realized only by subdividing the physical system into a larger number of compartments based on spatial considerations. For example, distinct ventricular CSF and extra-ventricular CSF compartments may be included as opposed to a single lumped CSF compartment. In principle, the entire body could be finely subdivided in this manner into separate compartments to provide the desired degree of spatial resolution. However, clearly this subdivision process cannot be carried to an extreme as the resulting system of linked governing equations will rapidly become too large for practical analysis and solution.

Despite their evolving complexity, two common features characterize most earlier lumped parameter models for pressure dynamics in the intracranial system. The first common feature is an assumption that all resistance and compliance parameters can be represented by constants. This leads to a linear system of governing differential equations. The second common feature is adoption of the "Kellie-Monro Doctrine," which assumes that the intracranial system can be confined within the cranial vault. By requiring that inflow to the intracranial arteries equals outflow from the jugular bulb, this assumption produces a closed system that conserves total intracranial volume.

As mentioned above, when the intracranial space is treated as a closed volume-conserving system contained within the (nearly) rigid cranial vault, important mechanisms for the influence of extracranial physiology on intracranial pressure dynamics cannot be included in the resulting models. For example, the ability of the spinal portion of CSF space to buffer fluctuations of intracranial CSF pressures cannot be directly introduced under the Kellie-Monro Doctrine. At least two prior art mathematical models of intracranial pressure dynamics include aspects of extracranial physiology. The first model includes a compliance for CSF storage within the lumbar channel. The first model contains three compliances, four resistances, and involves differential equations based on a hydrodynamic model for the physical system and its electrical circuit equivalent. The first model allows the dynamic relationship between cerebral perfusion pressure, intracranial pressure, and cerebral blood flow in various states of autoregulation to be studied. Use of the first model in conjunction with clinical data has determined which indices can be derived using transcranial Doppler ultrasonography and which trends of intracranial pressure and blood pressure are useful in clinical tests of autoregulatory reserve. However, despite not strictly abiding by the Kellie-Monro Doctrine, the first model falls far short of being a whole-body model for intracranial pressure dynamics. While the first model can include direct buffering effects of CSF within the lumbar channel, it does not contain other important extracranial physiology. For example, the first model fails to include representations for the extracranial physiology of the cardiovascular system and the tissues and extracellular fluids of both the central and lower body, including cardiovascular autoregulation, colloid osmotic pressure, and a lymphatic system.

The second model uses a single ground compartment to represent the portion of the body below the clavicles. The second model contains three resistances, including a resistance between the intracranial veins and the rest-of-body compartments. Thus, outflow from the intracranial system depends on pressure differences and need not instantaneously equal the specified inflow. The second model also contains three compliances, including a compliance between the CSF and rest-of-body compartment that represents the ability of the spinal portion of CSF space to expand and buffer CSF pressures by compressing the large veins that surround the spinal theca. Two of the three model compliances are pressure dependent. The associated functional forms for the pressure-dependent compliances determined in the second model are used in the present work. The second model still falls short of being a whole-body model for intracranial pressure dynamics. The second model merely lumps extracranial physiology into a single compartment, rather than finely subdividing it into a plurality of compartments. In addition, the second model fails to include the external environment as an implicit compartment.

SUMMARY OF THE INVENTION

In one embodiment, a method of modeling a circulatory system is provided. The method includes (a) providing a circulatory system model including one or more time-dependent pressure functions, each of the one or more time-dependent pressure functions representing a portion of the circulatory system; (b) using a logistic function to represent a regulatory mechanism parameter, the regulatory mechanism parameter representing a regulatory mechanism having an impact on circulatory system function; and (c) solving the logistic function and at least one of the one or more time-dependent pressure functions to determine a circulatory system value.

In another embodiment, a computer readable medium containing computer executable instructions implementing a method of modeling a circulatory system is provided. The instructions include (a) a first set of instructions for providing a circulatory system model including one or more time-dependent pressure functions, each of the one or more time-dependent pressure functions representing a portion of the circulatory system; (b) a second set of instructions for using a logistic function to represent a regulatory mechanism parameter, the regulatory mechanism parameter representing a regulatory mechanism having an impact on circulatory system function; and (c) a third set of instructions for solving the logistic function and at least one of the one or more time-dependent pressure functions to determine a circulatory system value.

In still another embodiment, a method of modeling a pressure and volume relationship in a compliant vessel is provided. The method includes (a) defining a first parameter as a change in pressure within the vessel, the change in pressure being due to a contraction of smooth muscles of a wall of the vessel; and (b) defining a second parameter as an active compliance for the vessel, the active compliance varying with internal pressure, external pressure, and the first parameter.

In yet another embodiment, a computer readable medium containing computer executable instructions implementing a method of modeling a pressure and volume relationship in a compliant vessel is provided. The instructions include (a) a first set of instructions for defining a first parameter as a change in pressure within the vessel, the change in pressure being due to a contraction of smooth muscles of a wall of the vessel; and (b) a second set of instructions for defining a second parameter as an active compliance for the vessel, the active compliance varying with internal pressure, external pressure, and the first parameter.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
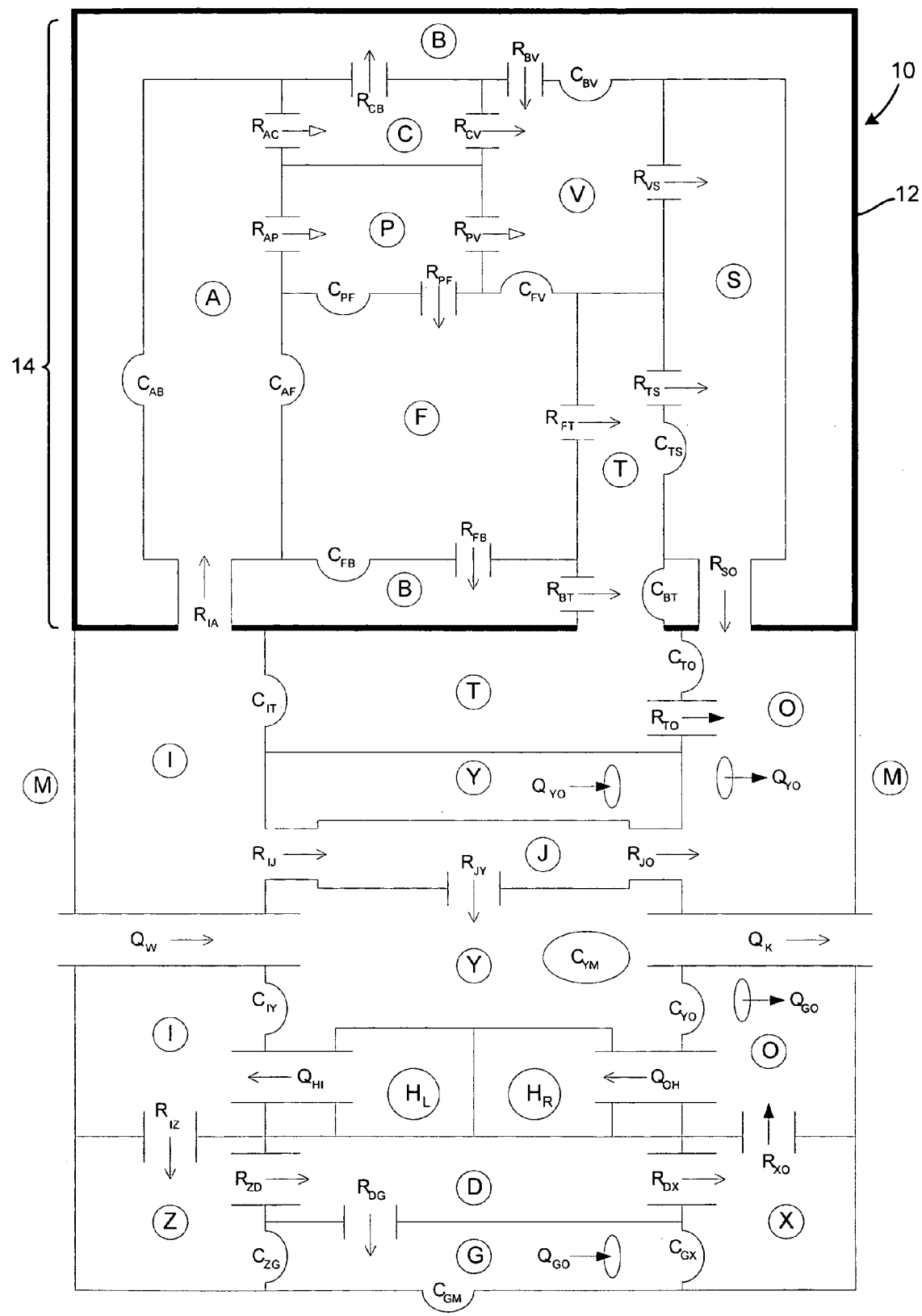
FIG. 1 illustrates one example of a simplified schematic of one embodiment of a multi-compartmental model for determining intracranial pressure dynamics.

The present disclosure is directed to a mathematical circulatory system model. In one aspect, the system and method of the disclosure includes a lumped-parameter model utilizing one or more differential equations representing pressure dynamics. One exemplary embodiment of the present disclosure is set forth in greater detail below with reference to FIGS. 1 to 11. This first embodiment is directed to a whole-body mathematical model for simulating intracranial pressure dynamics. Another exemplary embodiment of the present disclosure is set forth in greater detail below with reference to FIGS. 12 to 21. This second embodiment is directed to a simplified mathematical circulatory system model simulating nervous system regulatory mechanisms.

Whole-Body Embodiment for Simulating Intracranial Pressure Dynamics

In one embodiment a whole-body mathematical model for simulating intracranial pressure dynamics is provided. As described in U.S. Provisional Patent Ser. No. 60/409,551, which is incorporated by reference as if disclosed herein in its entirety, the embodiment revokes the Kellie-Monro Doctrine by consistently embedding the intracranial system within whole-body physiology. In one example of the embodiment, a model includes 17 interacting compartments, of which nine lie entirely outside of the intracranial vault. Two distinct compartments are defined to distinguish ventricular from extraventricular CSF. The vasculature of the intracranial system within the cranial vault is also subdivided into five compartments representing fluid in the intracranial arteries, capillaries, choroid plexus, veins, and venous sinus. The body's extracranial systemic vasculature is divided into six compartments representing the arteries, capillaries, and veins of the central body and the lower body. Tissue and the associated interstitial fluid in the intracranial and lower regions are divided into two compartments. A composite compartment involving the tissues, organs, and pulmonary circulation of the central body and an implicit compartment representing the external environment complete the model. Since the time-dependent compartmental pressure functions are obtained from physical pressures through a "lumping" procedure that involves space-averaging over the physical extent of a compartment, the subdivision of physical constituents into distinct spatially limited compartments is necessary to provide spatial resolution in this modeling approach.

In addition to allowing direct flows (e.g. arteries to capillaries to veins) between adjacent compartments, the disclosure includes the extracranial transfer of fluid between capillaries and tissue by filtration. An extracranial lymphatic system is also included in the model embodiment. Components of the model allow regulation of systemic vascular pressures by the sympathetic nervous system, and, at less than extreme (high or low) pressures, autoregulation mechanisms provide constant blood flow to the cerebrovascular capillaries and the choroid plexus as well as constant production of CSF in the choroid plexus. Fluid intake, renal output of fluid, and adjustment of body volume in response to changes in ambient environmental pressure are allowed. A realistic representation for cardiac uptake and cardiac output provides the forcing for this system.

The form of the present embodiment is a system of governing differential equations for the fully time-dependent compartmental pressure functions. In one aspect, appropriate forms for the non-constant resistance and compliance parameters in the model, which may be functions of both pressures and time, are determined. Calibration of physically realistic scale values for parameters and flows is also a step in the simulation process of this example.

Turning to the drawings, wherein like reference numerals refer to like elements, FIG. 1 illustrates one exemplary embodiment of a mathematical model 10 according to the present invention. In mathematical model 10, the human body is divided into 16 distinct compartments, lettered A, B, C, D, F, G, I, J, O, P, S, T, V, X, Y, and Z. Compartment A represents the intracranial arteries. Compartment B represents the brain. Compartment C represents the intracranial capillaries. Compartment D represents the lower capillaries. Compartment F represents the ventricular CSF. Compartment G represents the lower tissue. Compartment I represents the central arteries. Compartment J represents the central capillaries. Compartment O represents the central veins. Compartment P represents the choroid plexus capillaries. Compartment S represents the venous sinus jugular veins. Compartment T represents the extra-ventricular CSF. Compartment V represents the intracranial veins. Compartment X represents the lower veins. Compartment Y represents the rest of the body. Compartment Z represents the lower arteries. Compartment M represents the external atmosphere. Compartment $H_L$ and $H_R$ represent the left and right heart chambers. The physical constituents in subunits of the present embodiment are blood, CSF, and tissue and interstitial fluid. With a single exception, i.e., compartment Y, each compartment is composed of a single constituent. Spatial resolution is obtained by first dividing the body into intracranial and extracranial components. To help delineate the intracranial system, a thick line 12 in FIG. 1 represents a cranial vault 14, which differentiates intracranial from extra-cranial compartments. Compartments I, Z, Y, J, D, G, O, and X lie completely outside of cranial vault 14, and compartment T includes both intracranial and extracranial physiology.

Figure 2:
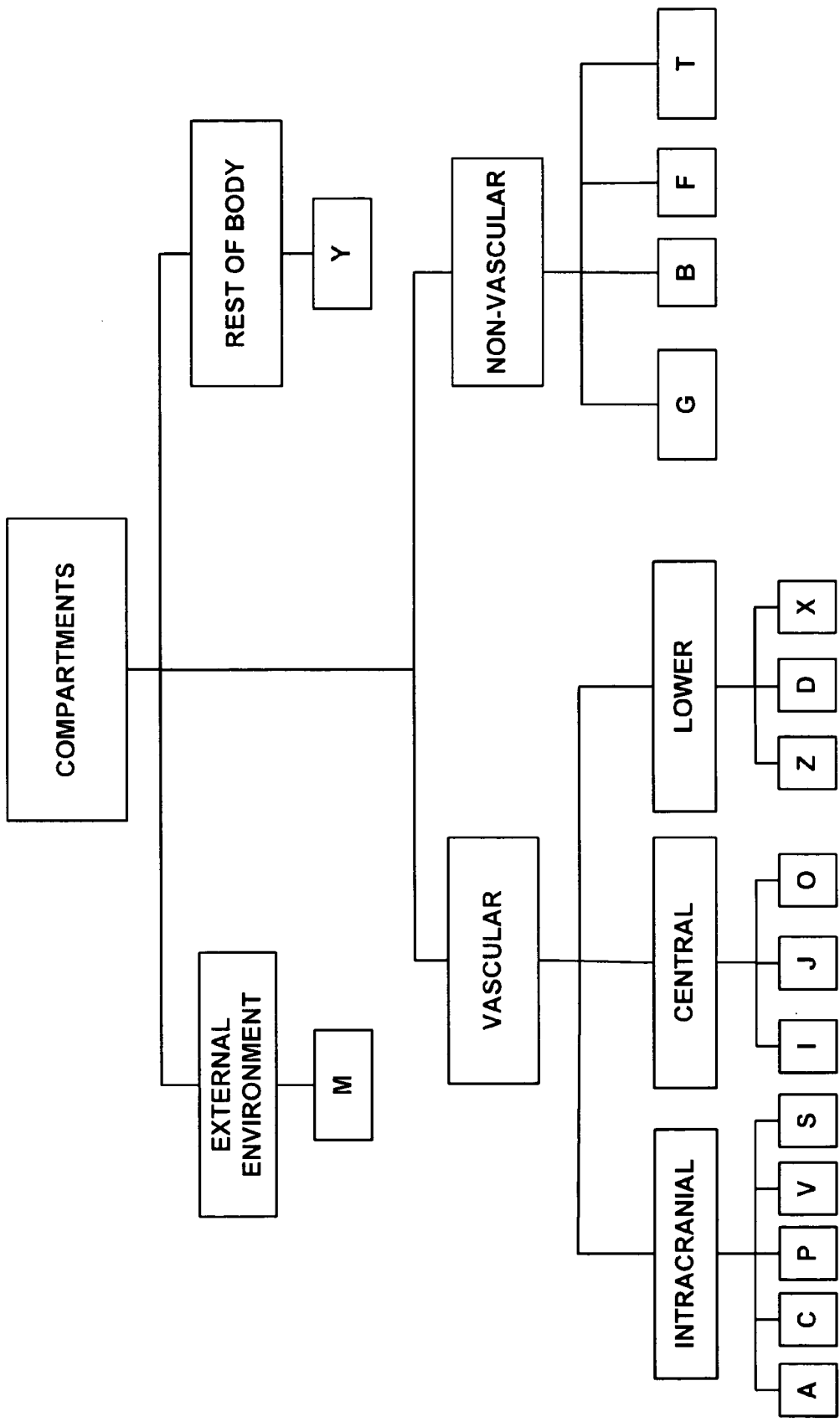
FIG. 2 illustrates one example of a block diagram of the various compartments of a model according to FIG. 1.

As illustrated in FIG. 2, the majority of the compartments in the current embodiment are vascular. The 11 vascular compartments can be subdivided spatially into three groups: intracranial compartments A, C, P, V, and S; central compartments I, J, and O, and lower compartments Z, D, and X. The "lower" compartments represent the region below the pelvis. The "central" compartments in the model represent the region between the lower body and the clavicles and also include extracranial body components above the clavicles but outside of the cranial wall. The vascular system in each of these three regions, i.e., intracranial, central, and lower, is divided into separate artery, capillary, and vein compartments. However, in the intracranial space, the choroid plexus capillaries are placed in a separate compartment P from the rest of the intracranial capillary bed. This allows these capillaries to autoregulate to maintain the production of CSF when ventricular CSF pressures rise or fall. The venus-sinus veins where CSF absorption occurs through the arachnoid villa and the jugular veins are also placed in a compartment separate from the remainder of the intracranial veins, i.e., compartment S. There are four strictly non-vascular model subunits. Two of these compartments represent tissue matter and interstitial fluid, i.e., lower compartment G and brain compartment B, and the other two represent CSF compartments, i.e., ventricular F and extra-ventricular T. Compartment T is both an intracranial and a central compartment. Compartment T, which contains extra-ventricular CSF and lies partially outside of the cranial vault, includes both the subarachnoid and spinal portions of CSF space. Compartment T serves as a bridging compartment and explicitly allows for buffering of CSF pressures by the spinal theca. Two of the three regions contain a separate compartment for the tissue and interstitial fluid. The exception is the central region where the tissue matter, organs (except for the heart), interstitial fluid and pulmonary circulation are lumped into a composite rest-of-body compartment Y. The central region contains an explicit representation for the heart pump having a left chamber pump $H_L$, and a right chamber pump $H_R$, and a realistic pulsatile cardiac output provides the major forcing in the current model. External environment compartment M is also an implicit 17-th subunit in the model. No attempt has been made to depict relative volumes in FIG. 1, and hence the relative sizes of these compartments in the figure do not reflect relative volumes.

The pressure dynamics of the intracranial system are governed by a system of differential equations within mathematical model 10. Four basic assumptions lead to these equations:

(1) all fluids are considered incompressible and isothermal;

(2) pressure driven flows are laminar and related to pressure differences by $$Q_{ij} = \frac{P_i - P_j}{R_{ij}} = Z_{ij}(P_i - P_j) = Z_{ij}P_{ij}, \quad (1)$$

where $Q_{ij}$ is the flow from compartment i into compartment j, $P_i$ and $P_j$ are the spatially-averaged pressures of compartments i and j respectively, $R_{ij}$ is the lumped resistance, $Z_{ij}$ is the fluidity (inverse of $R_{ij}$), the pressure difference $P_{ij}=P_i-P_j$, and $R_{ij}=-R_{ji}$;

(3) in the case of fluid filtration from the capillaries into the interstitial space, the flow is governed by the Starling-Landis Equation, i.e., $$\text{Filtration}=K_{ct}((P_c-P_t)-\sigma_{ct}(\pi_c-\pi_t))=K_{ct}(P_{ct}-\sigma_{ct}\pi_{ct}) \quad (2)$$

where $P_c$ is the capillary pressure, $P_t$ is the interstitial fluid pressure, $\pi_c$ is the blood plasma colloid osmotic pressure, $\pi_t$ is the interstitial fluid colloid osmotic pressure, $K_{ct}$ is the filtration coefficient, and $\sigma_{ct}$ is the capillary membrane reflection coefficient. The notation for pressure difference has been extended to osmotic pressure differences by defining $\pi_{ct}=\pi_c-\pi_t$; and (4) the deformation of the membrane between adjacent compartments is a function of the change in pressure difference between these compartments, i.e., $$\frac{dV_{ij}}{dt} = C_{ij}\frac{d(P_i - P_j)}{dt} = C_{ij}\frac{d(P_{ij})}{dt} \quad (3)$$

where $V_{ij}$ denotes the instantaneous volume of the 'cup' formed in the membrane at the interface of compartments i and j, $C_{ij}$ denotes the compliance between these two compartments, and $C_{ij}=C_{ji}$.

Figure 3:
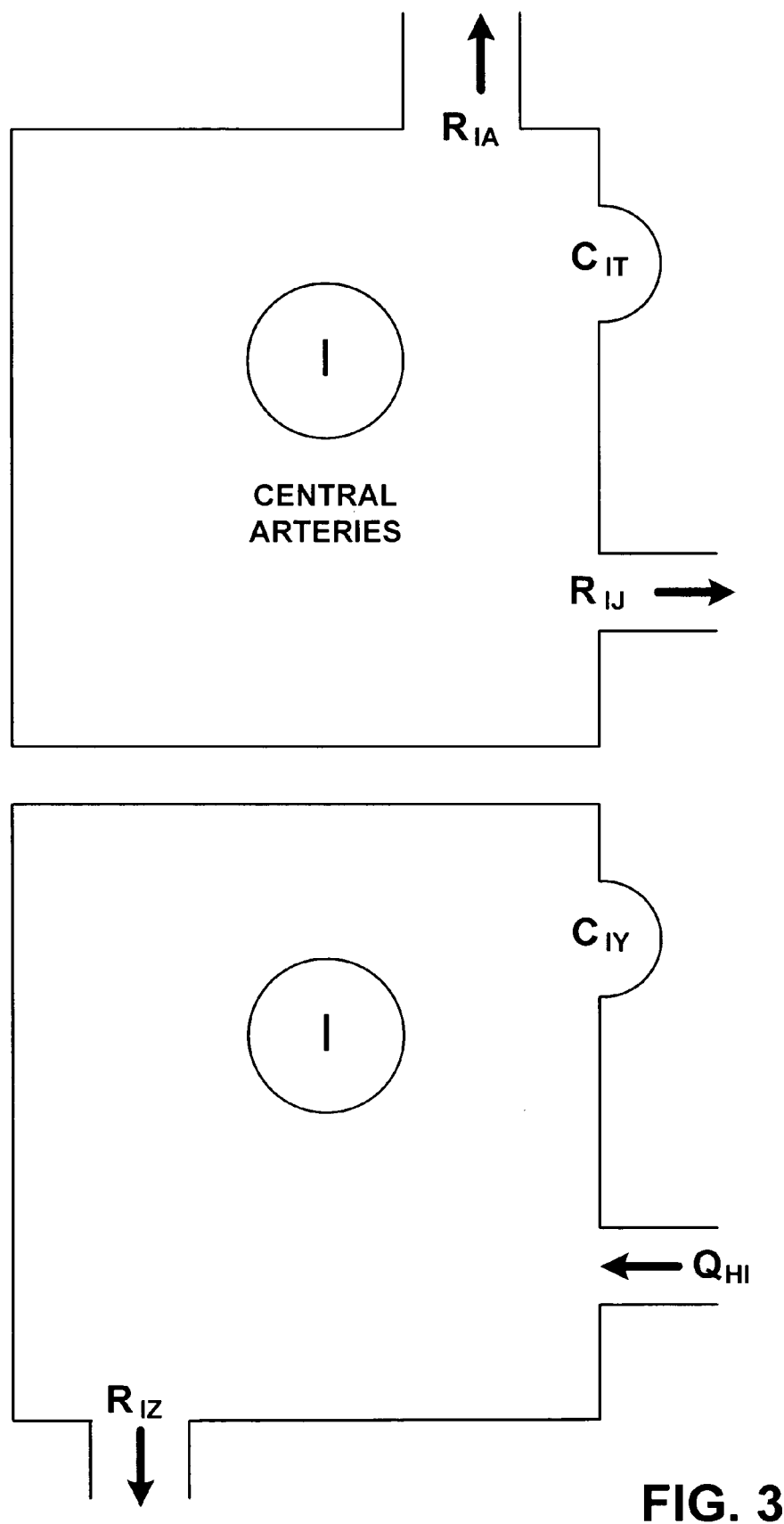
FIG. 3 illustrates one example of an intracranial arteries compartment of the model according to FIG. 1.

As follows, the system of governing equations is obtained by invoking the conservation law $$\text{flow rate in–flow rate out=rate of volume change} \quad (4)$$

in each compartment. Referring now to FIG. 3, compartment I from FIG. 1 is illustrated. Compartment I represents the central arteries. The flow rate into compartment I is represented by $Q_{HI}$ from left heart chamber pump $H_L$. The flow rate out of compartment I is the sum of the flows associated with lumped resistances $R_{IA}$, $R_{IJ}$, and $R_{IZ}$, as represented by equation (1). The rate of volume change of compartment I is equal to the sum of the terms associated with the compliances $C_{IT}$ and $C_{IY}$, as represented by equation (3).

Specifically, the pressure dynamics of compartment I are governed by the following equation:

$$Q_{HI} - (Z_{IJ}P_{IJ} + Z_{IZ}P_{IZ} + Z_{IA}P_{IA}) = C_{IT}\frac{dP_{IT}}{dt} - \frac{dV_{YI}}{dt}. \quad (5)$$

Note that in equation (5), the subscript "IY" has been reversed thereby causing the associated term to be negative. Also, in both FIGS. 1 and 3, a filled arrow indicates a one-way flow and a hollow arrow indicates a pressure dependent resistance. In terms of pressure differences, the relation of equation (4) yields the following additional 12 differential equations and three scalar equations for the remaining 15 body compartments:

Central Capillary Compartment (J):

$$Z_{IJ}P_{IJ}-(K_{JY}(P_{JY}-\sigma_{JY}\pi_{JY})+Z_{JO}P_{JO})=0; \quad (6)$$

Rest of Body Compartment (Y):

$$Q_W + K_{JY}(P_{JY} - \sigma_{JY}\pi_{JY}) - (Q_{YO} + Q_K) = \quad (7)$$

$$C_{YM}\frac{dP_{YM}}{dt} + \frac{dV_{YI}}{dt} + \frac{dV_{YO}}{dt};$$

Central Venous Compartment (O):

$$Z_{JO}P_{JO} + Z_{XO}P_{XO} + Z_{SO}P_{SO} + Z_{TO}P_{TO} + Q_{GO} + Q_{YO} - Q_{OH} = \quad (8)$$
$$C_{TO}\frac{dP_{OT}}{dt} - \frac{dV_{YO}}{dt};$$

Lower Artery Compartment (Z):

$$Z_{IZ}P_{IZ} - Z_{ZD}P_{ZD} = C_{ZG}\frac{dP_{ZG}}{dt}; \quad (9)$$

Lower Capillary Compartment (D):

$$Z_{ZD}P_{ZD} - (Z_{DX}P_{DX} + K_{DG}(P_{DG} - \sigma_{DG}\pi_{DG})) = 0; \quad (10)$$

Lower Tissue Compartment (G):

$$K_{DG}(P_{DG} - \sigma_{DG}\pi_{DG}) - Q_{GO} = \quad (11)$$
$$C_{ZG}\frac{dP_{GZ}}{dt} + C_{GX}\frac{dP_{GX}}{dt} + C_{GM}\frac{dP_{GM}}{dt};$$

Lower Venous Compartment (X):

$$Z_{DX}P_{DX} - Z_{X0}P_{XO} = C_{GX}\frac{dP_{XG}}{dt}; \quad (12)$$

Intracranial Artery Compartment (A):

$$Z_{IA}P_{IA} - (Z_{AC}P_{AC} + Z_{AP}P_{AP}) = C_{AB}\frac{dP_{AB}}{dt} + C_{AF}\frac{dP_{AF}}{dt}; \quad (13)$$

Intracranial Capillary Compartment (C):

$$Z_{AC}P_{AC} - (Z_{CB}P_{CB} + Z_{CV}P_{CV}) = 0; \quad (14)$$

Choroid Plexus Compartment (P):

$$Z_{AP}P_{AP} - (Z_{PF}P_{PF} + Z_{PV}P_{PV}) = C_{PF}\frac{dP_{PF}}{dt}; \quad (15)$$

Intracranial Veins Compartment (V):

$$Z_{CV}P_{CV} + Z_{PV}P_{Pv} + Z_{BV}P_{BV} - Z_{VS}P_{VS} = C_{BV}\frac{dP_{VB}}{dt} + C_{FV}\frac{dP_{VF}}{dt}; \quad (16)$$

Venous Sinus—Jugular Veins Compartment (S):

$$Z_{VS}P_{VS} + Z_{TS}P_{TS} - Z_{SO}P_{SO} = C_{TS}\frac{dP_{ST}}{dt}; \quad (17)$$

Ventricular CSF Compartment (F):

$$Z_{PF}P_{PF} - (Z_{FB}P_{FB} + Z_{FT}P_{FT}) = \quad (18)$$
$$C_{AF}\frac{dP_{FA}}{dt} + C_{PF}\frac{dP_{FP}}{dt} + C_{FB}\frac{dP_{FB}}{dt} + C_{FV}\frac{dP_{FV}}{dt};$$

Extra-Ventricular CSF Compartment (T):

$$Z_{FT}P_{FT} + Z_{BT}P_{BT} - (Z_{TS}P_{TS} + Z_{TO}P_{TO}) = \quad (19)$$
$$C_{TS}\frac{dP_{TS}}{dt} + C_{BT}\frac{dP_{TB}}{dt} + C_{TO}\frac{dP_{TO}}{dt} + C_{IT}\frac{dP_{TI}}{dt}; \text{ and}$$

Brain Compartment (B):

$$Z_{CB}P_{CB} + Z_{FB}P_{FB} - (Z_{BV}P_{BV} + Z_{BT}P_{BT}) = \quad (20)$$
$$C_{AB}\frac{dP_{BA}}{dt} + C_{BV}\frac{dP_{BV}}{dt} + C_{FB}\frac{dP_{BF}}{dt} + C_{BT}\frac{dP_{BT}}{dt}.$$

The terms $dV_{YI}/dt$ and $dV_{YO}/dt$ in the conservation equations for compartments Y, I, and O have been left intact in equations (5), (7), and (8). These volume changes include components that reflect the regulation of arterial pressure by the sympathetic nervous system. They are considered further below. The terms involving $dP_M/dt$ in the conservation equations for 6 compartments Y, and G (equations (7) and (11)) denote a volume change for which there is no compensation through an equal but opposite volume change in an adjacent body compartment. Specifically, these terms reflect volume increases (or decreases) into the ambient environment, which is considered infinitely large and unaffected by pressure changes within the body. Ambient environment compartment M is similar to the ground in an electrical circuit model. It will be maintained at a constant pressure value in exactly the same way that the ground voltage in a circuit model is given a prescribed value relative to which all other values are gauged. Accordingly, the ambient environmental pressure $P_M$ is fixed here at a constant reference value of zero mm Hg. If this is not appropriate for a situation being studied, or if the ambient pressure changes with time, then $P_M$ must be considered as a forcing term in the system of equations.

The set of governing equations may be summed to derive the following constraint regarding compliances between the body and the external environment:

$$(Q_W - Q_K) + (Q_{HI} - Q_{OH}) = C_{YM}\frac{dP_{YM}}{dt} + C_{GM}\frac{dP_{GM}}{dt}. \quad (21)$$

If cardiac output equals cardiac uptake ($Q_{HI} = Q_{OH}$) and the atmospheric pressure is constant, equation (21) simplifies to $$Q_W - Q_K = C_{YM}\frac{dP_Y}{dt} + C_{GM}\frac{dP_G}{dt}. \quad (22)$$

If, in addition, $Q_W = Q_K = 0$ or fluid intake equals fluid discharge ($Q_W = Q_K$), then equation (22) implies as expected that the net volume change of the entire body system must be zero. Furthermore, if $Q_W > Q_K$, as will initially be the case when a glass of water is consumed, the net volume of the body will increase. By equation (22), one of the internal compartmental pressures: $P_G$, or most likely $P_Y$, must now increase. However, if as will be the case, $C_{YM}$ is large, the resultant pressure increase in compartment Y due to the volume input from the ambient environment will be small.

The fluidities in equation (1) must be derived, the filtration and reflection coefficients in equation (2) must be calibrated, and the compliances in equation (3) must be calibrated before model 10's governing differential equations may be used in simulations.

Each constant fluidity $Z_{ij}$ between arbitrary adjacent compartments i and j may be calculated by substituting the mean pressures and the mean flow rates into equation (1) and solving for $Z_{ij}$, giving $$Z_{ij} = \frac{\overline{Q}_{ij}}{\overline{P}_i - \overline{P}_j}. \tag{23}$$

Therefore, once the mean flows and pressures are estimated from physical data, the associated constant fluidities may be calculated from equation (23). Some model fluidities are pressure dependent. A discussion of appropriate expressions for pressure dependent is provided below where CSF, cerebrovascular, sympathetic nervous system, and cardiac autoregulation mechanisms are modeled. However, even for a non-constant fluidity, a mean scale value may still be calculated from equation (23). In the calibrations that follow, mean flows and pressures reflect physiological values for an average human in a lying down (supine) position.

To estimate mean flows, it will be assumed that compartmental volumes remain constant in the mean state. Compartmental pressures are certainly pulsatile, so the system will have a mean state, but not a steady state. However, since volume changes are related to pressure differences between adjacent compartments, if pressures in adjacent compartments move in tandem in the mean state, volumes will remain unchanged. Therefore, for a given compartment, if all but one of the mean flows are known, the final mean flow may be determined from maintaining constant volume. Further, once mean flows into and out of a given compartment are determined, these values provide data for flows in the adjacent compartments. While many flows can be estimated from data available in published literature, most mean flow calibrations must make use of the constant volume assumption.

As a starting point for the calibration of mean flows, consider the percentages of cardiac output $Q_{HI}$ that exit the central arteries into the three peripheral artery systems: A, I, or Z. These percentages, in decimal form, are given below.

$p_{ia}=0.15,=$ % of cardiac output into intracranial region (24)

$p_{iz}=0.25, 0.35,=$ % of cardiac output into lower region (25)

$p_{ij}=1-(p_{ia}+p_{iz}),=$ % of cardiac output into rest of body (26)

Additional helpful percentages and ratios include $p_{pf}=0.70,=$ % of CSF formation from the choroid plexus (27)

$\lambda=250,=\overline{Q}_{AC}/\overline{Q}_{AP}$ (28)

$p_{ts}=0.80,=$ % of CSF drained into venous sinus (29)

Literature values give the following mean flows in ml/min:

$\overline{Q}_{HI}=5000, 6600, 6900,$ Cardiac output (30)

$\overline{Q}_{CF}=2,$ Total capillary filtration (with ⅔ from liver and intestines) (31)

$$\overline{Q}_{JY} = \overline{Q}_{CF}\left(\frac{2}{3} + \frac{1}{3}\frac{p_{ij}}{p_{ij}+p_{iz}}\right), \tag{32}$$

Total capillary filtration into central tissue $$\overline{Q}_{DG} = \frac{1}{3}\frac{p_{iz}}{p_{ij}+p_{iz}}\overline{Q}_{CF}, \text{ Total capillary filtration into lower tissue} \tag{33}$$

$\overline{Q}_F=0.35,$ Total CSF formation (34)

$\overline{Q}_{BV}=0.001,$ Imbalance of diffusion on venule side of cerebrovasculature (35)

$\overline{Q}_{FB}=0.044,$ Flow of CSF through the Virkow-Robins Space (36)

All of the remaining mean flows in the model may now be calibrated based on equations (24) through (36) by invoking the constant volume assumption in each compartment during the mean state. The calibration procedure yields the mean flows:

Central Body Mean Flows $\overline{Q}_{OH}=\overline{Q}_{HI}$ from cardiac output=cardiac input (37)

$\overline{Q}_{IA}=p_{ia}\overline{Q}_{HI}$ from equation (24) (38)

$\overline{Q}_{IZ}=p_{iz}\overline{Q}_{HI}$ from equation (25) (39)

$\overline{Q}_{IJ}=\overline{Q}_{HI}-(\overline{Q}_{IA}+\overline{Q}_{IZ})$ from constant volume in I (40)

$\overline{Q}_{JO}=\overline{Q}_{IJ}-\overline{Q}_{JY}$ from constant volume in J (41)

$\overline{Q}_{YO}=\overline{Q}_{JY}$ from constant volume in Y (42)

Lower Body Mean Flows $\overline{Q}_{ZD}=\overline{Q}_{IZ}$ from constant volume in Z (43)

$\overline{Q}_{GO}=\overline{Q}_{DG}$ from constant volume in G (44)

$\overline{Q}_{DX}=\overline{Q}_{ZD}-\overline{Q}_{DG}$ from constant volume in D (45)

$\overline{Q}_{XO}=\overline{Q}_{DX}$ from constant volume in X (46)

Intracranial Mean Flows $\overline{Q}_{AP}=\overline{Q}_{IA}/(\lambda+1)$ from constant volume in A and equation (28) (47)

$\overline{Q}_{AC}=\lambda\overline{Q}_{AP}$ from equation (28) (48)

$\overline{Q}_{PF}=p_{pf}\overline{Q}_F$ from equation (27) (49)

$\overline{Q}_{CB}=(1-p_{pf})\overline{Q}_F+\overline{Q}_{BV}$ from $\overline{Q}_{CB}-\overline{Q}_{BV}=(1-p_{pf})\overline{Q}_F$ (50)

$\overline{Q}_{CV}=\overline{Q}_{AC}-\overline{Q}_{CB}$ from constant volume in C (51)

$\overline{Q}_{PV}=\overline{Q}_{AP}-\overline{Q}_{PF}$ from constant volume in P (52)

$\overline{Q}_{VS}=\overline{Q}_{CV}+\overline{Q}_{PV}+\overline{Q}_{BV}$ from constant volume in V (53)

$\overline{Q}_{BT}=\overline{Q}_{CB}+\overline{Q}_{FB}-\overline{Q}_{BV}$ from constant volume in B (54)

$\overline{Q}_{FT}=\overline{Q}_{PF}-\overline{Q}_{FB}$ from constant volume in F (55)

$\overline{Q}_{TS}=p_{ts}\overline{Q}_F$ from equation (29) (56)

$\overline{Q}_{TO}=(1-P_{ts})\overline{Q}_F$ from constant volume in T (57)

$\overline{Q}_{SO}=\overline{Q}_{VS}+\overline{Q}_{TS}$ from constant volume in S (58)

Equation (49) states that 70% of the CSF formation comes from the choroid plexus and equation (50) states that the remaining CSF formation comes as a filtrate from the 10 capillaries through the brain via the Virchow-Robins system minus the amount reabsorbed at the venule side of the capillaries ($Q_{BV}$). Notice that, as should be the case, $\overline{Q}_{BT} + \overline{Q}_{FT} = \overline{Q}_F$.

In addition to allowing direct flows (e.g. arteries to capillaries to veins) between adjacent compartments, the present embodiment includes the transfer of fluid between capillaries and tissue by filtration. These flows are governed by the Starling-Landis equation and are driven by differences between the colloid osmotic pressures of the blood plasma in the capillaries and the interstitial fluid as well as by the usual compartmental pressure differences between capillaries and tissue. Filtration mechanisms are included between the capillaries and tissue compartments in the central and lower portions of the body in the present embodiment. In the intracranial region, significant colloid osmotic pressure differences do occur between the intracranial capillary and tissues. However, the endothelial cells that make up the intracranial capillary wall are so tightly joined that not even water molecules can usually pass between them. Thus, under normal conditions, colloid osmotic pressure forces in the intracranial region are irrelevant. In the case of highly elevated capillary pressure it is possible for the intracranial capillary wall to expand enough to allow water molecules to pass between the endothelial cells, and at this point both colloid osmotic pressures and regular pressures start governing filtration rates. At these elevated pressures, the description of intracranial capillary filtration as a function of capillary pressure will clearly be nonlinear. However, to simplify the equation for intracranial filtration, this relationship may still be linearly approximated with the slope defined by $Z_{CB}$, $Z_{BV}$, and $Z_{FB}$.

There are two locations in the embodiment where fluid flow is governed by the Starling-Landis equation (2). These flows in the central and lower body are $$Q_{JY} = K_{JY}((P_J - P_Y) - \sigma_{JY}(\pi_J - \pi_Y)) \text{ and} \quad (59)$$

$$Q_{DG} = K_{DG}((P_D - P_G) - \sigma_{DG}(\pi_D - \pi_G)), \quad (60)$$

denoting the flow from the capillaries into the tissue subunits of the central and lower body regions, respectively. Solving these relations for the filtration coefficients in the mean state implies $$K_{JY} = \frac{\overline{Q}_{JY}}{((\overline{P}_J - \overline{P}_Y) - \sigma_{JY}(\overline{\pi}_J - \overline{\pi}_Y))} \quad (61)$$

$$K_{DG} = \frac{\overline{Q}_{DG}}{((\overline{P}_D - \overline{P}_G) - \sigma_{DG}(\overline{\pi}_D - \overline{\pi}_G))} \quad (62)$$

The mean flows on the right hand side of these equations have been calculated above. Thus, to determine the filtration coefficients $K_{JY}$ and $K_{DG}$, it is only necessary to calibrate scale values for the mean colloid osmotic pressures and the reflection coefficients.

Mean interstitial fluid colloid osmotic pressure is given by $$\overline{\pi}_Y = \overline{\pi}_G = 8 \text{ mm Hg} \quad (63)$$

and blood plasma colloid osmotic pressure by $$\overline{\pi}_J = \overline{\pi}_D = 28 \text{ mmHg}. \quad (64)$$

Notice that these values are invariant with respect to central or lower regions. This is not the case, however, with the reflection coefficients $\sigma_{JY}$ and $\sigma_{DG}$. The reflection coefficient 11 in the legs is estimated to be approximately 0.9 while the coefficient of the upper body is less than this value. This is reflected by the assignments $$\sigma_{JY} = 0.8 \quad (65)$$

$$\sigma_{DG} = 0.9 \quad (66)$$

The filtration coefficients $K_{JY}$ and $K_{DG}$ in equations (61) and (62) are now readily determined.

Calibration of scale values for all resistance and compliance parameters from available physical data and other relationships must be accomplished before the model's governing differential equations can be used in simulations. A key step in calibrating model compliances is determining the distensibilities of the extracranial compartments of the model. In particular, each extracranial compartment has an associated total compliance equal to the product of its associated volume and distensibility. It should be noted that calculating compliances by this technique yields a total central artery compliance $C_f = 1.529$ ml/mm Hg, which is within 5 percent of the data value of 1.445 ml/mm Hg for total arterial compliance measured in the ascending aorta by Chemla et al. The central venous compliance calculated by these methods yields $C_V = 50$ ml/mm Hg while known systemic venous pressure volume curves suggests a total venous compliance of 50 ml/mm Hg. Finally, Noordergraaf states that the systemic arterial compliance is between 1 and 2 ml/mm Hg and systemic venous is between 50 and 200 ml/mm Hg.

In this section, the various compliances in equation (3) that relate volume adjustments to pressure differences will be calculated. In the intracranial region, compartmental volume increases are restricted by the rigid cranial wall. Consequently, compartmental compliances must be pressure dependent and diminish to zero as pressure differences become large. On the other hand, in extracranial regions, to lowest order compliances may consistently be considered constant, approximating a linear relationship between pressure differences and volume adjustments. The present intracranial pressure-dependent compliances are extensions of those derived in the prior art, while the constant extra-cranial compliances will be derived from estimations of the volume and distensibility of each compartment.

In a simplified four-compartment whole-body model for CSF dynamics described in the prior art, there are only two pressure difference dependent compliances. They allow volume adjustments between the CSF and arterial blood and between the CSF and venous blood. These compliances have the general form described by the relation $$C_{ij}^4(P_{ij}) = C_{ij}^o e^{-r_{ij}|P_{ij}|^{a_{ij}}}, \quad (67)$$

where $P_{ij} = P_i - P_j$, and the subscripts i and j take the values $C_{af}^4$ (for arterial/CSF compliance) and $C_{fv}^4$ (for CSF/venous compliance). For both pairs of index values, Coefficients and parameters in equation (67) are given by $$C_{fv}^O = 6.5333, \ r_{fv} = 0.633431 \ a_{fv} = 0.604229 \quad (68)$$

$$C_{af}^O = 1.82745, \ r_{af} = 0.817102 \ a_{af} = 0.869393 \quad (69)$$

This four-compartment model contains an additional constant compliance between the CSF and the rest of the body (g), which is approximated as $$C_{fg}^4 = 0.13333. \quad (70)$$

This feature represents the interface of extra-cranial CSF in the spinal theca with the rest of the body. It also acts as a background compliance so that the total CSF compliance can never reach machine zero in simulations.

In the present 16 compartment model, the division of the body's cerebrospinalfluid (CSF) space is considerably more refined. Hence, the three CSF compliances in the simple four compartment model of the prior art must be appropriately apportioned among the compliances of the present embodiment. Three decimal percentages may be introduced to describe this allocation of $C_{fv}^4$:

$$p_{fv}=0.164 \text{ percentage of } C_{fv}^4 \text{ allocated to } C_{FV} \quad (71)$$

$$p_{to}=0.214 \text{ percentage of } C_{fv}^4 \text{ allocated to } C_{TO} \quad (72)$$

$$p_{ts}=0.622 \text{ percentage of } C_{fv}^4 \text{ allocated to } C_{TS} \quad (73)$$

Equations (71-73) reflect the fact that total CSF volume is approximately 140 ml, 23 of which is found in the ventricles, 30 in the spinal cord subarachnoid space (theca) and the remainder in the cerebral cisterns and subarachnoid space. Thus, if the distensibility of the membrane is similar in these three different components of CSF, then $C_{fv}$ is 23/140=0.164 of $C_{fv}^4$ as indicated by $p_{fv}$ in equation (71). This same technique yields the values in equations (72) and (73). The compliance $C_{PF}$ is excluded in this division of $C_{fv}^4$ as the choroid plexus capillaries are known to dilate and constrict in order to maintain a constant pressure difference between these capillaries and ventricular CSF. This maintains a constant generation rate of CSF from the choroid plexus at normal pressure values. Consequently, a value for the compliance $C_{PF}$ is irrelevant in the absence of a pressure difference change.

The ratios that lead to equations (71)-(73) also imply the following percentages describing the allocation of $C_{af}^4$:

$$p_{af}=0.786 \text{ percentage of } C_{af}^4 \text{ allocated to } C_{AF} \quad (74)$$

$$p_{it}=0.214 \text{ percentage of } C_{af}^4 \text{ allocated to } C_{IT} \quad (75)$$

The background compliance $C_{fg}^4$ is now divided between venous and arterial interfaces based on systemic venous volume being four times that of arterial volume, giving $$C_{venous}=0.8 C_{fg}^4 \quad (76)$$

$$C_{arterial}=0.2 C_{fg}^4 \quad (77)$$

The CSF-related compliances may now be calculated based on the above percentages as:

$$C_{FV}(P_{FV})=0.95 p_{fv}(C_{fv}^4(P_{FV})+C_{venous})\overline{C}_{FV}=0.557868 \text{ ml/mm Hg}$$

$$C_{FB}(P_{FB})=0.05 p_{fv}(C_{fv}^4(P_{FB})+C_{venous})\overline{C}_{FB}=0.036255 \text{ ml/mm Hg}$$

$$C_{TS}(P_{TS})=0.95 p_{ts}(C_{fv}^4(P_{TS})+C_{venous})\overline{C}_{TS}=1.27626 \text{ ml/mm Hg}$$

$$C_{BT}(P_{BT})=0.05 p_{ts}(C_{fv}^4(P_{BT})+C_{venous})\overline{C}_{BT}=0.137057 \text{ ml/mm Hg}$$

$$C_{TO}(P_{TO})=p_{to}(C_{fv}^4(P_{TO})+C_{venous})\overline{C}_{TO}=0.200936 \text{ ml/mm Hg}$$

$$C_{AF}(P_{AF})=p_{af}(C_{af}^4(P_{AF})+C_{arterial})\overline{C}_{AF}=0.0261999 \text{ ml/mm Hg}$$

$$C_{IT}(P_{IT})=p_{it}(C_{af}^4(P_{IT})+C_{arterial})\overline{C}_{IT}=0.00571427 \text{ ml/mm Hg}$$

where again, the pressure difference $P_i-P_j$ is denoted $P_{ij}$ and the scale value $\overline{C}_{ij}=C_{ij}(\overline{P}_i-\overline{P}_j)=C_{ij}(\overline{P}_{ij})$. The compliance $C_{BT}$, introduced to incorporate volume adjustments between the brain and subarachnoid CSF, is allocated 5% of $C_{TS}$. This states that of the bulk intracranial compliance in compartment T, 95% is allocated to the interface with the highly distensible venous sinus veins and only 5% to the interface with the less distensible brain tissue. A similar allocation is made for the bulk intracranial compliance of the ventricular CSF compartment F with respect to the intracranial veins and the brain tissue.

Finally, brain/vascular compliances $C_{AB}(P_{AB})$ and $C_{BV}(P_{BV})$ are defined to similar CSF/vascular compliances as:

$$C_{AB}(P_{AB})=C_{AF}(P_{AB})\overline{C}_{AB}=0.0209523 \text{ ml/mm Hg}$$

$$C_{BV}(P_{BV})=C_{FV}(P_{BV})\overline{C}_{BV}=0.688845 \text{ ml/mm Hg}.$$

When calculating extra-cranial compliances it is advantageous to first determine the total compliance of each compartment. This quantity will be denoted by $C_i$ with the subscript indicating the compartment. This type of compliance can be described by the relation $$\text{Total Compartmental Compliance} = \frac{\text{Increase in Compartmental Volume}}{\text{Increase in Compartmental Pressure}} \quad (78)$$

and may be experimentally determined by measuring the pressure change that is induced by an estimated volume change and then taking the inverse of this ratio. Unfortunately, clinical data does not exist for determination of all of the compliances required for the current embodiment. However, there is information in the literature regarding volumes and distensibilities. These are related to compliance by $$\text{Compliance} = \text{Distensibility} \cdot \text{Volume}. \quad (79)$$

Therefore, total compartmental compliance may be calculated from total compartmental volume (denoted $V_i$) and compartmental distensibility (denoted $D_i$) through equation (79). However, before calculating compartmental volumes and distensibilities it is useful to describe how the resulting total compartmental compliances will be allocated to the local inter-compartmental compliances.

Estimations of the local compliances are made by requiring that the sum of the relevant local compliances must equal the total compliance being apportioned. With this restriction, the embodiment's predicted compartmental pressure changes induced by known volume changes should agree with experimental data. Based on this principle, the apportionment of total compliances among local compliances is described by Central, Local Compliances:

$$C_{IY}=\text{Max}[C_I-\overline{C}_{IT},0] \text{ ml/mm Hg} \quad (80)$$

$$C_{YO}=\text{Max}[C_O-\overline{C}_{TO},0] \text{ ml/mm Hg} \quad (81)$$

$$C_{YM}=\text{Max}[C_Y-(C_{IY}+C_{YO}),0] \text{ ml/mm Hg} \quad (82)$$

Lower, Local Compliances:

$$C_{ZG}=C_Z \text{ ml/mm Hg} \quad (83)$$

$$C_{GX}=C_X \text{ ml/mm Hg} \quad (84)$$

$$C_{GM}=\text{Max}[C_G-(C_{ZG}+C_{GX}),0] \text{ ml/mm Hg} \quad (85)$$

Here, the Max[,] function is used to ensure that no negative compliances occur in the embodiment. For the particular choices of total compliances here, this function is not needed, but it is included above as it may be required if total tissue compliances are calculated to be much smaller.

Total blood volume ($V_{blood}$) is estimated at 5000 ml and 5600 ml, where blood plasma makes up about 60% of this. The relative volumes of systemic veins, arteries and capillaries are:

$$V_{sa}=0.16 V_{blood} \text{ systemic artery volume} \tag{86}$$

$$V_{sv}=0.64 V_{blood} \text{ systemic vein volume} \tag{87}$$

$$V_{sc}=0.04 V_{blood} \text{ systemic capillary volume} \tag{88}$$

$$V_{pulm}=0.09 V_{blood} \text{ pulmonary system volume} \tag{89}$$

$$V_{heart}=0.07 V_{blood} \text{ heart-blood volume} \tag{90}$$

These values are based on estimates that the systemic arteries comprise 13% of the blood volume while the systemic arterioles and capillaries comprise 7%. In the present embodiment, arteriole volume is lumped with the arteries, and hence 3% of the arteriole/capillary space is shifted here into the artery compartment resulting in the percentages above. It should also be noted that these percentages imply that systemic venous volume is four times that of systemic artery volume.

As a next step, arterial and venous volumes must be allocated between the intracranial, lower, and central compartments. Estimates for this distribution are given below. It should be emphasized that these are percentages of the systemic blood and exclude the blood volumes in the heart and pulmonary system.

$$pV_{cran}=0.07 \text{ percentage of systemic blood, intracranial region} \tag{91}$$

$$pV_{lower}=0.40 \text{ percentage of systemic blood, lower region} \tag{92}$$

$$pV_{central}=0.53 \text{ percentage of systemic blood, central region} \tag{93}$$

The above percentages lead to the following volumes for the extra-cranial, vascular compartments:

$$V_Z=pV_{lower}V_{sa}=\text{lower artery volume} \tag{94}$$

$$V_I=pV_{central}V_{sa}=\text{central artery volume} \tag{95}$$

$$V_X=pV_{lower}V_{sv}=\text{lower vein volume} \tag{96}$$

$$V_O=pV_{central}V_{sv}=\text{central vein volume} \tag{97}$$

$$V_D=pV_{lower}V_{sc}=\text{lower capillary volume} \tag{98}$$

$$V_J=pV_{central}V_{sc}=\text{central capillary volume.} \tag{99}$$

The volumes of the tissue and rest of body compartments are now calculated based on interstitial fluid volume and intracellular fluid volume. Total interstitial fluid volume is estimated in the prior art to be 12 L, while total intracellular fluid volume is estimated to be 28 L. Considering that approximately 2 L of the intracellular fluid is contained in the blood cells, the following volume assignments can be made:

$$V_{inter}=12000 \text{ ml}=\text{interstitial fluid volume} \tag{100}$$

$$V_{intra}=26000 \text{ ml}=\text{intracellular fluid volume} \tag{101}$$

With these volume assignments and the percentages in equations (92)-(93), estimates for lower tissue and rest-of-body volumes become:

$$V_G=pV_{lower}(V_{inter}+V_{intra})=\text{lower tissue volume} \tag{102}$$

$$V_Y=pV_{central}(V_{inter}+V_{intra})+V_{pulm}=\text{rest of body volume} \tag{103}$$

Estimations for the pressure-strain modulus are given by Milnor and Nichols and O'Rourke for various branches of the systemic arteries. From this data, the distensibility of the various vessels can be calculated. Of interest here are the calculated distensibilities for the ascending aorta and the femoral artery, represented in the model by $D_I$ and $D_Z$. Milnor's data suggests that $D_I$ is 0.0036225 mmHg$^{-1}$ and $D_Z$ is 0.00101 mmHg$^{-1}$ while Nichols and O'Rourke data suggests $D_I$ is 0.00320141 mmHg$^{-1}$ and $D_Z$ is 0.00237912 mmHg$^{-1}$. Averaging these values results in the assignments $$D_I=0.00341196 \tag{104}$$

$$D_Z=0.00169456. \tag{105}$$

Since it is known that the central veins are eight times as distensible as central arteries, $D_O$ is calculated accordingly by $$D_O=8D_I. \tag{106}$$

There are some suggestions in the prior art that the upper venous distensibility may be larger that of the lower leg, but these results are inconclusive. Therefore, lower venous distensibility is set to $$D_X=D_O. \tag{107}$$

Consistent with prior art findings, the capillary compartments C, J, and D are considered non-deformable.

The distensibility of the lower tissue compartment is assigned a weighted average of the interfacing vein and artery distensibilities. Since the veins have four times the volume of the arteries, these weights are used in $$D_G = \frac{D_Z + 4D_X}{5} = 0.0221754 \text{ (ml/mm Hg)/ml} \tag{108}$$

Finally, the distensibility of the rest-of-body compartment (Y) is also a weighted average based on its composition:

$$D_Y = \frac{pV_{central}(V_{inter}+V_{intra})D_G + \left(\frac{4}{5}V_{pulm}\right)D_O + \left(\frac{1}{5}V_{pulm}\right)D_I}{V_Y} \tag{109}$$

$$= 0.0221838 \text{ (ml/mm Hg)/ml}$$

The distensibilities of the extra-cranial compartments have now been determined. Combined with the volumes of the previous section, each extra-cranial compartment now has an associated total compliance equal to the product of its associated volume and distensibility.

A lymphatic system is also included in the present embodiment. This system allows interstitial fluid in the tissue compartments of the central and lower regions of the body to flow directly into the central venous compartment. Lymphatic flows are thus able to balance filtration in these regions and establish an equilibrium state. Lymphatic flow is not introduced in the intracranial region as the brain appears to lack lymphatic vessels. However, drainage of interstitial fluid via the Virchow-Robins Spaces is accommodated by pathways between the Brain and CSF compartments.

The lymphatic system is represented in the present embodiment through the flows $Q_{YO}$ and $Q_{GO}$. These flows provide pathways through which interstitial fluid can move directly from the interstitium to the central venous system. Unlike the flows between adjacent compartments, which are driven by pressure differences, the lymphatic flow is governed almost exclusively by the interstitial fluid pressure. This flow increases 20 fold at interstitial fluid pressures near 4 mm Hg from the corresponding flow at an interstitial pressure of about −6 mm Hg. Below this interstitial fluid pressure value, lymphatic flow ceases. The relative lymphatic curve is modeled by the logistic expression $$P_{lymph}(x) = \frac{M}{1+(M-1)e^{-r(x+6)}}, \text{ where } M = 20 \text{ and } r = 1 \quad (110)$$

Figure 4:
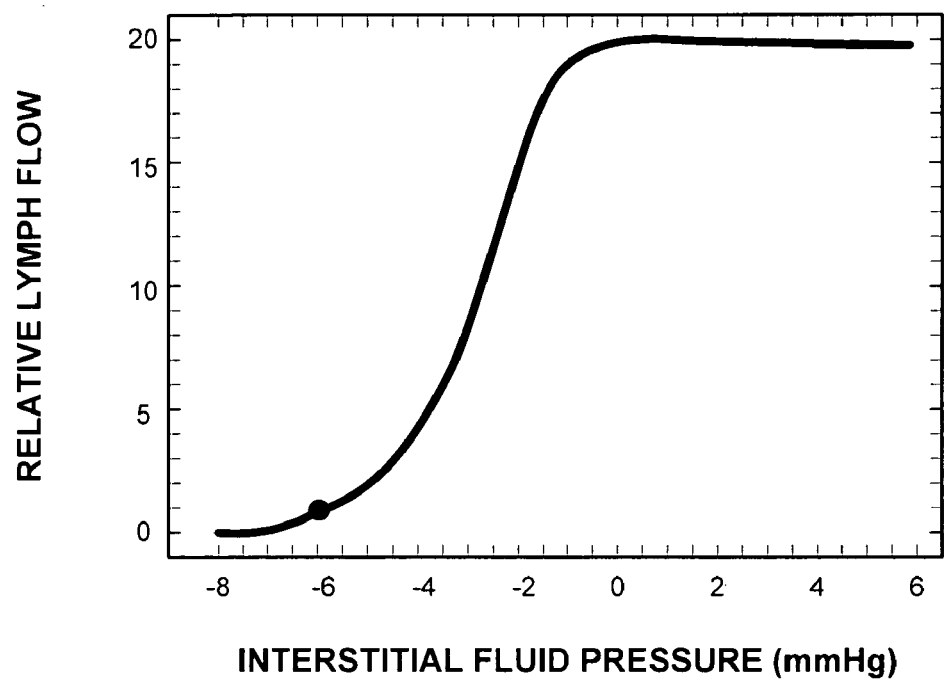
FIG. 4 illustrates one example of a chart of interstitial fluid pressure vs. relative lymph flow.
Figure 5:
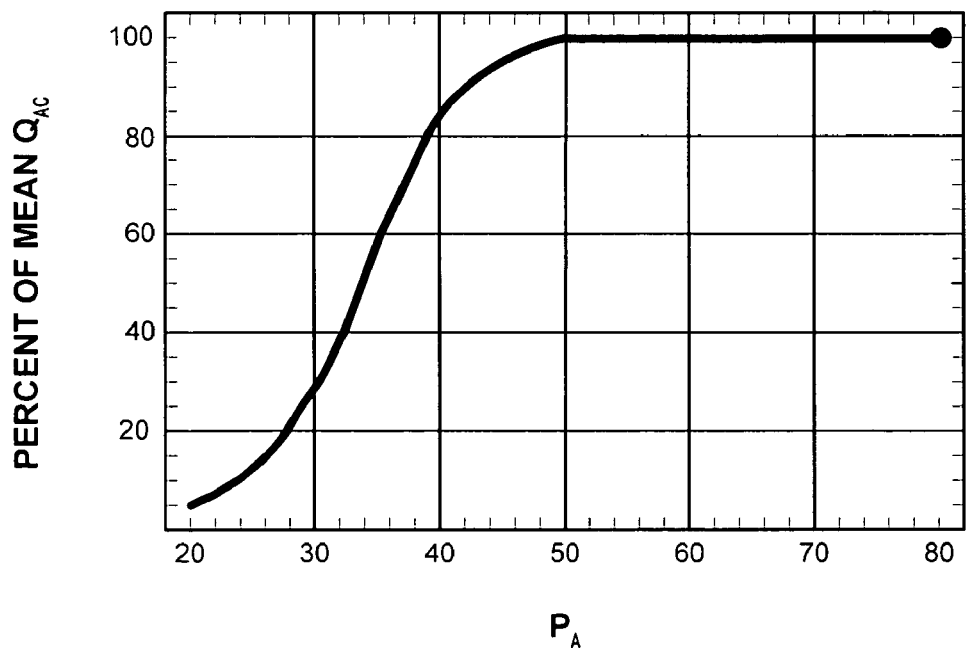
FIG. 5 illustrates one example of a chart of percent reduction in $Q_{AC}$ VS. $P_A$.

This function, depicted in FIG. 4, defines the relative lymph flow in terms of interstitial pressure. The large dot in FIG. 4 denotes the mean pressure of interstitial fluid in the model. Conversion of this relationship to the actual lymphatic flows $Q_{GO}$ and $Q_{YO}$ is accomplished by defining $$Q_{GO}(t) = \frac{P_{lymph}(P_G)\overline{Q}_{GO}}{P_{lymph}(\overline{P}_G)}, \quad (111)$$

$$Q_{YO}(t) = \frac{P_{lymph}(P_Y)\overline{Q}_{YO}}{P_{lymph}(\overline{P}_Y)}. \quad (112)$$

In this manner, the mean flow is maintained at the mean pressure and can increase or decrease accordingly. Based on equation (110), $Q_{GO}$ can increase from a mean flow of about 0.24 ml/min to about 4.7 ml/min while $Q_{YO}$ can increase from about 1.76 ml/min to about 35 ml/min.

Blood supply and CSF production is well regulated in the human intracranial system. This auto-regulation is achieved by the dilation and constriction of the blood vessels induced by factors such as carbon dioxide concentration, hydrogen ion concentration, oxygen concentration and intracranial pressures. This embodiment incorporates such auto-regulation in the form of pressure sensitive fluidities depicting either vessel constriction in the form of a reduced fluidity or dilation in form of increased fluidity.

In all, the present embodiment contains 16 compliance parameters, of which eight are variable and depend on pressure differences. There are also 23 resistance parameters. Four intracranial resistances are pressure-dependent and autoregulate flow to both the cerebral capillary bed and the choroid plexus as well as the production of CSF in the choroid plexus. CSF production is known to be nearly constant over a wide range of pressures. However, the production of CSF decreases when perfusion pressure decreases to low values, and a mechanism that ramps down CSF production when perfusion pressure falls below about 55 mm Hg is also included in the model.

Blood flow into the cerebral capillaries is auto-regulated by a pressure dependent fluidity $Z_{AC}$ defined by $$Z_{AC} = \frac{F(P_A)}{P_A - P_C} \quad (113)$$

where $F(P_A)$ is a logistic expression defined by $$F(P_A) = \overline{Q}_{AC}\frac{M}{1+(M-1)e^{r(\overline{P}_A - P_A)}} \text{ with } M = 1.00001 \text{ and } r = 0.25. \quad (114)$$

This implies that $Q_{AC} = Z_{AC}(P_A - P_C) = F(P_A)$ and cerebral blood flow is thus determined almost entirely by intracranial artery pressure and does not diminish significantly until this pressure drops below 50 mm Hg. The relationship between $Q_{AC}$ and $P_A$ is displayed in FIG. 5.

Blood flow into the choroid plexus is regulated by a pressure-difference dependent fluidity $Z_{AP}$ defined by $$Z_{AP} = \frac{\overline{Q}_{AP}}{(P_A - P_P)} \cdot G(P_{perf}) \quad (115)$$

where the multiplier $G(P_{perf})$ in equation (115) is a function of the perfusion pressure $P_{perf} = P_A - P_B$ that is unity when $P_{perf}$ exceeds about 55 mm Hg and then falls linearly to zero below this value. This implies that $$Q_{AP} = Z_{AP} \cdot (P_A - P_P) = \overline{Q}_{AP} \cdot G(P_{perf}). \quad (116)$$

The multiplier G has been included in equation (115) to model the fact that CSF production in the choroid plexus scales with blood flow, remains nearly constant over a wide range of pressures, and is decreased as a function of the magnitude of the perfusion pressure when $P_{perf}$ falls below about 50 mm Hg to about 60 mm Hg. From equation (116), blood flow into the choroid plexus remains constant unless perfusion pressure falls to a low level.

Over the wide range of normal pressures, the production of CSF is auto-regulated at the venous side of the choroid plexus capillaries by the pressure dependent fluidity $Z_{PV}$ defined by $$Z_{PV} = \frac{\overline{Q}_{AP} \cdot G(P_{perf}) - Z_{PF} \cdot (P_P - P_F)}{P_P - P_V}. \quad (117)$$

When $P_{perf} \geq 55$, this expression for $Z_{PV}$ will maintain a constant pressure difference between the choroid plexus and the ventricular CSF. Substituting $Z_{PV}$ with G=1 into the governing equation for the choroid plexus, equation (15) reduces to $$C_{PF}\frac{dP_{PF}}{dt} = 0. \quad (118)$$

Since the compliance $C_{PF}$ must be non-zero to account for the known ability of the Choroid Plexus to transmit pressure pulsations to the ventricular CSF, the governing equation for the choroid plexus compartment becomes simply $$\frac{dP_{PF}}{dt} = 0. \quad (119)$$

This implies a constant pressure difference between the choroid plexus and ventricular CSF is maintained by equation (117) for $P_{perf} \geq 55$ mm Hg. Therefore, $$Q_{PF} = Z_{PF} \cdot (P_P - P_F) = Z_{PF}(\overline{P}_P - \overline{P}_F) = \overline{Q}_{PF}. \quad (120)$$

Since for pressures in the normal range, CSF production in the choroid plexus is proportional to $P_{PF}$, constant CSF production from the choroid plexus is thus achieved. Equation (119) also eliminates the need to estimate $C_{PF}$ in this model as occurrences of this parameter are always multiplied by either $dP_{PF}/dt$ or $dP_{FF}/dt$.

Using the above results, it can now be demonstrated how $Z_{PV}$ autoregulates CSF production for $P_{perf} \geq 55$ mm Hg. Substituting $\bar{Q}_{PF}$ for $Z_{PF}\cdot(P_P-P_F)$ in equation (117) and noting that $\bar{Q}_{AP}-\bar{Q}_{PF}=\bar{Q}_{PV}$ results in the equalities:

$$Z_{PV} = \frac{\bar{Q}_{PV}}{P_P - P_V} \quad (121)$$

$$= \frac{\bar{Q}_{PV}}{(P_P - P_F) + (P_F - P_V)}$$

$$= \frac{\bar{Q}_{PV}}{\bar{Q}_{PF}/Z_{PF} + (P_F - P_V)}.$$

The last term in this expression reveals the relationship between $Z_{PV}$ and $P_F$. Physiologically, $Z_{PV}$ should decrease with increasing CSF pressure ($P_F$) causing an increase in choroid plexus pressure and maintaining constant CSF production across $Z_{PF}$. It is quite clear from the last equality in equation (121) that this is indeed the case. These autoregulatory mechanisms may be substituted into (13) to (16) and (18) to obtain the governing equations for compartments A, C, P, V, and F.

The present embodiment also includes a group of regulatory mechanisms associated with the sympathetic nervous system (SNS). Two variable resistances in the central and lower regions provide for SNS regulation of arterial pressure through constriction of the arterioles. Included in these variable resistances is the dramatic "last ditch stand" triggered by the SNS when arterial pressure falls to a level where cerebral blood flow is affected. The far less extreme SNS regulation of arterial pressure through a constriction of the large vascular vessels in the central body is also represented in the model. Active interfaces are placed between the central rest-of-body compartment and the central artery and vein compartments. When arterial pressure falls, forcing terms in the governing equations for compartments Y, I, and O force the volume cups at the active Y-I and Y-O interfaces into the vascular compartments, providing the regulatory constriction. An additional SNS mechanism in the model regulates central arterial pressure by increasing the number of heartbeats per minute if arterial pressure falls.

The sympathetic nervous system (SNS) is associated with reflex mechanisms that act to maintain levels of arterial pressure and cardiac output if arterial pressure falls. This section deals with the portions of the model that represent the capacity of the SNS to rapidly increase arterial pressure by constricting both the arterioles and the large vascular vessels. An embodiment of the regulation of cardiac output by the SNS will be developed below.

A first SNS pressure mechanism involves constriction of the large vessels of the circulation in the central body. If arterial pressure falls, the large vessels of the circulation in the central body, especially the veins, strongly constrict to cause a rapid increase in arterial pressure. This mechanism is included in the current model by placing active interfaces between the central compartment Y and the central vascular compartments I and O. Forcing terms in the conservation equation for compartment Y now force the volume cups at the interfaces to push into the I and O compartments when arterial pressure diminishes, modeling the SNS large vessel constriction mechanism.

The conservation equation in compartment Y is described by $$\frac{dV_Y}{dt} = \frac{dV_{YO}}{dt} + \frac{dV_{YI}}{dt} + \frac{dV_{YM}}{dt} = Q_{JY} - Q_{YO} \quad (122)$$

where the second equality determines the equation. Here, the volume change $dV_{YM}/dt$ between compartment Y and the external environment M, as in equation (3), is simply proportional to the change in pressure difference $dP_{YM}/dt$. However, $dV_{YO}/dt$ and $dV_{YI}/dt$ involve both changes in the pressure differences $dP_{YO}/dt$ and $dP_{YI}/dt$, respectively, and a forcing term describing the active compliance between Y and O and between Y and I, respectively. In particular, $$\frac{dV_{YO}}{dt} = C_{YO}\frac{dP_{YO}}{dt} + F_{YO}(t) \text{ with } F_{YO}(t) = -24P'_I \text{ and} \quad (123)$$

$$\frac{dV_{YI}}{dt} = C_{YI}\frac{dP_{YI}}{dt} + F_{YI}(t) \text{ with } F_{YI}(t) = -8P'_I \quad (124)$$

The governing differential equation in compartment Y is now obtained by replacing $dV_{YO}/dt$ and $dV_{YI}/dt$ in equation (7) by the expressions (123) and (124). Similarly, for the governing equations in compartments O and I, $dV_{YO}/dt$ is replaced in equation (8) by expression (123) and $dV_{YI}/dt$ is replaced in equation (5) by expression (124), respectively.

A second SNS pressure regulation mechanism involves constriction of the arterioles in most parts of the body (excluding the brain and heart) when central artery pressure drops. This causes an increase in arterial pressure through an increase in the total peripheral resistance. When the arterial pressure drop is severe enough to compromise blood flow to the brain, this regulatory response is extreme.

To model this portion of the SNS regulatory response, two multipliers are defined for the artery-capillary fluidities $Z_{IJ}$ and $Z_{ZD}$. These variable resistances are of the form $$Z_{IJ} = \frac{\bar{Q}_{IJ}}{P_I - P_J} \cdot SNSz_1(P_I) \cdot SNSz(Q_{AC}). \quad (125)$$

and $$Z_{ZD} = \frac{\bar{Q}_{ZD}}{P_Z - P_D} \cdot SNSz_1(P_I) \cdot SNSz(Q_{AC}). \quad (126)$$

The first multiplier, $$SNSz_1(P_I) = \frac{P_I}{\bar{P}_I}, \quad (127)$$

is a function of central body artery pressure that increases resistance if $P_I$ falls below its mean level. The second multiplier, which is a function of the cerebral blood flow $Q_{AC}$, is defined by $$SNSz(Q_{AC}) = \frac{M}{1 + (M-1)e^{r(\bar{Q}_{AC}-Q_{AC})}} \text{ where } M = 1.1 \text{ and} \quad (128)$$

$r = 0.02$.

This multiplier models the last-ditch stand when cerebral blood flow is significantly reduced. SNSz remains close to unity (not activated) until arterial pressure drops to a level where $Q_{AC}$ is affected. At this point, SNSz drops sharply, dramatically increasing the resistances $R_{IJ}$ and $R_{ZD}$.

The major source of forcing in the present whole-body embodiment comes from the heart and involves the cardiac output $Q_{HI}$ and cardiac uptake $Q_{OH}$. Because it is known that all extra blood that flows into the heart is automatically pumped without delay into the aorta and flows again through the circulation, the cardiac output will be set equal to cardiac uptake, so that $Q_{HI}=Q_{OH}$. It is further known that the normal heart, functioning without any special stimulation, can pump an amount of venous return up to 2.5 times the normal venous return before the heart becomes the limiting factor. Therefore, a venous return function R is defined that incorporates all of the flow into the central venous compartment $$R=Q_{YO}+Q_{GO}+Z_{JO}(P_J-P_O)+Z_{TO}(P_T-P_O)+Z_{SO}(P_S-P_O)+Z_{XO}(P_X-P_O). \tag{129}$$

The cardiac uptake $Q_{OH}$ is now defined in terms of this venous return and two regulatory multipliers SNSo and OVP by $$Q_{OH}=SNSo(P'_I)\cdot OVP(P_O)\cdot R \tag{130}$$

where $P'_I$ denotes the time derivative of the arterial pressure function $P_I$. Since $Q_{HI}=Q_{OH}$, cardiac output is now based on the venous return through equation (130).

The multiplier SNSo in equation (130) is associated with cardiac regulation by the sympathetic nervous system (SNS). It models an SNS mechanism that increases or decreases the heart rate in response to a change in arterial pressure. A decrease in arterial pressure can markedly increase heart activity, with the heart rate increasing to as high as 160-180 bpm from the normal value of 72 bpm. A linear model for the SNSo multiplier as a function of the instantaneous time derivative $P'_I$ is $$SNSo(P'_I) = 1 - \frac{P'_I}{10}. \tag{131}$$

This relationship produces an increase in heart rate to about twice the normal level as the result of a pressure drop of about 20 mm Hg. Note that SNSo (O)=1, so that this regulatory mechanism is only active when $P_I$ is changing.

The OVP function in equation (130) insures that if venous pressure drops, then so does cardiac uptake. It is defined by $$OVP(P_O) = \frac{M}{1+(M-1)e^{r(P_O-P_O)}} \tag{132}$$

where $M = 2.5$ and $r = 0.5$.

Since OVP($\overline{P}_O$)=1, this regulatory mechanism is not active when central venous pressure remains at its mean value.

Using the above cardiac forcing terms leads to a system of equations that describe mean pressures in the sense that the oscillations that occur about a mean pressure value are removed and the mean pressure may be considered a temporal average over one cardiac cycle. However, when trying to resolve circulatory pressure pulsations caused by cardiac output, a more instantaneous description of cardiac output is necessary. Again in this case, cardiac output is set equal to cardiac uptake.

Figure 6:
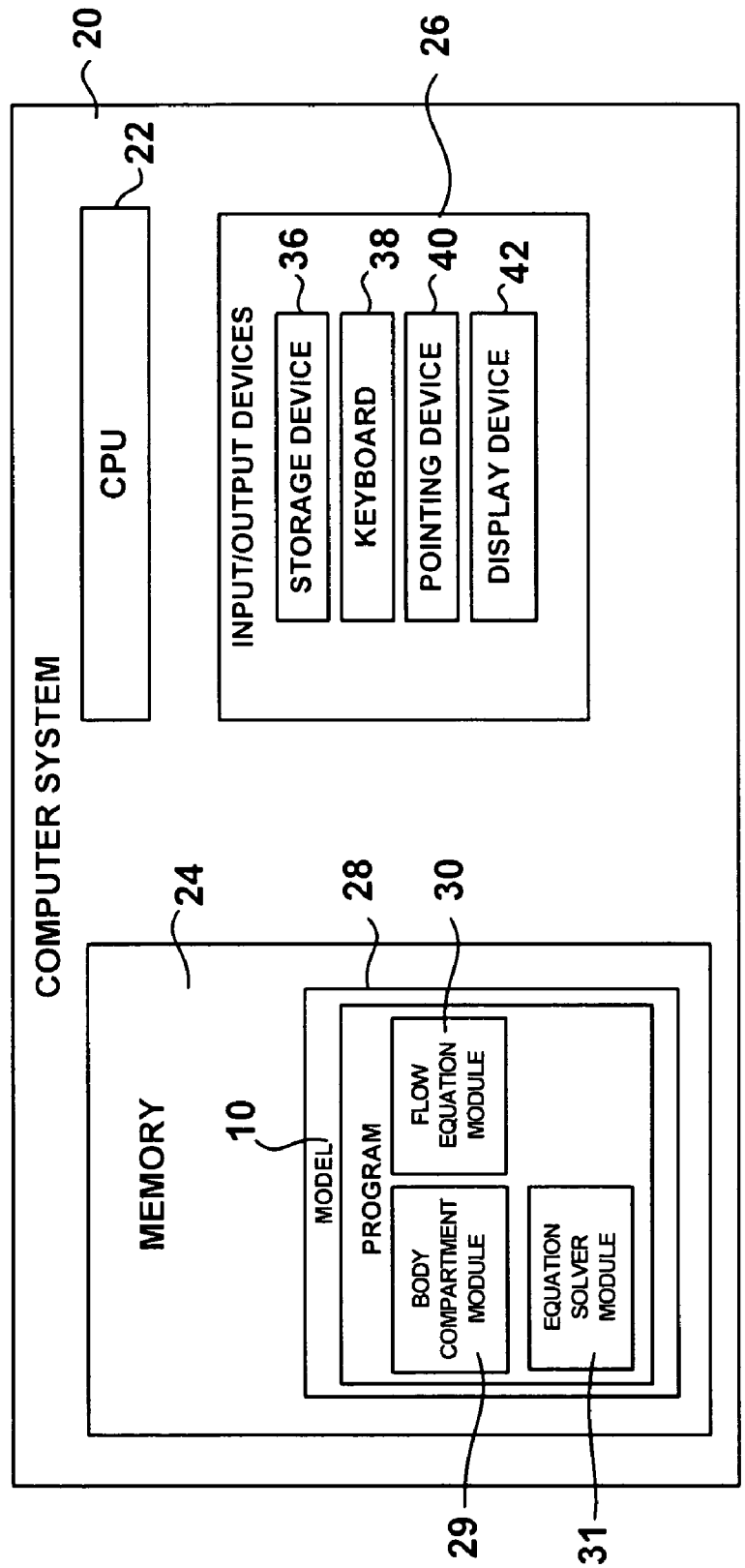
FIG. 6 illustrates one example of a simplified schematic of a computer system including one embodiment of the present invention.

Referring now to FIG. 6, it is contemplated that mathematical model 10 of FIG. 1 may operate in a computing environment including a computer system 20. Computer system 20 includes a computer central processing unit (CPU) 22, a computer memory 24, and input/output devices 26. Mathematical model 10 is typically implemented with or embodied in a computer program 28 which, when executed by computing resources within computer system 20, provide the functionality of the present invention. Typically, computer program 28 resides in computer memory 24 of an individual client computer system. Of course, computer program 28 may reside in the memory of a local or wide area network server or in the memory of an equipment computer processor. In one embodiment, computer programs 28 include a body compartment module 29, a flow equation module 30, and an equation solver module 31. Body compartment module 29 includes instructions for dividing the body into a plurality of compartments and a heart pump, each compartment representing a portion of the body. Flow equation module 30 includes instructions for deriving a plurality of differential flow equations, each of which correspond to one of the compartments. Equation solver module 31 includes instructions for solving the plurality of differential flow equations. The instructions within body compartment module 29, flow equation module 30, and equation solver module 31 are executed within computer programs 28 to simulate the pressure dynamics of the intracranial system. Input/output devices 26 typically include a storage device 36, such as a hard disk drive, a keyboard 38, a pointing device 40, i.e., a mouse, and a display device 42, such as a monitor. It is contemplated that data may be manually input to mathematical model 10 via input/output devices 26 or automatically input via patient monitoring equipment or the like.

Figure 7A:
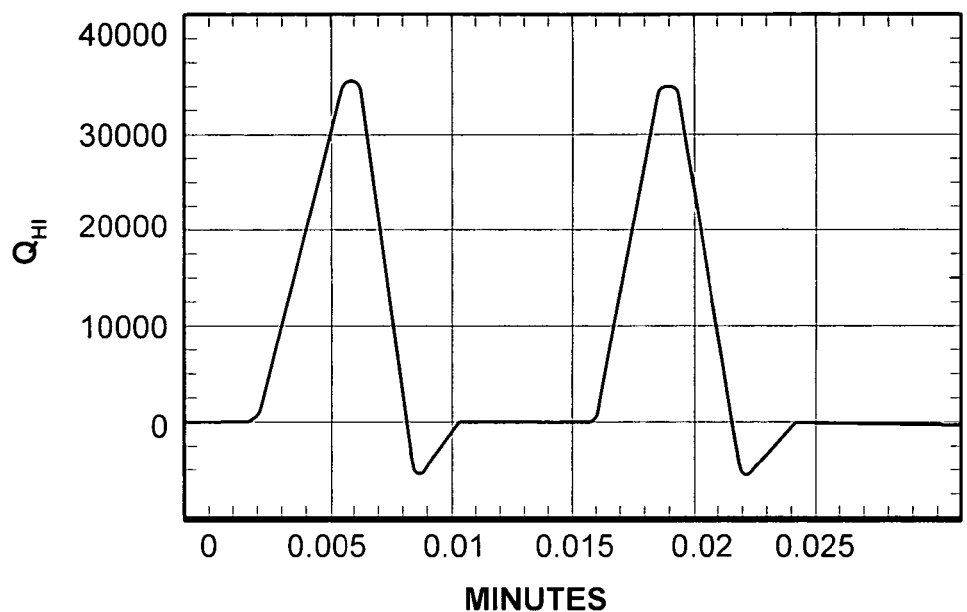
FIG. 7A illustrates one example of a chart of pulsatile cardiac forcing ($Q_{HI}$) over time.

To validate the present whole-body model embodiment for intracranial pressure dynamics, several types of simulations assuming normal physiology were carried out and the results compared to clinical observations. In the first type of simulation, a pulsatile form for cardiac output was introduced as forcing so that the model's predicted pressure responses could be compared to clinically measured pressure pulsations in healthy humans. The pulsatile cardiac output function with parameter values n=11, $\phi$=0.27882, and $\sigma$=5.958 was used as the cardiac forcing function ($Q_{HI}$) in the model's governing equations. This function is depicted in FIG. 7A and represents the cardiac output over two cycles. A mean value for central artery pressure of 96 mm Hg was prescribed as an initial condition for the first simulation. In the second type of simulation, a constant flow infusion test was used to validate the model's representations for variable intracranial compliances and intracranial fluid dynamics. In these simulations, the governing equation for the extra-ventricular CSF compartment (T) was augmented by adding a constant infusion term to model the clinical infusion of mock CSF into the lower lumbar space.

With the lower body region explicitly represented by separate compartments in the present embodiment, the effect of orthostatic forces on cerebral blood flow as the body changes position can be considered. Two additional types of simulations were now run to validate the modeling of the regulatory mechanisms associated with the systemic nervous system. The normal physiology value for the resistance $R_{XO}$ was increased twofold and $R_{IZ}$ was decreased by one half to simulate a change in body position from lying down to standing up, and the behavior of the cerebral blood flow $Q_{AC}$ was then examined. These resistance changes were made instantaneously and the modeled effect on cerebral blood flow was determined for the next 30 seconds. In the first simulation of this type, the model equations included all of the SNS reflexes described above. In the second simulation, the SNS terms were removed from the governing equations.

To examine the potential predictive capabilities of the embodiment in pathological conditions, simulations were run where all cardiac forcing in the model was suddenly stopped to simulate cardiac arrest, i.e., $Q_{HI}$ and $Q_{OH}$ were suddenly set equal to zero. A blood volume of about 5600 ml was assumed in these simulations, and the response of pressures in the embodiment's circulatory compartments was determined. This behavior, and the predicted final circulatory compartmental pressure values, were then compared to clinical results associated with cardiac arrest and the filling pressure of the circulation.

As a second example of pathology, simulations of hemorrhagic shock were carried out. Hemorrhage was modeled by the inclusion of an outflow path, denoted $Q_{XM}$, from lower venous compartment X into ambient atmosphere compartment M. This flow was calculated so as to achieve an about 45% loss in blood volume at the end of the simulation. The percent changes in central artery pressure, cardiac output, and cerebral blood flow were then calculated with respect to percent blood loss.

In all of these simulations, the model's system of differential equations was solved numerically using a typical symbolic mathematical software package employing maximum accuracy settings.

Figure 7B:
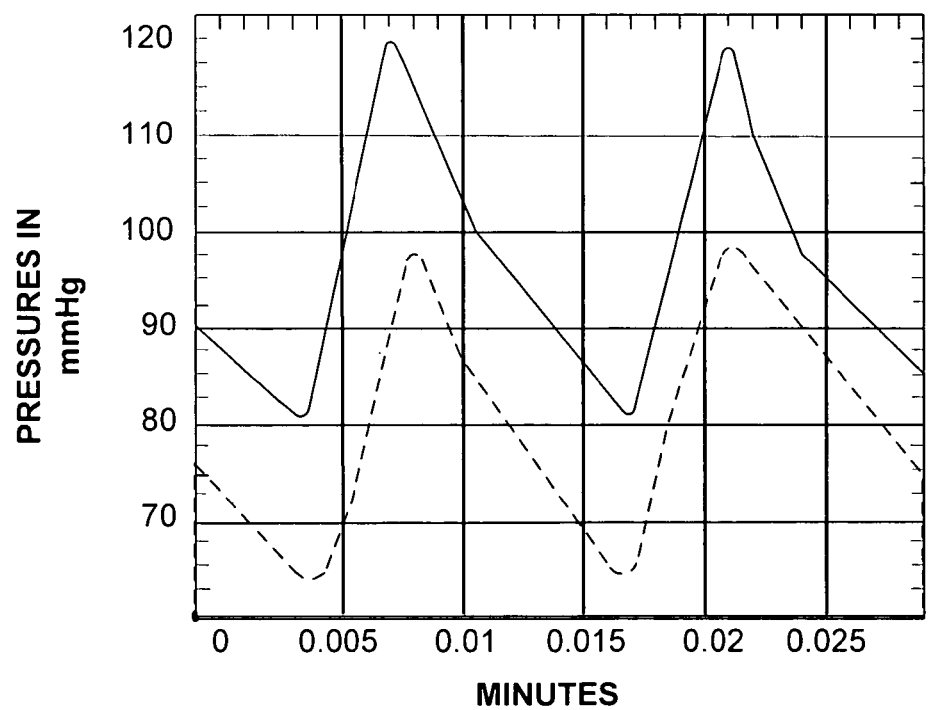
FIG. 7B illustrates one example of a chart of the 120/80 central artery pressure response over time (solid) and the 100/65 intracranial artery pressure response (dashed)

The usual systolic and diastolic values of pulsatile central artery pressure are perhaps the best-known values in human physiology. FIG. 7B shows the behavior of central artery pressure predicted by the present embodiment in response to the pulsatile cardiac forcing developed in the prior art. The embodiment's predicted response to a mean value of 96 mm Hg, prescribed as an initial condition, reproduces a peak systolic pressure of about 120 mm Hg and a diastolic pressure of about 80 mm Hg. FIG. 7B also depicts the intracranial artery pressure response. Here, the predicted systolic and diastolic pressures are "100 over 65." These values are typical of those in the small arteries.

Because even the most complex mathematical model must be based on assumptions and simplifications of actual physiology, model validation is an essential step in the development process. In the present case, after calibration of parameters associated with healthy human physiology, the model was used in two types of simulations and the results compared to physical data. In the first type of simulation, the response of compartmental pressures to the realistic pulsatile cardiac output given in FIG. 7A was determined. As shown in FIG. 7B the predicted response of central arterial pressure is the typical "120 over 80" blood pressure readings expected in healthy humans. It is worth noting that a mild incisura (dicrotic notch) is discernable in this pressure curve. This notch is typical in central artery pressure readings, although is it usually more pronounced than in FIG. 7B. In particular, the present embodiment cannot capture reflected waves which have a tendency to cause a second (usually higher) systolic peak and hence a more prominent inflection point.

The response of the intracranial arteries is also shown in FIG. 7B. This response agrees well with prior art estimates for pressure pulses in the small arteries. The pressure responses of other intracranial compartments were also within expected ranges.

Constant flow infusion tests were also simulated using the present embodiment. In these experiments, mock CSF was infused at a constant rate into the lower lumbar space. The pressure of this space was then measured and associated with a calculated total CSF volume change. This resulted in determination of a curve known as the global pressure-volume relation. The slope of this curve describes the elastance of the entire CSF space, including extracranial portions. The inverse of the elastance is the more well-know compliance.

The typical clinical global CSF pressure-volume relation, except at extreme pressures, is an S-shaped curve of logistic type. It has a lower pressure plateau near resting pressure, defined as the pressure where CSF production in the system is just balanced by CSF absorption by the venous system. This region of small slope (large compliance) is due to the ability of the system to easily accommodate increases in the volume of the CSF space at these relatively low pressures through the compression of the venous system (excluding the venus-sinus veins). As additional CSF volume is added to the system and pressures increase, this capacity for adjustment diminishes as there will be less venous blood available to eject to further compress the veins. Thus, with increasing pressures, the pressure-volume curve steepens indicating a reduction in the compliance of the system. The slope of the pressure-volume relationship continues to increase for larger infusion volumes until the resulting CSF pressures are high enough that the intracranial arteries can begin to be compressed. At this point, some additional compliance enters the system. There is a point of inflection in the curve followed by a region of decreasing slope that leads to an upper pressure plateau at the diastolic pressure of the intracranial arteries. Once additional volume increases beyond this point increase CSF pressures to the systolic pressure of the intracranial arteries, there are no additional mechanisms available to buffer additional volume increases, and the compliance of the CSF system falls to zero.

Figure 8A:
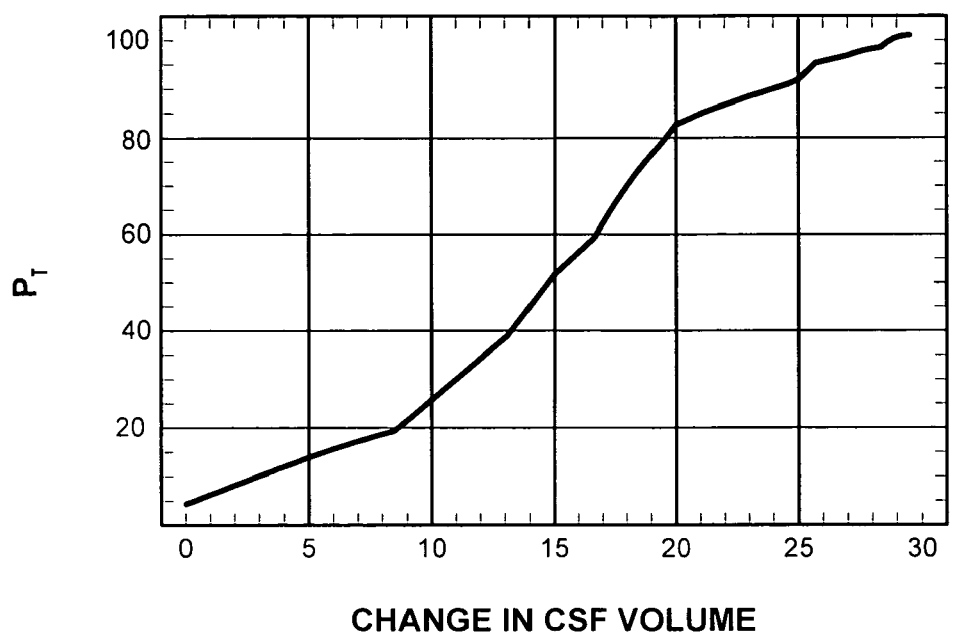
FIG. 8A illustrates one example of a chart of the predicted CSF pressure vs. volume.

The pressure-volume relation obtained by using the present embodiment to simulate CSF infusion tests is given in FIG. 8A. The pressure in this figure is the pressure $P_T$ of the extraventricular CSF compartment since this compartment contains the lower lumber portion of CSF space where clinical pressure recordings were made. The volume change in FIG. 8A represents the net change of both ventricular and extra-ventricular CSF volumes combined, as this is the quantity calculated in the experiments. The logistic-like shape of the predicted pressure-volume relationship is maintained until CSF pressures reach high values comparable to the systolic blood pressure. At this point, the curve turns upward and compliance rapidly decreases.

The same infusion simulations that led to the pressure-volume relationship in FIG. 8A may also be used to calculate a relationship between CSF pressure increases and CSF absorption. The slope of this relationship is known as the conductance of CSF outflow and is denoted by $C_{out}$. In model simulations, this value is easily calculated by $$C_{out}^m(t) = \frac{Z_{TS}(P_T(t) - P_S(t)) + Z_{TO}(P_T(t) - P_O(t)) - (\overline{Q}_{TS} + \overline{Q}_{TO})}{P_T(t) - \overline{P}_T} \tag{133}$$

where the superscript m denotes the model calculation and t denotes the time in minutes from the start of the simulated infusion. FIG. 5B illustrates the predicted conductance of CSF outflow throughout ten minutes of an infusion simulation.

Figure 8B:
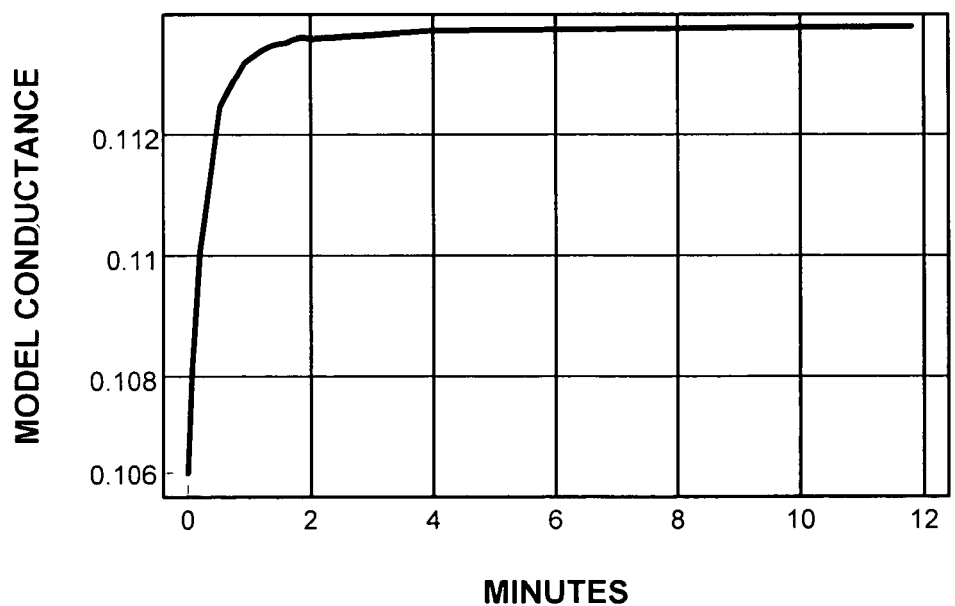
FIG. 8B illustrates one example of a chart of conductance to CSF output according to one embodiment of the present invention.

When $C_{out}$ has been studied experimentally, a linear relationship between CSF pressure increase and CSF absorption is observed. In prior art experiments, a mean value for $C_{out}$ of 0.11 (ml/min)/mm Hg is given for a sample of eight healthy volunteers, and it is stated that a value greater than 0.10 is probably normal. The values of the conductance of CSF outflow calculated from the present simulations are shown in FIG. 8B. These values change with time, but stay within 0.004 units of the mean value of 0.11 (ml/min)/mm Hg observed in the prior art. They are also greater than 0.10 as previously suggested. Furthermore, the calculated temporal variation of $C_{out}^m$ is sufficiently small that that the relationship between CSF pressure increase and CSF absorption might easily be categorized as linear on the basis of clinical data.

Figure 9:
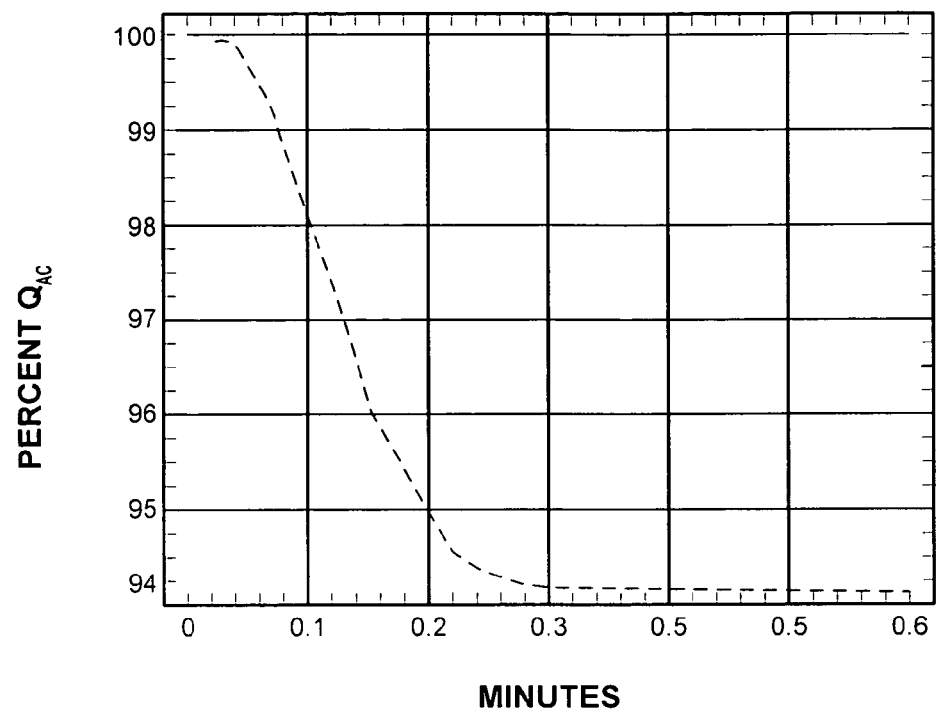
FIG. 9 illustrates one example of a chart of the percentage of $Q_{AC}$ drop due to a positional change with all SNS reflexes activated (solid) and without any SNS reflexes included (dashed)

In the current example calibrations, the pressures, flows, and hence resistances are determined from data associated with the body being in the horizontal (supine) position. Gravitational influences on the circulation will change when the body changes position. Upon standing up, the blood flow into the lower body is aided by gravity, but the venous return from the lower body is hindered by it. As the lower body in the present embodiment is represented by separate compartments, the effect of a positional change can be considered. To simulate the gravity-induced changes associated with standing up, the resistance into the lower arteries ($R_{IZ}$) may be decreased by one half while the resistance from the lower veins ($R_{XO}$) is doubled. This results in pressure and volume increases of the lower arteries and veins. In the current simulations, these resistance changes were made instantaneously and the modeled effect on cerebral blood flow was determined for the next 30 seconds. In the first simulation, all sympathetic nervous system (SNS) reflexes are intact and in the second these are removed. As can be seen in FIG. 9, with all SNS reflexes activated, cerebral blood flow is maintained at 100% of its original value.

Referring now to FIG. 9, the results of modifying the resistances between the central and lower body in the model to simulate a change in body position from lying down to standing up are illustrated. The solid curve in FIG. 9 indicates the response of cerebral blood flow to this change in position with the SNS reflexes included in the model equations. The simulation predicts that with all SNS reflexes activated, cerebral blood flow is maintained at 100% by the model through the change in body position. The dashed curve in FIG. 9 shows the predicted behavior of cerebral blood flow in the absence of regulation by the SNS.

When the SNS reflexes are removed from the model equations, cerebral blood flow drops to about 94% of its original value due to the positional change. This predicted decrease indicates the important role that the SNS regulatory mechanisms play in the maintenance of cerebral blood flow in the model. The decrease also confirms that loss of the SNS reflexes can be a factor in orthostatic intolerance. Syncope, or fainting, is a common event with many different causes. Syncope can be due to sudden vasodilatation (vasodepressor or "vasovagal" syncope) as well as postural hypotension, in which the normal vasoconstrictive reflex response to a transiently decreased cardiac output on standing is not sufficiently active. Postural hypotension can occur as the result of drugs, venous disease, sympathectomy, hypovolemia, peripheral neuropathy, in addition to degeneration of the sympathetic nervous system (primary autonomic insufficiency, or idiopathic orthostatic hypotension). Common to all causes of syncope is a decrease in cerebral blood flow to under 30 ml per 100 g brain tissue per minute from the usual 50-55 ml, about 55% of normal. This is well above the threshold for loss of electrical function, at 30% of normal, but is enough to cause a transient loss of consciousness. The calculated percentage decrease in cerebral blood flow in the current simulation with the SNS terms in the model equations omitted does not approach the levels associated with fainting due to a rapid change in position as the result of standing up too quickly, even with inactive SNS reflexes. However, cerebrovascular autoregulation in the current simulation remains uncompromised and will act to maintain cerebral blood flow despite sudden decreases in arterial pressure.

To demonstrate the potential predictive capabilities of the model in pathology, two situations were simulated. In the first of these, a simplified representation of cardiac arrest was created by suddenly terminating all cardiac forcing, i.e., setting $Q_{HI}=Q_{OH}=0$, at a specified time in the course of the simulation. In prior research by Gutyon, it is noted that "When heart pumping is stopped . . . the flow of blood everywhere in the circulation ceases a few seconds later. Without blood flow, the pressures everywhere in the circulation become equal after a minute or so. This equilibrated pressure level is called the mean circulatory filling pressure . . . at a volume 40 of 5000 ml, the filling pressure is the normal value of 7 mm Hg." Predicted results from the simulation were consistent with this statement. When all cardiac forcing was stopped in the simulation, all circulatory pressures tend to about 7.5 mm Hg after about 45 seconds. The small difference in the predicted and cited filling pressures may be partially due to the fact that total blood volume in the simulation was taken to be about 5600 ml rather than the 5000 ml.

Figure 10:
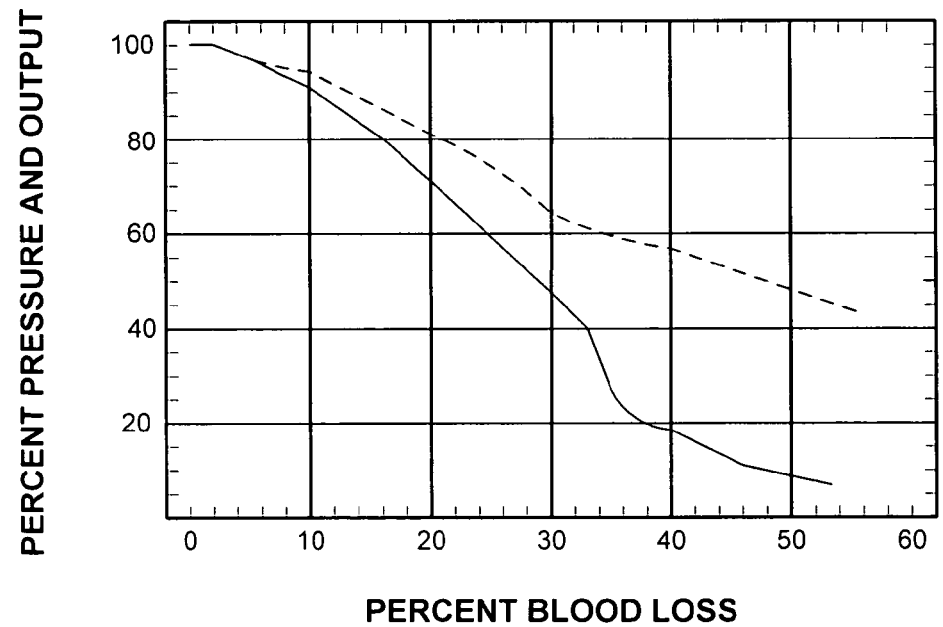
FIG. 10 illustrates one example of a chart of percentage decrease of $\overline{P}_I$ (solid) and of $\overline{Q}_{HI}$ (dashed) as a function of percentage blood loss due to hemorrhage.

Referring now to FIG. 10, the second pathological situation considered as a test of the model's capabilities involves the effects of shock caused by hypovolemia. In these simulations, a flow term $Q_{XM}$ was introduced into the equation for compartment X to model a hemorrhage from the lower body. Prior art research by Guyton gives a clinically-derived graph that, as in FIG. 10, depicts the percentage drop in central artery pressure ($P_I$) and cardiac output ($Q_{HI}$) with respect to percent blood loss. Consistent with these clinical results, the modeled response shows very stable pressure and cardiac output over the first 10% blood loss, and the relative arterial pressure stays above relative output during the entire course of the hemorrhage. At 30% blood loss, the relative drops in pressure and cardiac output are also in close agreement with the clinical results. During the course of the simulated hemorrhage, the central venous compartment contracts to less than 50% of its original volume, indicating that the active interface (SNSc) in the model is causing the central veins to strongly constrict in order to maintain blood flow back to the heart. Beyond 30% blood loss, a second arterial plateau is noticed in FIG. 10. This important feature, which is also noted in the clinical results, is due to the "last-ditch stand" reflex to maintain blood supply to the brain provided by the regulatory multiplier SNSz ($Q_{AC}$) in equation (130).

Figure 11:
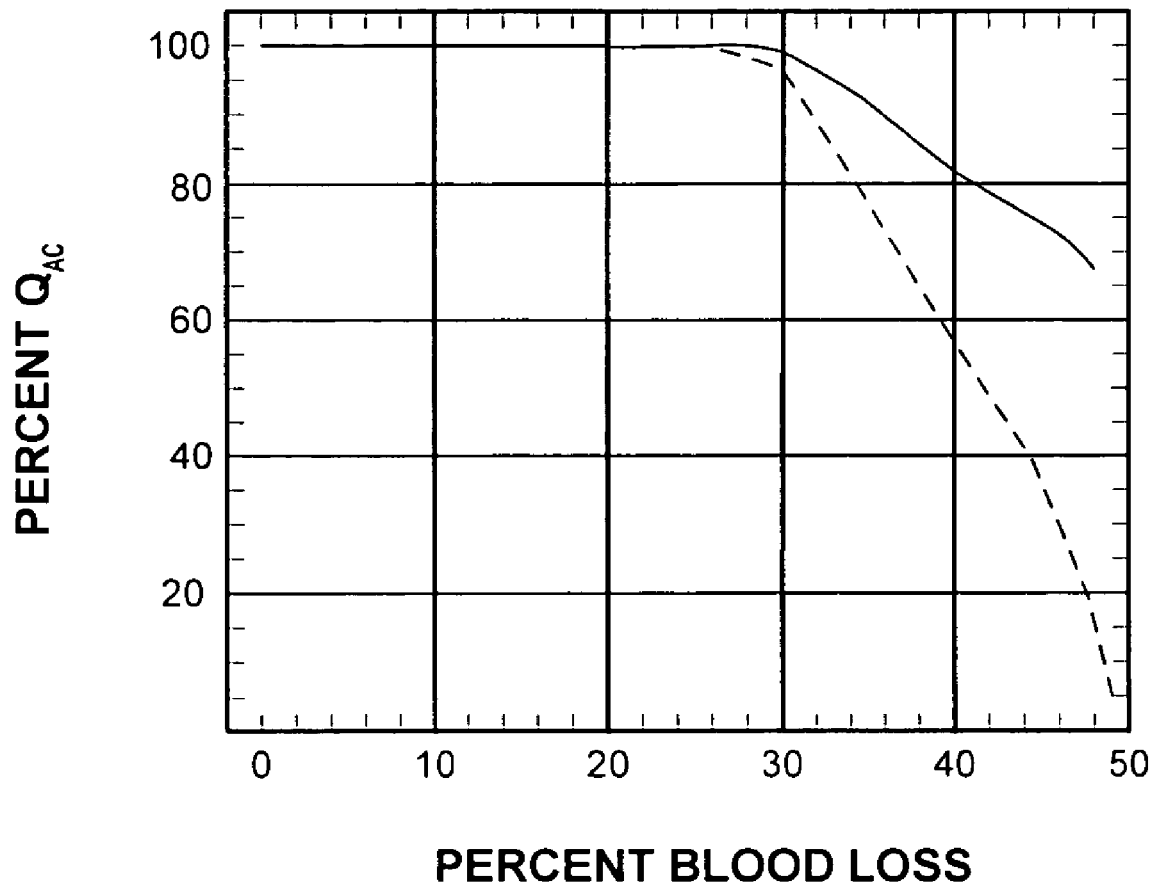
FIG. 11 illustrates one example of a chart of the predicted percentage of $Q_{AC}$ drop vs. percentage of blood loss due to hemorrhage with both SNSz reflexes activated (solid) and no SNSz reflexes included (dashed)

[Referring now to FIG. 11, the predicted percentage drop in cerebral blood flow ($Q_{AC}$) with respect to percent blood loss during the simulated hemorrhage is illustrated. The solid curve represents results when both SNSz mechanisms are intact, and the dashed curve represents results when both SNSz mechanisms are disabled. Both simulations predict that about 25% blood loss can be tolerated without a significant reduction in cerebral blood flow. Above this degree of blood loss, with the SNS mechanisms intact, the blood supply to the brain remains above about 75% of its original value. However, without these SNS regulatory mechanisms included in the model's equations, cerebral blood flow drops quickly to about 20% its original value.

The role of the SNS regulatory mechanisms in maintaining adequate central artery pressure and cardiac output has been noted above. However, the need to include the arteriole constrictive reflex SNSz in a model of intracranial pressure dynamics when simulating pathology is also dramatically illustrated by the behavior of cerebral blood flow as a function of blood loss in the hemorrhage simulations. Due to the intracranial autoregulatory mechanism $Z_{AC}$ in the model, a 25% blood loss can be tolerated without significant reduction in cerebral blood flow. Beyond this point, arteriole constriction is essential to further maintain adequate levels of cerebral blood flow. As indicated in FIG. 11, predicted cerebral blood flow $Q_{AC}$ remains above about 80% of its original value from about 25% blood loss through about 40% blood loss. By contrast, in an analogous simulation where the arteriole constrictive response was disabled, $Q_{AC}$ falls to approximately about 55% of its original value when about 40% blood loss has occurred. Between about 40% and about 45% blood loss, $Q_{AC}$ remains above about 75% of its original value with the arteriole constrictive response intact, but falls rapidly from about 55% to approximately 20% of its original value with the arteriole constrictive response disabled.

Most attempts to study intracranial pressure using lumped-parameter models have adopted the classical "Kellie-Monro Doctrine," which considers the intracranial space to be a closed system that is confined within the nearly-rigid skull, conserves mass, and has equal inflow and outflow. The present embodiment revokes this Doctrine and develops a mathematical model for the dynamics of intracranial pressures, volumes, and flows that embeds the intracranial system in extensive whole-body physiology. This new model consistently introduces compartments representing the tissues and vasculature of the extradural portions of the body, including both the thoracic region and the lower extremities. In addition to vascular connections, a spinal subarachnoid cerebrospinal fluid (CSF) compartment bridges intracranial and extracranial physiology allowing explicit buffering of intracranial pressure fluctuations by the spinal theca. The embodiment may include cerebrovascular autoregulation, regulation of systemic vascular pressures by the sympathetic nervous system, regulation of CSF production in the choroid plexus, a lymphatic system, colloid osmotic pressure effects, and realistic descriptions of cardiac output. Validation tests show that the embodiment's predictions are in agreement with experimental data for normal physiology. Additional simulations indicate that the present whole-body model embodiment appears to have significant potential predictive capabilities in situations involving pathological conditions.

Simplified Regulatory Mechanisms Embodiment

In a another embodiment, a logistic function is used in a model of a circulatory system to represent a regulatory mechanism parameter having an impact on circulatory system function. Such a logistic function may be used in a model according to the present disclosure. In one example, a logistic function according to the present embodiment may be used in conjunction with a model such as the whole-body embodiment described above. In another example, a logistic function according to the present embodiment may be used in another model including one or more time-dependent pressure functions representing the circulatory system. Solving the logistic function and time-dependent pressure function, a desired circulatory system value may be determined. A modeled circulatory system value can be used in combination with an actual measured circulatory system value of a subject for a variety of applications related to the subject. Example applications include, but are not limited to, etiology of Idiopathic Intracranial Hypertension, diagnosis of Idiopathic Intracranial Hypertension, treatment of Idiopathic Intracranial Hypertension, modeling behavior of intracranial pressure in microgravity environments, and any combinations thereof. Further discussion of an exemplary microgravity environment application is set forth in U.S. Provisional Patent Application No. 60/664,723 under the section entitled "Modeling steady-state intracranial pressures in supine, head-down tilt, and microgravity conditions." U.S. Provisional Patent Application No. 60/664,723 has been incorporated herein by reference in its entirety. In one example, a model of the present embodiment may be used as an educational tool for generating a model of a particular physiological system. In such an example a user may create a model of a desired physiological system and modify one or more parameters of the model to follow the impact that the change would have on the system. In another example, a model of the present embodiment may be used in conjunction with actual data collected from a subject to be studied. Using the real measured data in the model may allow prediction of outcomes from the model. These predictions may be used to treat the subject. One example of a prediction includes the prediction of cerebral blood flow from arterial pressure and blood loss data. A simplified example model utilizing a logistic function according to the present embodiment is described in further detail below with respect to FIGS. 12 to 21.

In one aspect, new mathematical representations model the autonomic and central nervous system reflexes which maintain arterial pressure, cardiac output, and cerebral blood flow. In one example, a model may include representations that model cardiac up-take, cerebral and non-cerebral blood flow, and the pressure-volume relationship in a vessel with smooth muscle contraction. Many of the factors in these relationships involve logistic functions. These functions allow regions of maximum and minimum effect to be smoothly connected through a logistic transition region.

In another aspect of the present embodiment, a method and system of modeling a pressure and volume relationship in a compliant vessel is provided. In one example, a first parameter is defined as a change in pressure within a vessel, the change in pressure being due to a contraction of smooth muscles of a wall of the vessel. A second parameter is defined as an active compliance of the vessel, the active compliance varying with internal pressure, external pressure, and the first parameter. The use of a smooth muscle contraction parameter is described in further detail below with a simplified example of a model according to the present embodiment.

Despite its facial simplicity, the present embodiment has the ability to accurately capture the physiological responses instigated by both the autonomic and central nervous systems to regulate cardiac output and arterial pressure and maintain the blood flow to the intracranial system necessary to preserve essential brain function. Several of these nervous system regulatory mechanisms are continuously active and maintain a nearly constant arterial pressure under a moderate range of stimuli. Others remain inactive until circumstances develop that require a triggering of extreme countermeasures to maintain vital blood flow.

To formulate a lumped-parameter model of a physiological system, the system must first be divided into an appropriate number of interacting subunits or "compartments." The number of compartments used may depend on a number of considerations including, but not limited to, the intended application of the model, equation solving resources, the need for special resolution, and any combinations thereof. In one aspect, a model compartment may not necessarily correspond to a precise physical location in the body. For example, in a lumped parameter model with a single arterial compartment, arterial blood in the thoracic region cannot be distinguished from arterial blood in the intracranial arteries. This is one of the main limitations of the lumped-parameter approach. Because compartmental variables are assumed to be spatially averaged over the full extent of a compartment, additional spatial resolution can be realized by subdividing the physical system into a larger number of compartments. For example, to improve spatial resolution, three arterial compartments containing blood in the upper, central, and lower body might be included as opposed to a single lumped arterial compartment. In principle, the systemic circulation could be finely subdivided in this manner into a sufficient number of separate compartments to provide any desired degree of spatial resolution. Clearly this subdivision process cannot be carried to an extreme as the resulting system of linked governing equations will rapidly become too large for practical analysis and solution. However, extensive subdivision of the physical system is seldom needed in this modeling approach. A strength of lumped-parameter models is their ability to represent a system over a wide range of parameter values using a reasonable (and often small) number of compartments. Further, lumped-parameter models not only allow the full extent of the physiological system to be studied, but different subsystems can be consistently linked so that interactions between subsystems, as well as interactions between physical mechanisms, can be realistically studied.

Aspects of the present embodiment are described below using a simplified model. The example divides the systemic circulation into two main compartments representing the arteries and the veins. Two flow pathways, representing cerebral blood flow to the brain and non-cerebral blood flow, directly connect these two compartments. The example model also contains a simplified heart pump that provides forcing for the system. Cardiac output to the arterial compartment is assumed equal to cardiac up-take from the venous compartment. This implies a conservation of blood volume in the pulmonary circulation, and allows the model to focus on the systemic circulation by consistently omitting the pulmonary system in the model's description of the cardiovascular system.

Figure 12:
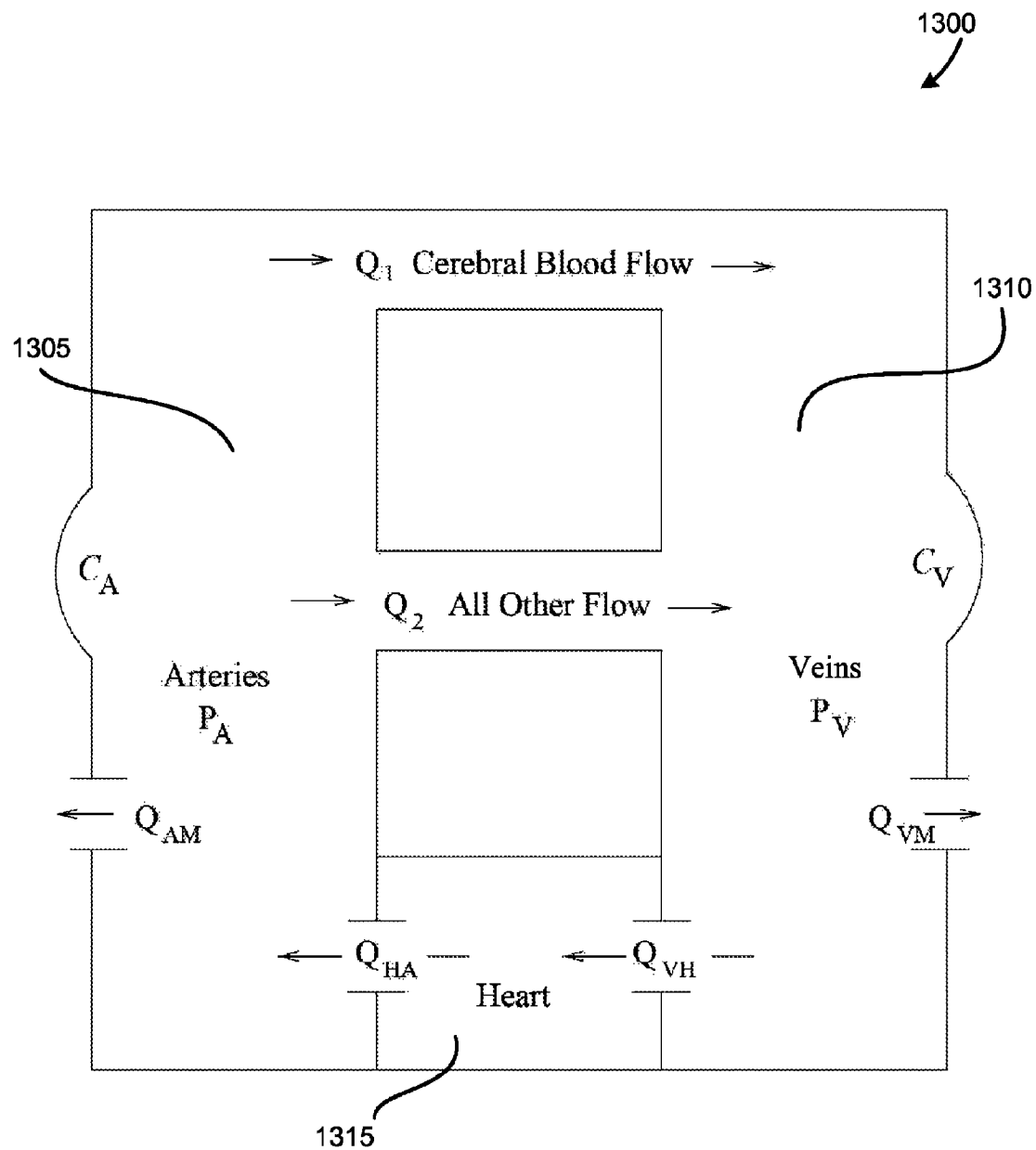
FIG. 12 illustrates one example of simplified schematic of another embodiment of a circulatory system model.

Referring to FIG. 12, a schematic 1300 of this example model of the present embodiment is illustrated. In this example, schematic 1300 includes only two main compartments: an arteries compartment 1305, represented by an A, and a veins compartment 1310 represented by the indication of a V Each of these compartments has an associated time-dependent pressure function, denoted by $P_A$ and $P_V$ respectively (e.g., measured in millimeters of mercury, "mm Hg"), that is spatially averaged over the entire subunit and temporally averaged over one cardiac cycle. No attempt has been made to depict relative volumes in FIG. 12, and hence the relative sizes of these compartments in the figure do not necessarily reflect relative volumes. Schematic 1300 also includes a heart pump 1315 for which cardiac uptake $Q_{VH}$ (e.g., measured in milliliters per minute, "ml/min"), the inlet flow to the right atrium, equals cardiac output $Q_{HA}$, the outlet flow from the left ventricle. This constraint imposes a zero volume change in the pulmonary circulation and allows the pulmonary system to be consistently omitted from the exemplary model. Each of arteries compartment 1305 and veins compartment 1310 has an associated volume function, denoted by $V_A$ and $V_V$, respectively. Volumes are related to pressures and smooth muscle contraction through active compliance terms $C_A$ and $C_V$. The model has two pathways for blood to flow directly between the arteries and veins. Cerebral blood flow is denoted by $Q_1$ and all other flow is denoted by $Q_2$. This distinction is made because cerebral blood flow, which may constitute approximately 15 percent of cardiac output, is well regulated and remains nearly constant under a wide range of arterial pressures to maintain essential brain function. While this is also true of blood flow to the heart itself, flow to the heart muscle constitutes only about 4 to 5 percent of cardiac output and is separately regulated. The flow terms $Q_{AM}$ and $Q_{VM}$ are included in the model to allow simulations of hemorrhage and represent blood flow into a non-vascular region.

Considering blood to be incompressible and balancing inflows, outflows, and volume adjustments in each compartment yields the preliminary governing equations $$\dot{V}_A = Q_{HA} - Q_1 - Q_2 - Q_{AM} \tag{134}$$

$$\dot{V}_V = Q_1 + Q_2 - Q_{VM} - Q_{VH} \tag{135}$$

The dot on the left hand side of these equations designates a derivative with respect to time.

Much of the dynamic behavior described by this embodiment involves a response that is bounded by a minimum value and a maximum value with a smooth logistic transition between the two. To aid in the modeling of these responses, two preliminary logistic functions are defined in the example by $$L_{inc}(x, r, \max, \min) = \max + \frac{\min - \max}{1 + \frac{1 - \min}{\max - 1} e^{rx}} \tag{136}$$

$$L_{dec}(x, r, \max, \min) = \max + \frac{\min - \max}{1 + \frac{1 - \min}{\max - 1} e^{-rx}} \tag{137}$$

where $r>0$, $-\infty<x<\infty$, and $\min<L_{inc},L_{dec}<\max$. The increasing logistic function $L_{inc}$ tends to max as $x\rightarrow\infty$ and to min as $x\rightarrow-\infty$. The decreasing logistic function behaves in the opposite manner. Both functions equal unity at $x=0$, and have an inflection point at the average of max and min.

Cerebral Blood Flow: $Q_1$

Figure 13:
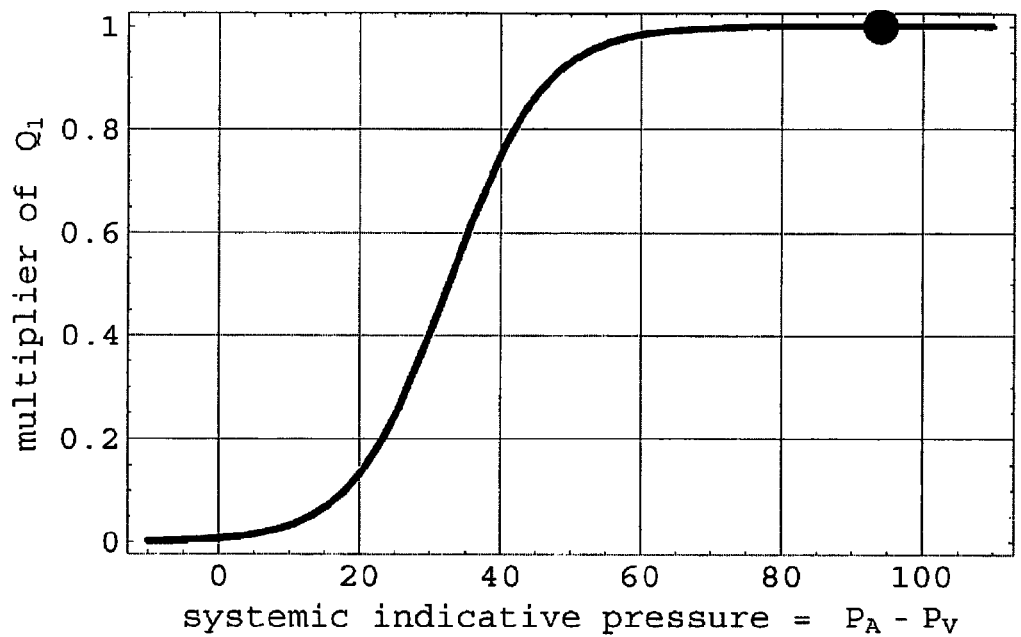
FIG. 13 illustrates one example of a chart of a multiplier of $Q_I$ vs. systemic indicative pressure, $P_A - P_V$.

Normal blood flow through the brain is governed by the pressure gradient between the cerebral arteries and the brain, termed the perfusion pressure. As the present example does not have an explicit brain compartment, the pressure difference $P_A-P_V$, denoted by $P_{AV}$ will act as a surrogate for perfusion pressure. In this context, $P_{AV}$ will be termed the "systemic indicative pressure". Clinical data shows that the flow, $Q_1$, remains nearly constant for arterial pressures between about 60 and about 150 mm Hg. Casting this in the context of flow with respect to systemic indicative pressure, $Q_1$ is defined here by $$Q_1 = L_{inc}(P_{AV} - \overline{P}_{AV}, 0.15, 1.0001, 0) \cdot \overline{Q}_1 \tag{138}$$

where $\overline{P}_{AV}$ is the mean systemic indicative pressure and $\overline{Q}_1$ is the mean cerebral blood flow. The multiplier function $L_{inc}$ is depicted in FIG. 13. The dot in the figure is located at the mean systemic indicative pressure. $Q_1$ thus remains nearly constant until indicative pressure drops below about 60 mm Hg. As venous pressure remains near zero, this threshold corresponds to an arterial pressure that is also near 60 mm Hg.

Non-cerebral Blood Flow: $Q_2$

Non-cerebral blood flow, $Q_2$, is similarly governed by a pressure difference, $P_{AV}$. Unlike $Q_1$, it will not be modeled by an expression such as in Equation (138). Instead it will be governed by the hydrodynamic version of Ohm's law $$Q_2 = (P_A - P_V)/R_2 = Z_2 P_{AV} \tag{139}$$

where $Z_2$ is the inverse of resistance, termed the fluidity or conductance. In many mathematical models of this type, fluidities are taken to be constant in a linearization of the governing equations. However, in the present example, $Z_2$ will be allowed to vary with both pressures and time. Consequently, the embodiment's governing differential equations (134) and (135) will be nonlinear. $Z_2$ includes three factors;

$$Z_2 = ANSz \cdot CNSz \cdot \overline{Z}_2 \tag{140}$$

where $\overline{Z}_2 = \overline{Q}_2/\overline{P}_{AV}$ and the factors ANSz and CNSz vary in such a way that they maintain arterial pressure. The functions used to represent ANSz and CNSz are described below in relation to details of regulation mechanisms.

Cardiac Uptake and Output, OVP

Cardiac output plays a major role in the regulation of arterial blood pressure with below-normal arterial pressures causing an increase in cardiac output and above-normal pressures causing a decrease in cardiac output. In the present example model, cardiac output $Q_{HA}$ has been set equal to cardiac uptake $Q_{VH}$. Venous return and venous pressure are two of the major determinants of cardiac uptake. If either is allowed to drop significantly, cardiac output will diminish.

Cardiac uptake is modeled here in terms of the venous return $Q_1+Q_2-Q_{VM}$ and a regulatory multiplier M based on central venous pressure and nervous system regulation. In particular, $$Q_{VH}=M\cdot(Q_1+Q_2-Q_{VM}). \tag{141}$$

The dependence of $Q_{VH}$ on the venous return is thus explicit in Equation (141), and when M=1, consistent with the Frank-Starling mechanism of the heart. See, Guyton et al., *Textbook of Medical Physiology*, 10$^{th}$ Ed. 2000 (cardiac uptake is equal to venous return), which is incorporated herein by reference in its entirety. The effect of venous pressure on cardiac uptake is included in the current model through a factor, OVP (output versus pressure), in the cardiac uptake multiplier M. In particular, M is defined to be $$M=OVP\cdot ANSo\cdot CNSo \tag{142}$$

where OVP is represented by the logistic function $$OVP(P_V)=L_{inc}(P_V-\overline{P}_V,0.5,2.5,0). \tag{143}$$

Figure 14:
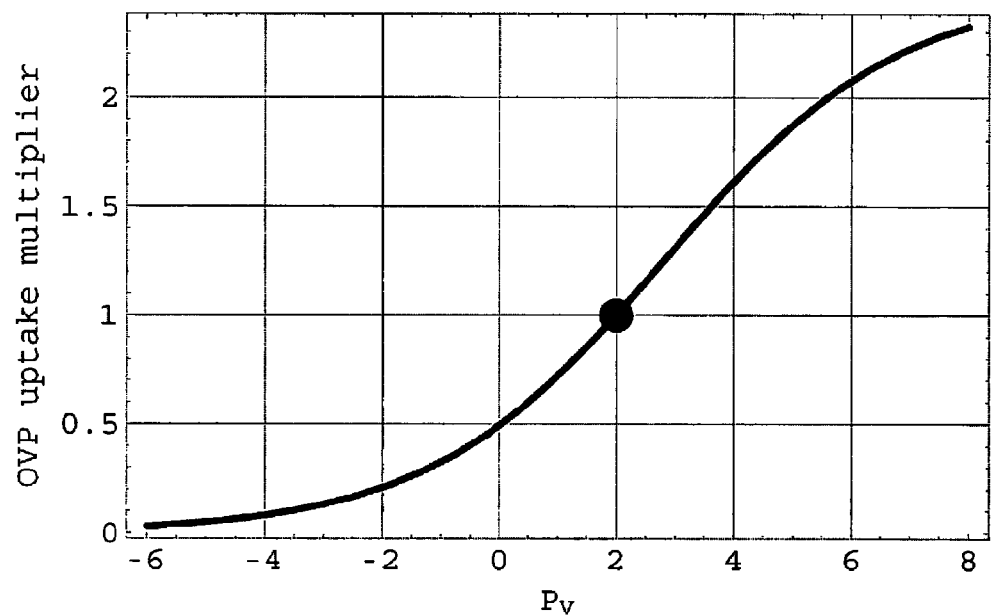
FIG. 14 illustrates one example of a chart of an OVP cardiac uptake multiplier vs. $P_V$.

The behavior of OVP is shown in FIG. 14. The dot in the plot is located at the mean venous pressure. Representations used in the model for the ANSo and CNSo factors in M are described in more detail below.

Nervous System Regulation of Cardiac Output, Arterial Pressure, and Cerebral Blood Flow Cardiac output and arterial pressure are well regulated. Further, since systemic perfusion pressure is most sensitive to the relatively large arterial pressure, maintaining arterial pressure can insure adequate blood flow to the brain. Two levels of regulation are present in the current example of the present embodiment. The first level represents the autonomous nervous system (ANS), which provides a regulatory response based on changes in arterial blood pressure, transmitted via the baroreceptors located in the walls of the carotid arteries and arch of the aorta. The second level represents the ischemic response of the central nervous systems (CNS), which is triggered by a significant reduction in cerebral blood flow.

Autonomic Nervous System (ANS) Regulation: ANS effects on cardiac output: ANSo

Figure 15:
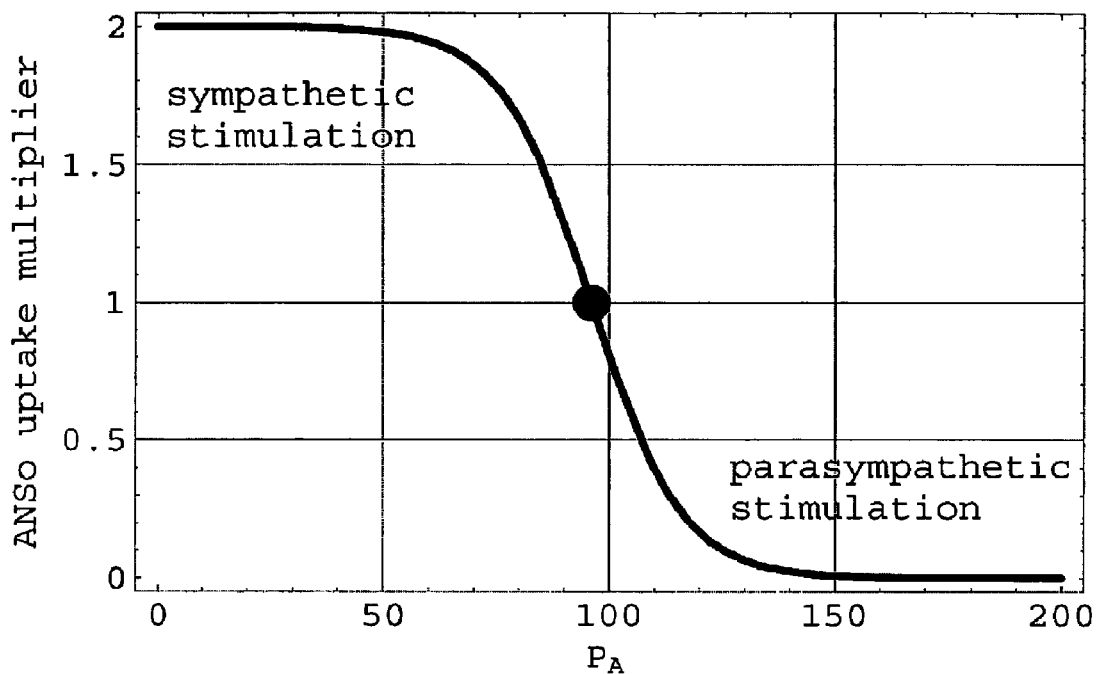
FIG. 15 illustrates one example of a chart of an $ANS_O$ cardiac uptake multiplier vs. $P_A$.

Changes in the heart rate, and hence the cardiac output, due to changes in arterial pressure are included in the present example through the factor ANSo in the multiplier M defined in equation (142). ANSo thus helps determine how the cardiac output differs from the venous return. This factor, depicted in FIG. 15, is defined logistically by $$ANSo=L_{dec}(P_A-\overline{P}_A,0.1,2,0) \tag{144}$$

where $\overline{P}_A$ is the normal mean arterial pressure. The dot in the plot of FIG. 15 is located at the mean arterial pressure of about 96 mm Hg.

Autonomic Nervous System (ANS) Regulation: ANS Effects on Non-Cerebral Blood Flow: ANSz ANSz represents the vasoconstriction or vasodilation of the arterioles based on changes in arterial pressure. This effect is included in the example model by varying the fluidity $Z_2$ in equation (140) through the factor ANSz, defined by the logistic expression $$ANSz=L_{inc}(P_A-\overline{P}_A,0.3,1.1,0.7). \tag{145}$$

Figure 16:
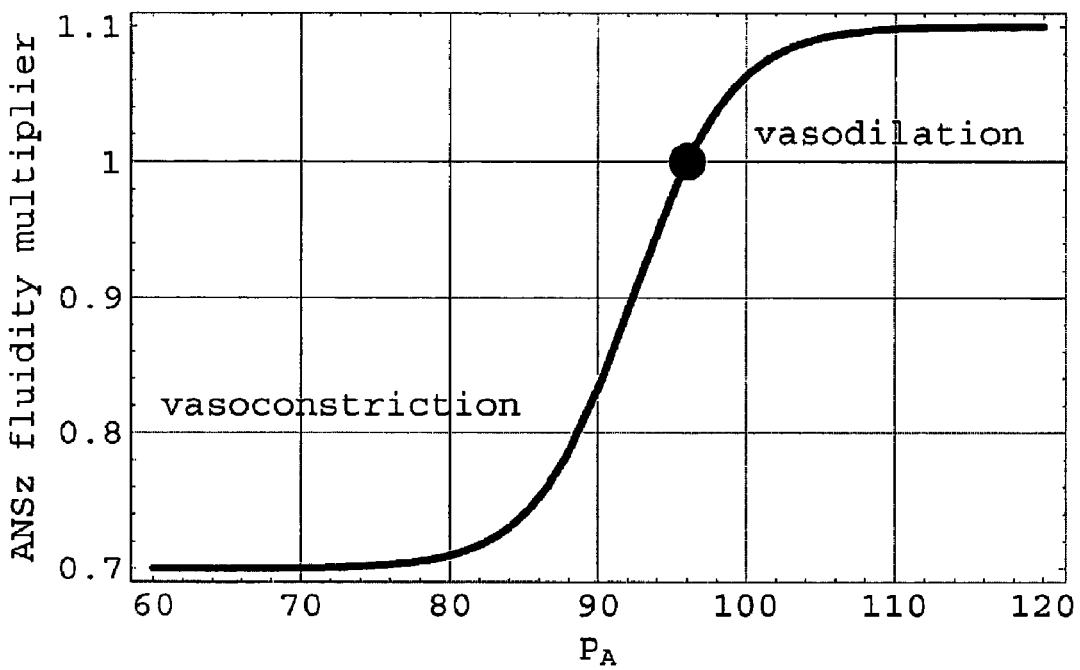
FIG. 16 illustrates one example of a chart of an $ANS_Z$ fluidity multiplier vs. $P_A$.

This function is depicted in FIG. 16. The dot in the plot is located at a mean arterial pressure of about 96 mm Hg.

ANS Effects on Smooth Muscle Contraction in the Walls of the Large Vessels

While the two types of ANS reflexes described above will aid in maintaining arterial pressure, they will not by themselves necessarily return arterial pressure to its initial mean value. Indeed, from a dynamical systems perspective, there are infinitely many steady state solutions to equations (134) and (135) in which arterial pressure is not at its initial mean value. An additional ANS regulatory mechanism may therefore be included in the model of the present embodiment to ensure that arterial pressure returns to its initial mean value under a wide range of stimuli. Smooth muscle contraction in the walls of the large vessels provides this further mechanism by which the ANS regulates arterial pressure and cardiac output. This mechanism is incorporated into the current example by developing a new form of the pressure-volume relationship in a compliant vessel with smooth muscle contraction.

The total effect of smooth muscle contraction on the pressure, volume, and compliance of the large vessels is not well understood. However, at a constant pressure, smooth muscle contraction decreases vessel volume, while smooth muscle contraction increases pressure at a constant volume. Therefore an equation describing the pressure-volume relationship in a compliant vessel with smooth muscle contraction may be derived from a few basic assumptions.

For purposes of this example of the embodiment, it is assumed that each vessel has a maximum volume $V^{Max}$ and a minimum volume of zero, and that the transition between these extreme values will be logistic in nature. This behavior is exhibited by the logistic function relation $$V(P) = \frac{V^{Max}}{1+e^{-r(P-P^*)}} \tag{146}$$

where P is the pressure inside the vessel, P* is the pressure outside of the vessel, and r>0. The maximum slope, and hence maximum compliance, occurs at P=P*. In the present case, the ambient pressure P* (e.g., measured in mm Hg) will be considered zero. However, P* will be retained in equation (146) as more complex models may consider these vessels residing inside the body where the ambient pressure is slightly below zero.

It is further assumed that the curve defined by V(P) shifts to the right during smooth muscle contraction. This is equivalent to a decrease in volume at a given pressure, or alternatively an increase in pressure at a given volume. This shift is a pressure increment that will be denoted by φ. Consistent with the findings of Bank et al., "In Vivo Human Brachial Artery Elastic Mechanics, Effects of Smooth Muscle Relaxation", *Circulation* 100 (1999) pp. 41-47 and Boutouyrie et al., "Sympathetic Activation Decreases Medium-Sized Arterial Compliance in Humans," *Am. J. Physiol.* 267 (1994) pp.

H1368-H1376 (each of which is incorporated herein by reference in their entirety) with regard to brachial artery pressure and cross-sectional area, it appears that arterial pressure can be doubled due to contraction while venous pressure can be elevated by as much as about 12 mm Hg. It further appears that arterial pressure can be reduced by one half the mean arterial pressure and venous pressure can be reduced by about 8 mm Hg through this mechanism. Therefore, in one example, the arteries ϕ will be bounded by the range $-\overline{P}_A/2 < \phi_A < \overline{P}_A$ and by $-8 < \phi_V < 12$ mm Hg in the veins. The maximum pressure generated by smooth muscle contraction in the arteries will be denoted by $\phi_A^{Max}$ and in the veins by $\phi_V^{Max}$. Likewise the minimum pressure generated will be denoted by $\phi_A^{min}$ in the arteries and $\phi_V^{min}$ in the veins. It will also be assumed that in the resting state, the pressure generated by smooth muscle contraction is zero.

Including the shift ϕ due to smooth muscle contraction, the expression for V in equation (146) now becomes $$V = \frac{V^{Max}}{1 + e^{-r(P-(\phi+P^*))}} \quad (147)$$

where ϕ increases as the smooth muscle contracts.

Assuming that r and $V^{Max}$ are constants, V can be differentiated with respect to time to give $$\dot{V} = C \cdot (\dot{P} - (\dot{\phi} + \dot{P}^*)) \quad (148)$$

where $$C = \frac{rV^{Max} e^{-r(P-(\phi+P^*))}}{(1 + e^{-r(P-(\phi+P^*))})^2} \quad (149)$$

and a dot again denotes a time derivative. Here, C represents a type of compliance which varies depending on internal pressure, external pressure, and the pressure generated from smooth muscle contraction. C is referred to as an active compliance.

Compliance Calibration

In compartmental models which do not include smooth muscle contraction, volume adjustments are directly related to pressure changes through the equation dV/dt=C dP/dt where C is a traditional compliance. With smooth muscle contraction included, equation (148) shows that this traditional relationship will be modified. However, when both the pressure shift ϕ and the ambient pressure P* are constants, so that $\dot{\phi} = \dot{P}^* = 0$, equation (148) reduces to the traditional relationship and the active compliance C becomes a traditional compliance. Consequently, parameter calibration can be accomplished in accordance with clinical results where there is no change due to smooth muscle contraction.

The variables in equations (148) and (149) will be identified with a subscript indicating the arterial (A) or venous (V) compartment. Scale values for $\tau_A$, $\tau_V$, $V_A^{Max}$, and $V_V^{Max}$ are calculated by imposing the following constraints:

$$V_A(\overline{P}_A, \overline{\phi}_A, \overline{P}^*_A) = \overline{V}_A, \quad (150)$$

$$V_V(\overline{P}_V, \overline{\phi}_V, \overline{P}^*_V) = \overline{V}_V, \quad (151)$$

$$C_A(\overline{P}_A, \overline{\phi}_A, \overline{P}^*_A) = \overline{C}_A, \quad (152)$$

$$C_V(\overline{P}_V, \overline{\phi}_V, \overline{P}^*_V) = \overline{C}_V, \quad (153)$$

where, in this model, $\overline{\phi}_A = \overline{\phi}_V = \overline{P}^*_A = \overline{P}^*_V = 0$. The mean volumes and compliances on the right hand side of equations (150) to (153) are similar to those of the whole body embodiment described above. The arterial and venous versions of equation (148) are used to define the left hand side of the governing equations (134) and (135).

Instead of explicitly defining $\phi_A$ and $\phi_V$, the dynamics generated by these terms are included through the introduction of two appended differential equations that are solved simultaneously with equations (134) and (135). These equations are $$\dot{\phi}_A = k_A(\overline{P}_A - P_A)(\phi_A^{Max} - \phi_A)(\phi_A - \phi_A^{min})(\alpha_A \phi_A + \beta_A) \quad (154)$$

$$\dot{\phi}_V = k_V(\overline{P}_A - P_A)(\phi_V^{Max} - \phi_V)(\phi_V - \phi_V^{min})(\alpha_V \phi_V + \beta_V) \quad (155)$$

where $k_A$ and $k_V$ are positive. The last term in each of these differential equations is a linear expression in which α and β are determined so that the maximum value of the product of the last three terms is unity and this value occurs at the mean value ϕ. Additionally the product of these three terms must remain positive for $\phi^{min} \leq \phi \leq \phi^{Max}$. These constraints are satisfied, when $\overline{\phi} = 0$, by the following assignments for α and β in each vessel type:

$$\alpha = -\frac{\phi^{Max} + \phi^{min}}{(\phi^{Max}\phi^{min})^2}, \quad (156)$$

$$\beta = -(\phi^{Max}\phi^{min})^{-1}. \quad (157)$$

Equations (154) to (157) imply that smooth muscle contraction is most sensitive when $\phi = \overline{\phi}$. Furthermore, the contraction is initiated by a drop in arterial pressure and is bounded between a maximum value of $\phi^{Max}$ and a minimum value $\phi^{min}$. Under these conditions, numerical simulations imply that appropriate example values for the rate constants in equations (154) and (155) are $k_A \approx 0.3$ and $k_V \approx 0.8$.

With the inclusion of equations (154) and (155) above, the systemic circulatory system will not come to rest until mean arterial pressure is achieved or a limiting value of contraction is achieved in both types of vessels. Therefore, so long as contraction is not at an extremum in both vessels, arterial pressure will return to normal. This mechanism can be an important factor in maintaining arterial pressure at its mean value and finalizes the regulation of arterial blood pressure via the ANS mechanisms.

Central Nervous System (CNS) Regulation: Ischemic Response

When blood flow through the intracranial region is significantly diminished, the brain can become ischemic, and powerful responses are rapidly instigated by the central nervous system to restore arterial pressure. These responses include increased heart rate and vasoconstriction of the arterioles leading to the non-vital organs.

CNS Effects on Cardiac Output: CNSo

Figure 17:
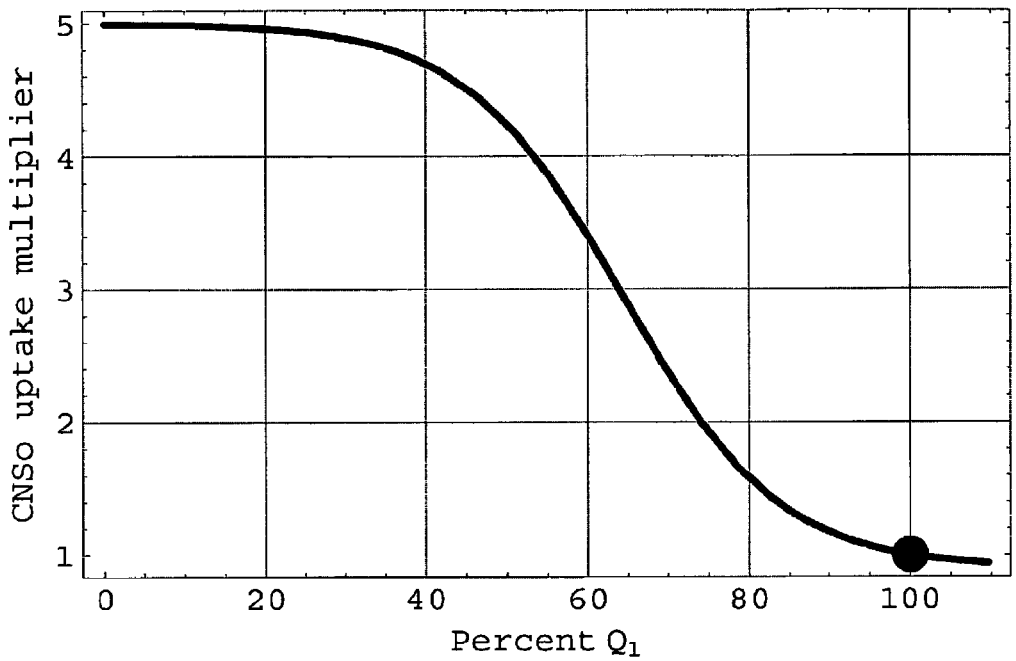
FIG. 17 illustrates one example of a chart of an $CNS_O$ cardiac uptake multiplier vs. percent $Q_I$.

The factor CNSo in the multiplier M defined by equation (142) is associated with a severe change in heart rate triggered by significant reductions in the cerebral blood flow $Q_1$. This effect is included in the model as the determining component of cardiac uptake, and is defined logistically by $$CNSo = L_{dec}(Q_1 - \overline{Q}_1, 0.01, 5, 0.9) \quad (158)$$

where $\overline{Q}_1$ is the mean cerebral blood flow. In FIG. 17, CNSo is depicted with respect to the percent change in $Q_1$ from the original value $\overline{Q}_1$. The dot in the plot indicates a mean value.

CNS effects on Non-Cerebral Blood Flow: CNSz

CNSz is associated with the severe vasoconstriction in the arterioles of the non-vital tissues based on changes in cerebral blood flow. This effect is included in this embodiment of a model as a factor of $Z_2$ in equation (140) and is defined by $$CNSz = L_{inc}(Q_1 - \overline{Q}_1, 0.01, 1.01, 0.1). \tag{159}$$

Figure 18:
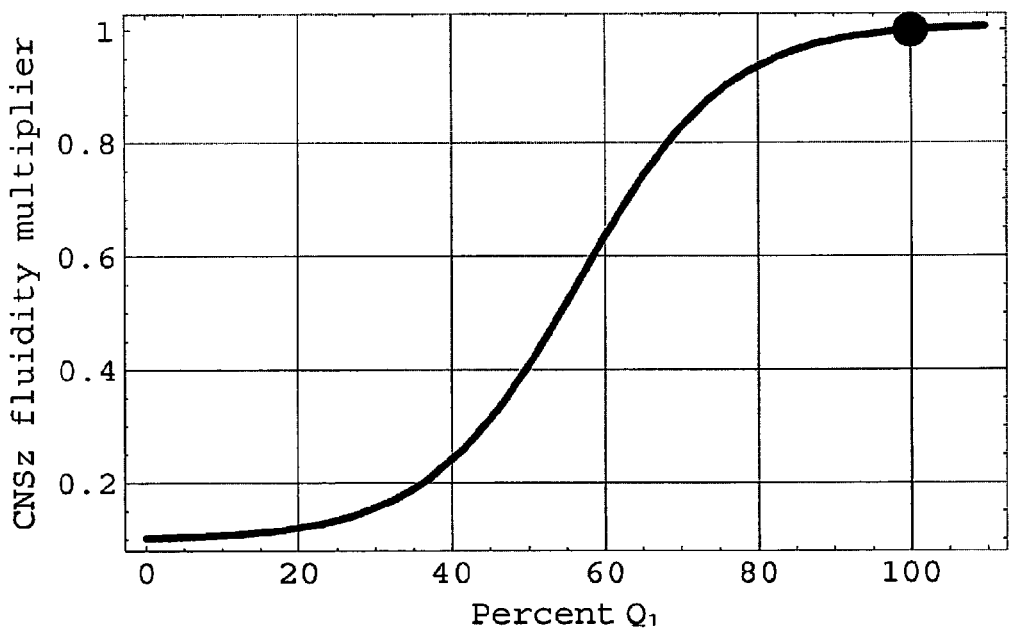
FIG. 18 illustrates one example of a chart of an $CNS_Z$ fluidity multiplier vs. percent $Q_I$.

In FIG. 18, CNSz is depicted with respect to the percent change in $Q_1$ from the original value $Q_1$. The large dot in the plot indicates a mean value.

Detailed Governing Equations

Assuming $P^*_A = P^*_V = 0$, the embodiment's governing equations may now be obtained from the preliminary equations (134)-(135), equations (148)-(149), and equations (154)-(155). They take the form $$C_A \cdot (\dot{P}_A - \dot{\phi}_A) = Q_{VH} - Q_1 - Q_2 - Q_{AM} \tag{160}$$

$$C_V \cdot (\dot{P}_V - \dot{\phi}_V) = Q_1 + Q_2 - Q_{VM} - Q_{VH} \tag{161}$$

$$\dot{\phi}_A = k_A (\overline{P}_A - P_A)(\phi_A^{Max} - \phi_A)(\phi_A - \phi_A^{min})(\alpha_A \phi_A + \beta_A) \tag{162}$$

$$\dot{\phi}_V = k_V (\overline{P}_A - P_A)(\phi_V^{Max} - \phi_V)(\phi_V - \phi_V^{min})(\alpha_V \phi_V + \beta_V) \tag{163}$$

where $$Q_{VH} = ANSo \cdot CNSo \cdot OVP \cdot (Q_1 + Q_2 - Q_{VM}) \tag{164}$$

$$Q_1 = L_{inc}(P_{AV} - \overline{P}_{AV}, 0.15, 1.0001, 0) \cdot \overline{Q}_1 \tag{165}$$

$$Q_2 = ANSz \cdot CNSz \cdot \overline{Z}_2 \cdot (P_A - P_V) \tag{166}$$

$$C_A = \frac{r_A V_A^{Max} e^{-r_A (P_A - \phi_A)}}{(1 + e^{-r_A (P_A - \phi_A)})^2} \tag{167}$$

$$C_V = \frac{r_V V_V^{Max} e^{-r_V (P_V - \phi_V)}}{(1 + e^{-r_V (P_V - \phi_V)})^2}. \tag{168}$$

ANSo is defined in equation (144), CNSo is defined in equation (158), OVP is defined in equation (143), ANSz is defined in equation (145), CNSz is defined in equation (159), $Q_{VH}$ is the cardiac uptake, and for the heart pump in the present example the cardiac output $Q_{HA} = Q_{VH}$.

Simulations

To test the validity of this example model's representations of the nervous system regulatory mechanisms as well as to explore potential applications of the model to pathological situations, cardiac arrest and various levels of hypovolemic shock were simulated. All simulations were initiated from a normal resting mean state with values $$P_A(0) = \overline{P}_A = 96, \tag{169}$$

$$P_V(0) = \overline{P}_V = 2, \tag{170}$$

$$\phi_A(0) = \overline{\phi}_A = 0, \tag{171}$$

$$\overline{\phi}_V(0) = \overline{\phi}_V = 0, \tag{172}$$

so that the initial value problem involving equations (160) to (163) is completely defined. The value of the cardiac output multiplier M and values of the factors ANSz and CNSz in the fluidity $Z_2$ were initially set equal to unity in the simulations and then allowed to vary according to equations (142), (145), and (159). Values of additional quantities and parameters used in the simulations are given in Table 1. The initial value problem for the model's governing nonlinear differential equations was then solved numerically using the mathematical software package Mathematica, which is available from Wolfram Research Inc., of Champaign, Ill. employing maximum accuracy and precision settings.

Cardiac arrest was simulated in the model by setting cardiac uptake and output to zero and deactivating all autoregulatory mechanisms. The pressure to which both $P_A$ and $P_V$ rapidly tend in this simulation is known as the mean circulatory filling pressure.

Simulated hemorrhages were studied by assigning a hemorrhage rate to $Q_{AM}$ and/or $Q_{VM}$ In the first case, a total blood loss of 45 percent over 30 minutes was simulated, and the relative change in arterial pressure and cardiac output over the course of the hemorrhage were determined. In a second group of simulations, six hemorrhage situations with lesser degrees of total blood loss were studied. These cases involved hemorrhaging 24, 28, 31, 36, 41, and 43 percent of total blood volume. These simulations were continued beyond the point where the hemorrhage was terminated to determine if a recovery of arterial pressure was predicted with the model's regulatory mechanisms both active and disabled. Finally, to test the ability of the model to accurately capture the overall effect of the ANS reflexes, a hemorrhage of 10 percent of blood volume was simulated with the ANS mechanisms fully active and with the ANS mechanisms deactivated.

TABLE 1

Initial and Calibrated Values Used in the Simulations

| Symbol | Value | Units | Description |
|---|---|---|---|
| $\overline{P}_A$ | 96 | mmHg | mean (initial) arterial pressure |
| $\overline{P}_V$ | 2 | mmHg | mean (initial) venous pressure |
| $\overline{\phi}_A$ | 0 | mmHg | mean (initial) value of $\phi_A$ |
| $\overline{\phi}_V$ | 0 | mmHg | mean (initial) value of $\phi_V$ |
| $\overline{V}_A$ | 1150 | ml | mean (initial) arterial volume |
| $\overline{V}_V$ | 4450 | ml | mean (initial) venous volume |
| $\overline{Q}_{VH}$ | 6900 | ml | mean cardiac uptake |
| $\overline{Q}_{HA}$ | 6900 | ml | mean cardiac output |
| $\overline{Q}_1$ | $0.15 \cdot \overline{Q}_{VH}$ | ml/min | mean cerebral blood flow |
| $\overline{Q}_2$ | $0.85 \cdot \overline{Q}_{VH}$ | ml/min | mean remaining blood flow |
| $P^*_A \equiv \overline{P^*}_A$ | 0 | mmHg | ambient arterial pressure |
| $P^*_V \equiv \overline{P^*}_V$ | 0 | mmHg | ambient venous pressure |
| $\overline{C}_A$ | 2.93657 | ml/mmHg | mean arterial compliance |
| $\overline{C}_V$ | 90.8934 | ml/mmHg | mean venous compliance |
| $V_A^{Max}$ | 1318 | ml | maximum arterial volume |
| $V_V^{Max}$ | 8536 | ml | maximum venous volume |
| $r_A$ | 0.02005 | none | arterial compliance parameter eq. (34) |
| $r_V$ | 0.04267 | none | venous compliance parameter eq. (35) |
| $\phi_A^{Max}$ | 96 | mmHg | maximum value of $\phi_A$ |
| $\phi_V^{Max}$ | 12 | mmHg | maximum value of $\phi_V$ |
| $\phi_A^{min}$ | −48 | mmHg | minimum value of $\phi_A$ |
| $\phi_V^{min}$ | −8 | mmHg | minimum value of $\phi_V$ |
| $k_A$ | 0.3 | min$^{-1}$ | arterial contraction parameter eq. (21) |
| $k_V$ | 0.8 | min$^{-1}$ | venous contraction parameter eq. (22) |

Figure 19:
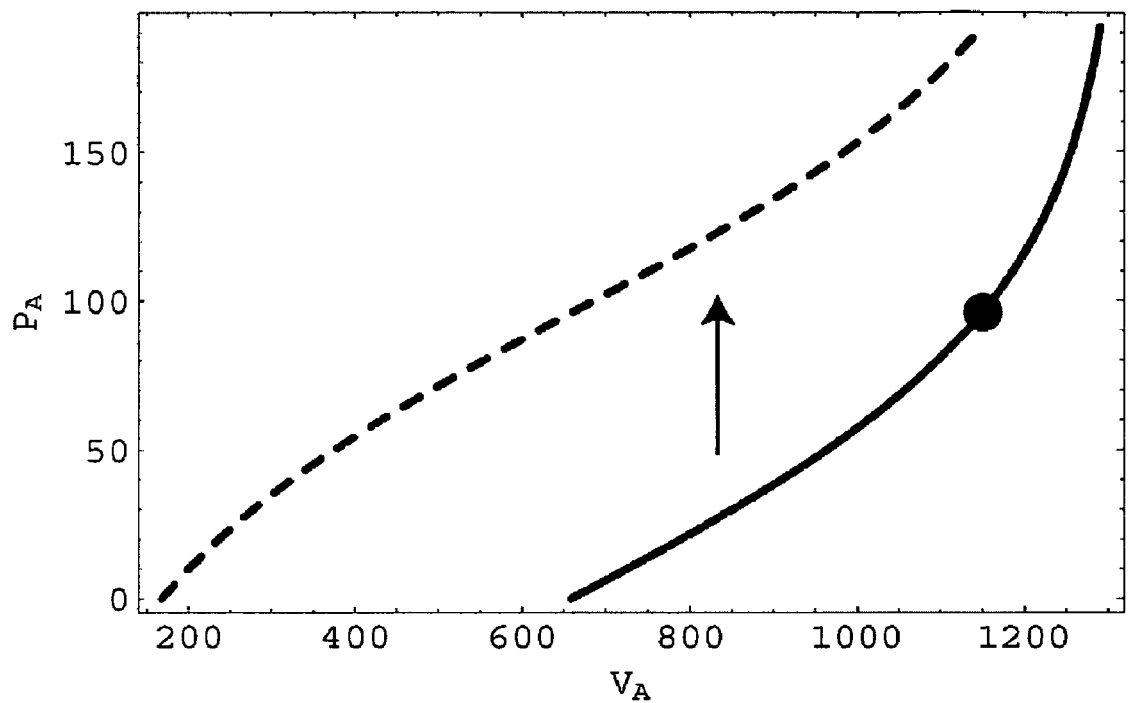
FIG. 19 illustrates one example of a chart of a calibrated pressure-volume relationship in arteries during a resting state (solid) and maximum smooth muscle contraction state (dashed)

Calibrated scale values for the parameters $r_A$, $r_V$, $V_V^{Max}$ and $V_V^{Max}$ calculated by imposing the constraints (150) to (153) are given in Table 1. A portion of the resulting pressure-volume relationship in the arteries is depicted in FIG. 19. As a function of arterial pressure $P_A$, the solid curve in FIG. 19 represents the pressure-volume relationship under resting conditions while the dashed curve shows the shift of this relationship under maximum smooth muscle contraction. The large dot indicates mean pressure and volume in the resting state and the arrow indicates the vertical shift associated with maximum smooth muscle contraction.

Cardiac arrest and mean filling pressure were simulated. When cardiac uptake and output were set to zero and all auto-regulatory mechanisms deactivated, both $P_A$ and $P_V$ were found to tend towards the same pressure of 6.94 mm Hg after about a minute. If the pressures generated by smooth muscle contraction ($\phi_A$ and $\phi_V$) are initially set equal to their maximum values and initial arterial and venous pressures are adjusted accordingly, the simulations return a value of about 23 mm Hg, or approximately 3.5 times normal.

Figure 20:
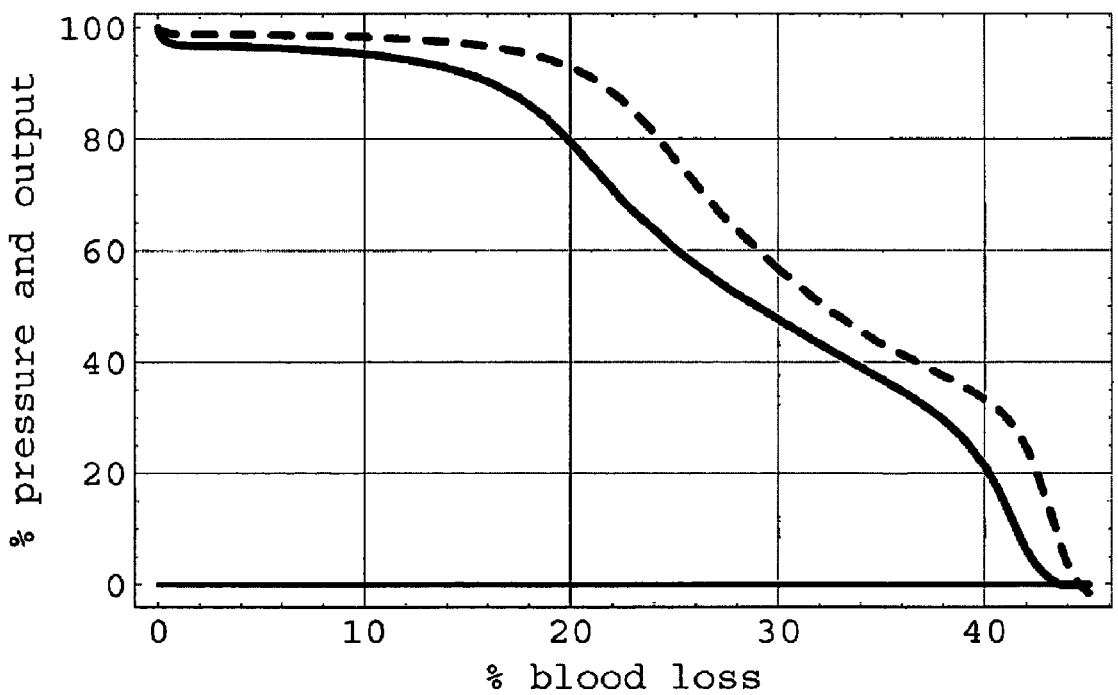
FIG. 20 illustrates one example of a chart of a percent arterial pressure (dashed) and cardiac output (solid) with respect to a percent blood loss due to hemorrhage.

Loss of blood volume by hemorrhage was also simulated. The results predicted by simulating a total blood loss of about 45 percent through hemorrhage with all regulatory mechanisms active are shown in FIG. 20. This figure depicts the relative change in arterial pressure and cardiac output over the course of the hemorrhage. Very little difference was noted in these simulations when the hemorrhage terms varied between arterial hemorrhage and venous hemorrhage.

Figure 21:
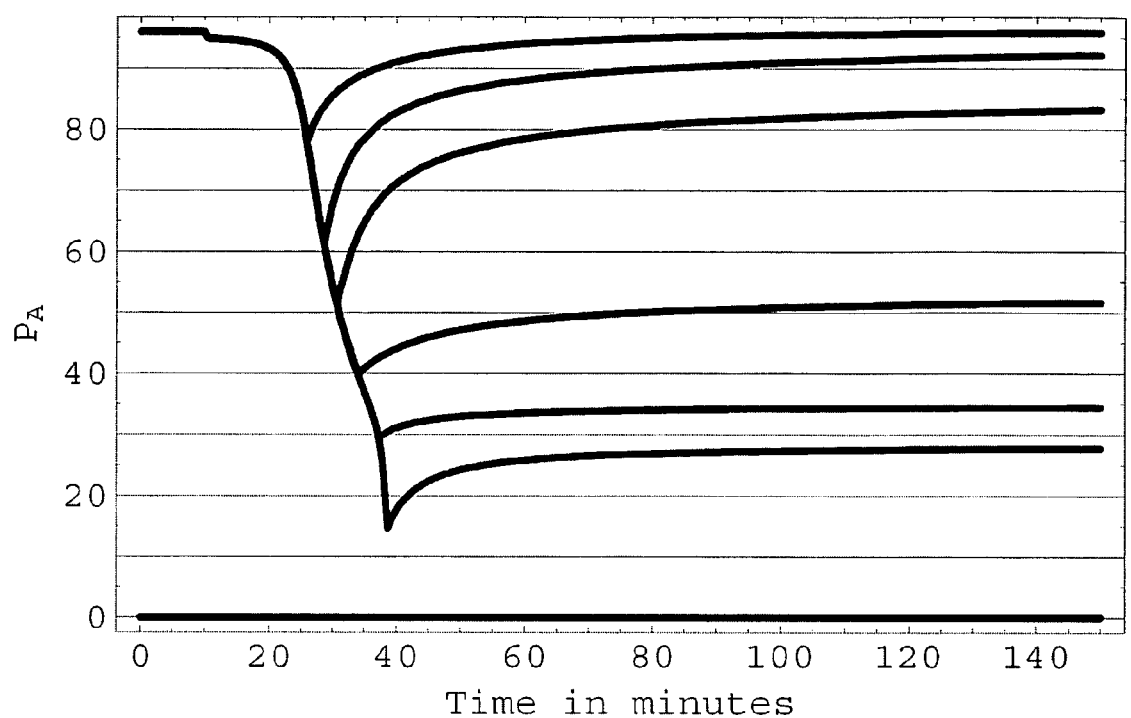
FIG. 21 illustrates one example of a chart of a predicted ability of arterial pressure to recover following various levels of blood loss due to hemorrhage.

Simulations were also conducted with lesser degrees of total blood loss to test the ability of the model to predict a recovery of arterial pressure once a hemorrhage stops. With the model's regulatory mechanisms active, the predicted behavior of arterial pressure during and after hemorrhages with total blood losses of 24, 28, 31, 36, 41, and 43 percent of total blood volume is shown in FIG. 21. FIG. 21 illustrates the predicted ability of arterial pressure to recover following various levels of blood loss due to hemorrhage. The resulting minimum arterial pressures as a result of these hemorrhages were predicted to be approximately 80, 60, 50, 40, 30, and 15 mm Hg, respectively. Recovery of arterial pressure after the hemorrhage ceases is predicted in the first three cases, whereas no evidence of recovery was seen in the last three cases before the simulation was terminated.

In the simulations of a hemorrhage of 10 percent of total blood volume at a rate consistent with FIG. 20, a drop of about 1.6 mm Hg in arterial pressure is predicted when all ANS mechanisms are active. With all ANS mechanisms deactivated, the predicted drop is about 61.6 mm Hg. The difference between these two cases is thus predicted to be about 60 mm Hg.

The present example is a simplified model having fewer compartments than the whole-body model of the embodiment described above, which includes sixteen distinct compartments, a left and right heart, and embeds the intracranial system in extensive whole-body physiology. However, despite the relative simplicity of the present example, it is robust and able to accurately represent the autonomic and central nervous system regulatory mechanisms that maintain arterial pressure, cardiac output, and cerebral blood flow in the face of both moderate and extreme stimuli. In this regard, it differs from earlier lumped-parameter models of the cardiovascular system.

Clinical data shows that cerebral blood flow, $Q_1$, is highly regulated and remains nearly constant for arterial pressures between about 60 mm Hg and about 150 mm Hg. This behavior is modeled in the present embodiment by a representation in which the mean cerebral blood flow, $\overline{Q}_1$, is multiplied by a logistic function depending on the deviation of the systemic indicative pressure $P_{AV}$ from its mean value. As the present example has no brain compartment, $P_{AV}$ acts as a surrogate for perfusion pressure in this expression. As depicted in FIG. 13, the model's representation for $Q_1$ remains nearly constant until indicative pressure drops below about 60 mm Hg. As venous pressure remains near zero, consistent with clinical observations, this threshold corresponds to an arterial pressure that is also near 60 mm Hg.

As in many lumped-parameter models, the non-cerebral blood flow $Q_2$ is assumed related to the pressure difference $P_{AV}$ through a resistance parameter $R_2$, whose inverse is the fluidity $Z_2$. However, $Z_2$ here is not assumed to be a constant parameter, as is often the case in other lumped-parameter models that linearize some or all of the governing differential equations for the pressure dynamics. Instead, it is a function of both pressures and time that involves not only the mean scale fluidity value $\overline{Z}_2$ but also logistic expressions representing the autonomic and central nervous system responses that regulate arterial pressure.

The factor ANSz in $Z_2$ has a logistic representation that depends on the difference between the arterial pressure $P_A$ and its mean value $\overline{P}_A$. This factor represents the direct regulation of arterial blood pressure by the autonomous nervous system (ANS) via the baroreceptors located in the walls of the carotid arteries and arch of the aorta. As depicted in FIG. 16, ANSz is less than one (vasoconstriction) when arterial pressure drops below its mean value. This factor now reduces the fluidity $Z_2$ (increases the resistance $R_2$) of non-cerebral flow and will cause arterial pressure to increase toward its normal mean value. Conversely, when arterial pressure rises above its mean value, ANSz is greater than one (vasodilation), and the fluidity $Z_2$ will be increased, causing arterial pressure to decrease toward its mean value. Since parasympathetic stimulation does not dilate the arterioles, the only dilation effect of this mechanism is an inhibition of the vasoconstrictor center. Therefore, the ANS vasodilation has been approximated here as one third of the full vasoconstriction capabilities. Further, the factor ANSz does not diminish to zero as arterial pressure drops. Thus, even though essential blood flow to preserve the integrity of the heart muscle itself has not been explicitly included in the non-cerebral flow $Q_2$, ample flow still remains available for the heart muscle when ANSz is at its minimum value.

The factor CNSz in $Z_2$ represents part of the ischemic response of the central nervous system (CNS), which is triggered by a significant reduction in cerebral blood flow. This factor models the severe vasoconstriction in the arterioles of the non-vital tissues that is triggered when cerebral blood flow drops to levels that can compromise essential brain functions. CNSz is represented by a logistic expression that depends on the deviation of $Q_1$ from its mean value $\overline{Q}_1$. As shown in FIG. 18, a significant decrease in $Q_1$ will induce a rapid decrease in the fluidity multiplier CNSz, sharply increasing the peripheral resistance of the non-cerebral circulation and promoting an increase of arterial pressure. In Guyton et al., this ischemic response has been termed a "last ditch stand" in the face of marginal cerebral blood flow. It should be noted from FIG. 18 that, as is the case with ANSz, the present representation for CNSz also does not diminish to zero as arterial pressure falls, but tends to a minimum level of about 0.1. Thus, even in the face of severely diminished arterial pressure, about 4 to 5 percent of the original cardiac output will still be available for the heart muscle itself.

Venous return and venous pressure are two of the major determinants of cardiac uptake, and hence cardiac output. If either is allowed to drop significantly, cardiac output will diminish. In the present embodiment, the representation for cardiac uptake explicitly involves the venous return. In particular, cardiac uptake is defined as the venous return times a regulatory multiplier M The effect of central venous pressure on cardiac uptake enters through this regulatory multiplier, which also includes factors that model the regulation of cardiac output by the nervous system.

In the current embodiment, venous pressure affects cardiac output via a mechanism represented by the factor OVP (output versus pressure) in the cardiac uptake multiplier. The logistic OVP representation models the change in stroke volume associated with a change in central venous pressure. This interpretation follows from the fact that when both of the nervous system regulatory factors in Mare set to unity, cardiac output is not only a multiple of venous return, but the value of this multiple is determined entirely by central venous pressure.

The factor ANSo in M is associated with the autonomic nervous system. It models the mechanism that causes the heart rate to increase (sympathetic stimulation) when arterial pressure drops below its mean value and decrease (parasympathetic stimulation) when arterial pressure rises above this mean value. The logistic transition portion of ANSo is steepest at the mean value of arterial pressure. Consequently, this regulatory mechanism operates most effectively near mean arterial pressures. The factor CNSo in the multiplier M is associated with the ischemic response that produces a severe change in heart rate when triggered by significant reductions in the cerebral blood flow Q1. The representations for both ANSo and CNSo in the present example involve logistic functions.

While the autonomic responses modeled by ANSz and ANSo will aid in returning arterial pressure toward its normal mean value, they may not, by themselves, ensure that arterial pressure actually returns to this normal mean value. This is because interactions between mechanisms can reduce the overall effect of the autonomic responses. For example, an increase in cardiac activity in response to the ANSo mechanism will temporarily increase arterial pressure through greater cardiac output, but it will also decrease venous pressure. This, in turn, will reduce the over-all effect of the ANS response as decreased venous pressure will now cause a drop in cardiac uptake and output. Likewise, an increase in systemic resistance via the ANSz mechanism only ensures a greater systemic perfusion pressure. While this will most likely entail an increase in arterial pressure it may also result in a decrease in venous pressure, and again the over-all effect will be reduced. An additional ANS regulatory mechanism may therefore be included in the model to ensure that arterial pressure returns to its initial mean value under a wide range of stimuli.

Smooth muscle contraction in the walls of the large vessels provides this further mechanism by which the ANS regulates arterial pressure and cardiac output. If arterial pressure drops, smooth muscle contraction in the arteries tends to return arterial pressure back to normal. In addition, contraction in the large veins increases cardiac output via the OVP mechanism. This reaction is incorporated into the current embodiment by defining a new form of the pressure-volume relationship in a compliant vessel with smooth muscle contraction. This relationship gives the effect of smooth muscle contraction on the pressure, volume, and compliance of the large vessels. At a constant pressure, smooth muscle contraction decreases vessel volume, while smooth muscle contraction increases pressure at a constant volume. Basic assumptions now allow compartmental volumes to be represented by a logistic function involving maximum compartmental volumes, compartmental and ambient pressures, and a pressure increment $\phi$ that reflects the shift of the pressure-volume curve to the right during smooth muscle contraction. In this representation, maximum compliance is achieved when the interior pressure P is equal to the sum of the two external pressures $\phi$ and P*.

In the present embodiment, differentiating the pressure-volume relationship that results from including the effects of smooth muscle contraction produces an expression with an active compliance parameter that depends on maximum compartment volume, compartmental and ambient pressures, and the contraction pressure increment $\phi$. Unlike prior models, the active compliance in this expression multiplies a time derivative that includes the ambient pressure P* and pressure increment $\phi$ as well as the compartmental pressure P. If the ambient pressure is a constant and there is also no change in smooth muscle contraction, this expression reduces to the usual form. In this case, the active compliance becomes a traditional compliance, and this fact simplifies parameter calibration. It is interesting to note that the resulting calibrated pressure-volume curves in FIG. 19 modeled according to the present embodiment correspond favorably to data collected by Suga et al. in "Instantaneous Pressure-Volume Relationships and Their Ratio in the Excised, Supported Canine Left Ventricle," *Circulation Research* 35 (1974) pp 117-126, which is incorporated herein by reference in its entirety, for actual canine left ventricle pressure-volume relationships.

To test the ability of the present embodiment to accurately represent the autonomic and nervous system regulatory mechanisms that maintain arterial pressure, cardiac output, and cerebral blood flow, two pathological situations were simulated using the example model of FIG. 12 and the results compared to clinical observations. In the first of these, cardiac arrest was simulated in the model by setting cardiac uptake and output to zero and deactivating all regulatory mechanisms. Within a minute, both $P_A$ and $P_V$ in the simulation tended to the mean circulatory filling pressure. From Rothe, "Mean Circulatory Filling Pressure: Its Meaning and Measurement," *J. Appl. Physiol.* 74 (1993) pp. 499-509, which is incorporated herein by reference in its entirety, the clinical value of the normal mean circulatory filling pressure is about 7 mm Hg. Our simulations return a value of about 6.94 mm Hg. If the pressures generated by smooth muscle contraction ($\phi_A$ and $\phi_V$) are initially set equal to their maximum values and initial arterial and venous pressures are adjusted accordingly, simulations return a value of about 23 mm Hg, or about 3.5 times normal. This is within the range of about 2 to 4 times normal cited in Pang et al., "Peripheral Circulatory Control of Preload-Afterload Mismatch with Angiotensin in Dogs," *Br. J. Pharmac.* 89 (1986) pp. 389-394 and Alexander, "The Systemic Circulation," *Annual Rev. of Phys.* 25 (1963) pp. 213-234, each of which is incorporated herein by reference in their entirety.

The effects of regulation were particularly apparent in simulations of the second pathological situation, where hypovolemic shock due to various levels of blood loss through hemorrhage was modeled. The first simulation in this set was based on a clinical situation involving a 45 percent blood loss over the course of 30 minutes. In particular, the modeled response displayed in FIG. 20 shows very stable pressure and cardiac output over the first 10 percent blood loss, and the relative arterial pressure stays above relative output during the entire course of the hemorrhage. Beyond about 30 percent blood loss, a second arterial plateau is noted in FIG. 20. This important feature is due to the triggering of the ischemic reflexes that act to maintain blood supply to the brain in the face of low perfusion pressure. At about 45 percent blood loss, simulation results show cardiac pressure and cardiac output dropping quickly to zero. This behavior is in good agreement with the measured data on heart rate and mean blood pressure given in Opdyke, "Circulatory Effect of Partial Cerebral Ischemia," *Am. J. Physiol.* 143 (1945) pp. 247-253, which is incorporated herein by reference in its entirety, for the deterioration of the circulation in shock, although a small rise in the measured data due to the ischemic response prior to a sharp decline occurs in place of the plateau in the predicted results. However, the simulation's predictions, including the plateau, for the relative change in arterial pressure and cardiac output over the course of the simulated hemorrhage with all regulatory mechanisms active are in near perfect agreement with the behavior given in Guyton et al. for this hemorrhage.

As noted above, the value of the cardiac uptake multiplier M in the simulation of the 45 percent blood volume loss hemorrhage was initially set to unity, consistent with the Frank-Starling mechanism of the heart in which cardiac uptake equals venous return. The cardiac uptake multiplier was found to remain in the range $0.95<M<1.05$ over the entire course of the simulation, so deviations from the Frank-Starling "law of the heart" did not exceed about 5 percent. However, a separate simulation determined that if M is fixed at unity to strictly enforce cardiac uptake equaling venous return for all time, a hemorrhage resulting in a blood loss that exceeds about 12 percent of blood volume will cause death, even when all other regulation mechanisms are intact. Therefore, while the Frank-Starling "law" is relatively accurate, simulations suggest that small deviations apparently must be allowed for the maintenance of cardiac output and arterial pressure.

A second group of hemorrhage simulations tested the ability of the model to predict recovery from various levels of blood loss as well as the critical value of blood loss that determines if the hypovolemic shock caused by the hemorrhage will be non-progressive or progressive. Predictions of this group of simulations were then compared to the measured results presented in Guyton et al., "Dynamics of the Heart in Shock," Fed. Proc. 20, Suppl. 9 (1961) pp. 51-60; Walcott, "Blood Volume in Experimental Hemorrhagic Shock," Am. J. Physiol. 143 (1945) pp 247-253; Noble et al., "Blood Volume in Clinical Shock: The Extent and Cause of Blood of Volume Reduction in Traumatic Hemorrhage and Burn Shock," J. Clin. Invest. 25 (1946) pp. 172-183; and Williams et al., Hematology, $3^{rd}$ Ed. (1983), each of which are incorporated herein by reference in their entirety. As can be seen from FIG. 21, with all regulatory mechanisms active a fairly rapid and complete recovery is predicted by the simulations for arterial pressures that do not fall below about 50 mm Hg as a result of the hemorrhage. Conversely, for pressures that fall to about 40 mm Hg or less, there is little recovery made. Since the present embodiment is capable of functioning indefinitely at low levels of blood supply to the non-vital tissues, progressive shock due to vascular and cardiac deterioration is beyond the capabilities of the model. However, if arterial pressure remains low in a simulation with no evidence of recovery apparent, it is likely that a progressive shock will occur. Unfortunately, a sharp critical value for the minimum arterial pressure level cannot be consistently predicted by the current simulations. In the case of minimum arterial pressures between about 40 and about 50 mm Hg, progression or recovery will most likely depend on long term mechanisms such as the renal system, sodium chloride production, and fluid intake which are not represented in the model.

Results from the second group of hemorrhage simulations are in close agreement with the measured results in Guyton, Walcott, Noble et al., and Williams et al. In Guyton, the "thin line of balance between progression of shock and progression of recovery" is placed at about 47 mm Hg. The measured data in Walcott, Noble et al., and Williams et al. characterizes progression or recovery in terms of the percentage of total blood volume lost rather than the value of arterial pressure. In the experiments of Walcott, recovery following hemorrhage occurred for a mean loss of about 34.5 percent of total blood volume while an about 43 percent blood loss was progressive. In Noble et al., and Williams et al., clinical signs of progressive shock occur with a blood loss in the range of about 30 to about 40 percent of total blood volume. Consistent with this measured data, in the present simulation an about 30 percent blood loss results in a minimum arterial pressure of about 54 mm Hg, and from FIG. 21 recovery is predicted. An about 40 percent blood loss results in a minimum arterial pressure of about 32 mm Hg, and from FIG. 21 progression of shock is predicted.

The importance of the regulatory mechanisms in the modeled hemorrhagic situations can be judged from several factors. It is noted in Guyton et al. that with the sympathetic reflexes inoperative, recovery does not occur if only about 15 to 20 percent of blood volume is removed over an about 30 minute period. By contrast, the experimental results Guyton et al. show that a blood volume loss of between about 30 to about 40 percent can be sustained when these reflexes are intact and operative. Predictions from the second group of hemorrhage simulations agree with these clinical findings. In particular, in the simulations, FIG. 21 shows that with the regulatory reflexes intact, the model predicts that recovery can occur after about 30 to about 40 percent blood volume loss. On the other hand, when the ANS mechanisms are deactivated, the simulations show that recovery is not indicated at about 15 percent blood volume loss. Of the ANS mechanisms, the regulation of arterial pressure by smooth muscle contraction appears to make the most difference with regards to survival following hemorrhage. With smooth muscle contraction active but the ANSo and ANSz mechanisms deactivated, cardiac output and arterial pressure fall to zero at about a 40 percent blood volume loss (as opposed to about 45 percent with all three mechanisms activated). Conversely, if ANSz and ANSo are both active but there is no smooth muscle contraction, cardiac output and arterial pressure fall to zero at about an about 18 percent blood volume loss (as opposed to about 15 percent with all three mechanisms deactivated). Physiologically, this implies that increased heart rate and increased peripheral resistance aid in immediate short-term arterial blood pressure maintenance but do not act as survival mechanisms. Recovery from a significant but sub-critical hemorrhage is primarily due to regulation of arterial pressure by smooth muscle contraction as well as the ischemic reflexes of the central nervous system.

To insure that the mathematical representations in a model of the embodiment accurately capture the overall effect of the ANS reflex mechanisms, additional simulations involving an about 10 percent hemorrhage of total blood volume were performed. These simulations predict a difference of about 60 mm Hg between the case when all ANS mechanisms are active and the case when all ANS mechanism are deactivated. Experiments detailed in Hosomi et al., "Sinovagal Interaction in Arterial Pressure Restoration After 10% Hemorrhage," Am. J. Physiol. Regul. Integr. Comp. Physiol. 237 (1979) pp. R203-R209, which is incorporated herein by reference in its entirety, determined that following an about 10 percent quick hemorrhage arterial pressure drops about 7.2 mm Hg with all regulatory mechanisms intact and about 67.6 mm Hg with blocked reflexes. Therefore, the data shows that these regulatory mechanisms act to reduce the arterial pressure drop following the hemorrhage by about 60.4 mm Hg. The model predictions for this case are thus in excellent agreement with measured data indicating that the ANS reflex mechanisms have been consistently included in the model and are realistically represented by their logistic mathematical expressions.

The methodologies related to this embodiment may be implemented using a machine, such as a computer. As discussed above with respect to the whole-body model embodiment, FIG. 6 illustrates an example computing environment for a system and/or method of the present disclosure. It will be understood by those skilled in the art that instructions for performing methodologies according the present embodiment may also be implemented in a similar fashion using such a computing environment. An additional embodiment of a machine is provided below with respect to FIG. 22.

In one aspect, a model of the present disclosure may be implemented by a medical device for monitoring a circulatory system. In one example, a medical device may utilize the modeled values of a circulatory system provided by a methodology of the present disclosure to predict circulatory system behavior. In another example, a medical device may utilize modeled values in conjunction with actual measured circulatory system values for providing appropriate care to a patient. A modeled circulatory system value may be compared to a corresponding circulatory system value that has been measured and used in monitoring a circulatory system of a subject.

Figure 22:
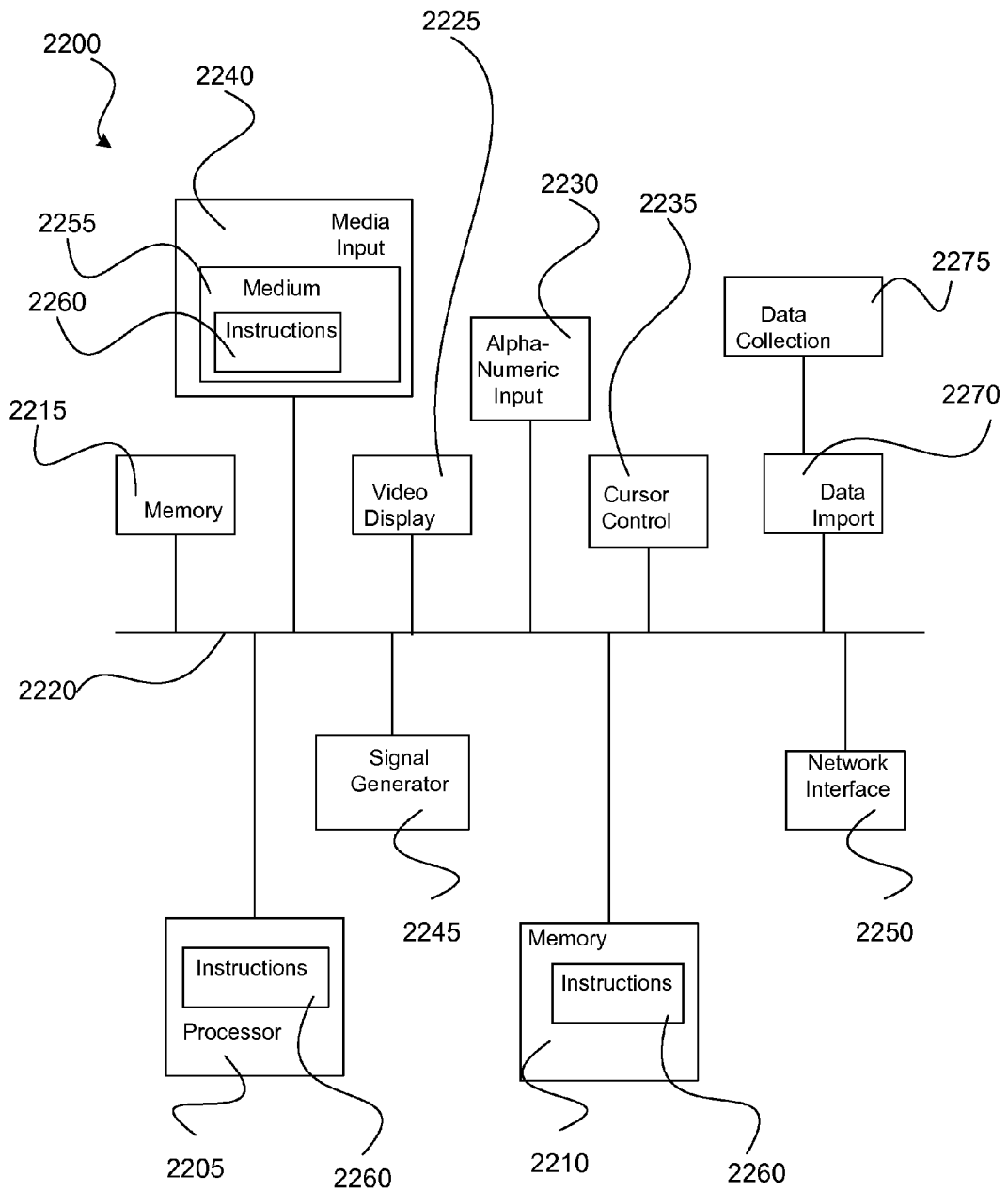
FIG. 22 illustrates one example of a simplified schematic of a computer system including one embodiment of the present invention.

FIG. 22 shows a diagrammatic representation of one embodiment of a machine in the exemplary form of a computer system 2200 within which a set of instructions, for causing the machine to perform any one of the methodologies of the present invention, may be executed. In alternative embodiments, the machine may comprise a network router, a network switch, a network bridge, Personal Digital Assistant (PDA), a cellular telephone, a web appliance, a medical device, or any machine capable of executing a sequence of instructions that specify actions to be taken by that machine. Example medical devices may include, but are not limited to, an electrocardiograph device, a circulatory pressure monitoring device, a sphygmomanometer, and any combinations thereof.

The computer system 2200 includes a processor 2205, a main memory 2210 and a static memory 2215, which communicate with each other via a bus 2220. Computer system 2200 may further include a video display unit 2225 (e.g., a liquid crystal display (LCD) or a cathode ray tube (CRT)). Computer system 2200 may also include an alpha-numeric input device 2230 (e.g., a keyboard), a cursor control device 2235 (e.g., a mouse), a media input device 2240 (e.g., a disk drive, a universal serial bus (USB) port, etc.), a signal generation device 2245 (e.g., a speaker), and/or a network interface device 2250.

Media input device 2240 includes a machine-readable medium 2255 on which is stored a set of instructions (i.e., software) 2260 embodying any one, or all, of the embodiments of the present invention. Software 2260 is also shown to reside, completely or at least partially, within the main memory 2210 and/or within the processor 2205. Software 2260 may further be transmitted or received via the network interface device 2250. For the purposes of this specification, the term "machine-readable medium" shall be taken to include any medium that is capable of storing or encoding a sequence of instructions for execution by the machine and that causes the machine to perform any one of the methodologies of the present invention. The term "machine-readable medium" shall accordingly be taken to include, but not be limited to, solid-state memories (e.g., random access memory (RAM), flash memory, etc.), optical and magnetic disks, and carrier wave signals.

Computer system 2200 may also include a circulatory system data import device 2270 for allowing measured data from a subject to be utilized by set of instructions 2260. Circulatory system data import device 2270 may be connected to a circulatory system data collection device 2275.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of modeling a circulatory system using a programmed computer, the method comprising:
    providing a circulatory system model in the computer, the model including one or more time-dependent pressure functions, each of said one or more time-dependent pressure functions representing a pressure in a portion of the circulatory system;
    using a logistic function in the computer to represent a regulatory mechanism parameter, said regulatory mechanism parameter representing a regulatory mechanism having an impact on circulatory system function;
    dividing the circulatory system into a plurality of compartments and a heart pump, said plurality of compartments representing a portion of the circulatory system, said heart pump interacting with at least one of said plurality of compartments;
    assigning, using the computer, one of said one or more time-dependent pressure functions to each of said plurality of compartments;
    using a smooth muscle contraction parameter, said smooth muscle contraction parameter representing an autonomic nervous system effect on smooth muscle contraction in a wall of one of said plurality of compartments, wherein said smooth muscle contraction parameter is represented according to the following equation:

$$\dot{V} = C \cdot (\dot{P} - (\dot{\phi} + \dot{P}^*))$$

wherein $\dot{V}$ is a time derivative of a volume of said one of said plurality of compartments, $\dot{P}$ is a time derivative of the pressure inside said one of said plurality of compartments, $\dot{\phi}$ is a time derivative of said smooth muscle contraction parameter, $\dot{P}^*$ is a time derivative of the pressure outside of said one of said plurality of compartments, and C is an active compliance defined according to the following equation:

$$C = \frac{rV^{Max}e^{-r(P-(\phi+P^*))}}{(1+e^{-r(P-(\phi+P^*))})^2}$$

wherein $r > 0$, $V^{Max}$ is a maximum volume of said one of said plurality of compartments, P is the pressure inside said one of said plurality of compartments, P* is the pressure outside said one of said plurality of compartments, and $\phi$ is said smooth muscle contraction parameter; and
    solving, using the computer, one or more equations for said one or more time-dependent pressure functions and said logistic function to determine a circulatory system dynamic.

2. A method according to claim 1, wherein said dividing step divides said circulatory system into a set of compartments consisting of an arterial compartment and a venous compartment, and a heart pump.

3. A method according to claim 1, wherein said dividing step divides said circulatory system into a set of compartments comprising of an arterial compartment and a venous compartment, and a heart pump.

4. A method according to claim 3, further comprising using a logistic function to represent a cerebral blood flow parameter.

5. A method according to claim 4, wherein said using of a logistic function to represent said cerebral blood flow parameter comprises representing said cerebral blood flow parameter according to the following logistic function:

$$Q_1 = L_{inc}(P_{AV} - \overline{P}_{AV}, 0.15, 1.0001, 0) \cdot \overline{Q}_1$$

wherein $Q_1$ is said cerebral blood flow parameter, $P_{AV}$ is a pressure difference $P_A - P_V$, wherein $P_A$ is said time-dependent pressure function for said arterial compartment and $P_V$ is said time-dependent pressure function for said venous compartment, $\overline{P}_{AV}$ is a mean systemic indicative pressure, $\overline{Q}_1$ is a mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, $r > 0$, $-\infty < x < \infty$, and $\min < L_{inc}$.

6. A method according to claim 3, further comprising using a logistic function to represent an output versus pressure parameter, said output versus pressure parameter representing an effect of venous pressure on cardiac uptake.

7. A method according to claim 6, wherein said using of a logistic function to represent an output versus pressure parameter comprises representing said output versus pressure parameter according to the following logistic function:

$$OVP(P_V) = L_{inc}(P_V - \overline{P}_V, 0.5, 2.5, 0)$$

wherein OVP is said output versus pressure parameter, $P_V$ is said time-dependent pressure function for said venous compartment, $\overline{P}_V$ is the mean systemic venous pressure, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, $r > 0$, $-\infty < x < \infty$, and $\min < L_{inc}$.

8. A method according to claim 3, wherein said regulatory mechanism parameter represents an autonomic nervous system effect on cardiac output according to the following equation:

$$ANSo = L_{dec}(P_A - \overline{P}_A, 0.1, 2, 0)$$

wherein $ANS_o$ is said regulatory mechanism parameter representing said autonomic nervous system effect on cardiac output, $P_A$ is said time-dependent pressure function for said arterial compartment, $\overline{P}_A$ is an initial mean arterial pressure, and $L_{dec}$ is a decreasing logistic function represented by the following equation:

$$L_{dec}(x, r, \max, \min) = \max + \frac{\min - \max}{1 + \frac{1 - \min}{\max - 1} e^{-rx}}$$

wherein max is a maximum value for x, min is a minimum value for x, $r > 0$, $-\infty < x < \infty$, and $L_{dec} < \max$.

9. A method according to claim 3, wherein said regulatory mechanism parameter represents an autonomic nervous system effect on non-cerebral blood flow according to the following equation:

$$ANSz = L_{inc}(P_A - \overline{P}_A, 0.3, 1.1, 0.7)$$

wherein ANSz is said regulatory mechanism parameter representing said autonomic nervous system effect on non-cerebral blood flow, $P_A$ is said time-dependent pressure function for said arterial compartment, $\overline{P}_A$ is an initial mean arterial pressure, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, $r > 0$, $-\infty < x < \infty$, and $\min < L_{inc}$.

10. A method according to claim 3, wherein said regulatory mechanism parameter represents a central nervous system effect on cardiac output according to the following equation:

$$CNSo = L_{dec}(Q_1 - \overline{Q}_1, 0.01, 5, 0.9)$$

wherein $Q_1$ is cerebral blood flow, $\overline{Q}_1$ is mean cerebral blood flow, and $L_{dec}$ is a decreasing logistic function represented by the following equation:

$$L_{dec}(x, r, \max, \min) = \max + \frac{\min - \max}{1 + \frac{1 - \min}{\max - 1} e^{-rx}}$$

wherein max is a maximum value for x, min is a minimum value for x, $r > 0$, $-\infty < x <$, and $L_{dec} < \max$.

11. A method according to claim 3, wherein said regulatory mechanism parameter represents a central nervous system effects on non-cerebral blood flow according to the following equation:

$$CNSz = L_{inc}(Q_1 - \overline{Q}_1, 0.01, 1.01, 0.1)$$

wherein $Q_1$ is cerebral blood flow, $\overline{Q}_1$ is mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, $r > 0$, $-\infty < x < \infty$, and $\min < L_{inc}$.

12. A medical device for monitoring a circulatory, system, the medical device configured to perform a method according to claim 1.

13. A method of monitoring a circulatory system, the method comprising:
    measuring a desired circulatory system value; and
    comparing said desired circulatory system value to a corresponding circulatory system value calculated using a method according to claim 1.

14. A non-transitory computer readable medium containing computer executable instructions implementing a method of modeling a circulatory system, the instructions comprising:
- a first set of instructions for providing a circulatory system model including one or more time-dependent pressure functions, each of said one or more time-dependent pressure functions representing a pressure of a portion of the circulatory system;
- a second set of instructions for using a logistic function to represent a regulatory mechanism parameter, said regulatory mechanism parameter representing a regulatory mechanism having an impact on circulatory system function;
- a third set of instructions for solving one or more equations for said one or more time-dependent pressure functions and said logistic function to determine a circulatory system dynamic;
- a fourth set of instructions for dividing the circulatory system into a plurality of compartments and a heart pump, said plurality of compartments representing a portion of the circulatory system, said heart pump interacting with at least one of said plurality of compartments;
- a fifth set of instructions for assigning a time-dependent pressure function to each of said plurality of compartments; and
- a sixth set of instructions for using a smooth muscle contraction parameter, said smooth muscle contraction parameter representing an autonomic nervous system effect on smooth muscle contraction in a wall of one of said plurality of compartments, wherein said smooth muscle contraction parameter is represented according to the following equation:

$$\dot{V} = C \cdot (\dot{P}(\dot{\phi} + \dot{P}^*))$$

wherein $\dot{V}$ is a time derivative of a volume of said one of said plurality of compartments, $\dot{P}$ is a time derivative of the pressure inside said one of said plurality of compartments, $\dot{\phi}$ is a time derivative of said smooth muscle contraction parameter, $\dot{P}^*$ is a time derivative of the pressure outside of said one of said plurality of compartments, and C is an active compliance defined according to the following equation:

$$C = \frac{rV^{Max} e^{-r(P-(\phi+P^*))}}{(1 + e^{-r(P-(\phi+P^*))})^2}$$

wherein r>0, $V^{Max}$ is a maximum volume of said one of said plurality of compartments, P is the pressure inside said one of said plurality of compartments, P* is the pressure outside said one of said plurality of compartments, and $\phi$ is said smooth muscle contraction parameter.

15. A computer readable medium according to claim 14, wherein said fourth set of instructions comprises a seventh set of instructions for dividing the circulatory system into an arterial compartment and a venous compartment.

16. A computer readable medium according to claim 15, further comprising a eighth set of instructions for using a logistic function to represent a cerebral blood flow parameter.

17. A computer readable medium according to claim 16, wherein said eighth set of instructions comprises a ninth set of instructions for representing said cerebral blood flow parameter according to the following logistic function:

$$Q_1 = L_{inc}(P_{AV}, \overline{P}_{AV}, 0.15, 1.0001, 0)\overline{Q}_1$$

wherein $Q_1$ is said cerebral blood flow parameter, $P_{AV}$ is a pressure difference $P_A - P_V$, wherein $P_A$ is said time-dependent pressure function for said arterial compartment and $P_V$ is said time-dependent pressure function for said venous compartment, $\overline{P}_{AV}$ is a mean systemic indicative pressure, $\overline{Q}_1$ is a mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, r>0, $-\infty < x < \infty$, and min<$L_{inc}$.

18. A computer readable medium according to claim 15, further comprising a tenth set of instructions for using a logistic function to represent an output versus pressure parameter, said output versus pressure parameter representing an effect of venous pressure on cardiac uptake.

19. A computer readable medium according to claim 18, wherein said tenth set of instructions comprises a eleventh set of instructions for representing said output versus pressure parameter according to the following logistic function:

$$OVP(P_V) = L_{inc}(P_V - \overline{P}_V, 0.5, 2.5, 0)$$

wherein OVP is said output versus pressure parameter, $P_V$ is said time-dependent pressure function for said venous compartment, $\overline{P}_V$ is the mean systemic venous pressure, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, r>0, $-\infty < x < \infty$, and min<$L_{inc}$.

20. A computer readable medium according to claim 16, wherein said second set of instructions comprises a twelfth set of instructions for representing said regulatory mechanism parameter as an autonomic nervous system effect on cardiac output according to the following equation:

$$ANS_o = L_{dec}(P_A - \overline{P}_A, 0.1, 2, 0)$$

wherein $ANS_o$ is said regulatory mechanism parameter representing said autonomic nervous system effect on cardiac output, $P_A$ is said time-dependent pressure function for said arterial compartment, $\overline{P}_A$ is an initial mean arterial pressure, and $L_{dec}$ is a decreasing logistic function represented by the following equation:

$$L_{dec}(x, r, \max, \min) = \max + \frac{\min - \max}{1 + \frac{1 - \min}{\max - 1} e^{-rx}}$$

wherein max is a maximum value for x, min is a minimum value for x, r>0, $-\infty < x < \infty$, and $L_{dec}$<max.

21. A computer readable medium according to claim 16, wherein said second set of instructions comprises a thirteenth set of instructions for representing said regulatory mechanism parameter as an autonomic nervous system effect on non-cerebral blood flow according to the following equation:

$ANSz = L_{inc}(P_A - \overline{P}_A, 0.3, 1.1, 0.7)$ wherein ANSz is said regulatory mechanism parameter representing said autonomic nervous system effect on non-cerebral blood flow, $P_A$ is said time-dependent pressure function for said arterial compartment, $\overline{P}_A$ is an initial mean arterial pressure, and $L_{inc}$ is an increasing logistic function represented by the following equation:

$$L_{inc}(x, r, \max, \min) = \max + \frac{\min - \max}{1 + \frac{1 - \min}{\max - 1}e^{rx}}$$

wherein max is a maximum value for x, min is a minimum value for x, $r>0$, $-\infty < x < \infty$, and $\min < L_{inc}$.

22. A computer readable medium according to claim 16, wherein said second set of instructions comprises a fourteenth set of instructions for representing said regulatory mechanism parameter as a central nervous system effects on cardiac output according to the following equation:

$CNSo = L_{dec}(Q_1 - \overline{Q}_1, 0.01, 5, 0.9)$ wherein $Q_1$ is cerebral blood flow, $\overline{Q}_1$ is mean cerebral blood flow, and $L_{dec}$ is a decreasing logistic function represented by the following equation:

$$L_{dec}(x, r, \max, \min) = \max + \frac{\min - \max}{1 + \frac{1 - \min}{\max - 1}e^{-rx}}$$

wherein max is a maximum value for x, min is a minimum value for x, $r>0$, $-\infty < x < \infty$, and $L_{dec} < \max$.

23. A computer readable medium according to claim 16, wherein said second set of instructions comprises a fifteenth set of instructions for representing said regulatory mechanism parameter as a central nervous system effects on non-cerebral blood flow according to the following equation:

$CNSz = L_{inc}(Q_1 - \overline{Q}_1, 0.01, 1.01, 0.1)$ wherein $Q_1$ is cerebral blood flow, $\overline{Q}_1$ is mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1}e^{rx}}$$

wherein max is a maximum value for x, min is a minimum value for x, $r>0$, $-\infty < x < \infty$, and $\min < L_{inc}$.

24. A method of modeling a pressure and volume relationship in a compliant vessel using a programmed computer, the method comprising:

defining a first parameter as a change in pressure within the vessel using the computer, said change in pressure being due to a contraction of smooth muscles of a wall of the vessel;

defining a second parameter as an active compliance for the vessel using the computer, said active compliance varying with internal pressure, external pressure, and said first parameter, wherein said second parameter is defined according to the following equation:

$$C = \frac{rV^{Max}e^{-r(P-(\phi+P^*))}}{(1 + e^{-r(P-(\phi+P^*))})^2}$$

wherein C is said second parameter, $r>0$, $V^{Max}$ is a maximum volume of said vessel, P is the pressure inside said vessel, $P^*$ is the pressure outside said vessel, and $\phi$ is said first parameter; and relating, using the computer, said first parameter and said second parameter via a differential equation, wherein said relating step comprises relating said first parameter and said second parameter according to the following equation:

$\dot{V} = C \cdot (\dot{P} - (\dot{\phi} = \dot{P}^*))$ wherein $\dot{V}$ is a time derivative of a volume of said vessel, $\dot{P}$ is a time derivative of the pressure inside said vessel, $\dot{\phi}$ is a time derivative of said first parameter, $\dot{P}^*$ is a time derivative of the pressure outside of said vessel, and C is said second parameter.

25. A method according to claim 24, further comprising using said first parameter and said second parameter in modeling a circulatory system.

26. A non-transitory computer readable storage medium containing computer executable instructions implementing a method of modeling a pressure and volume relationship in a compliant vessel, the instructions comprising:

a first set of instructions for defining a first parameter as a change in pressure within the vessel, said change in pressure being due to a contraction of smooth muscles of a wall of the vessel;

a second set of instructions for defining a second parameter as an active compliance for the vessel, said active compliance varying with internal pressure, external pressure, and said first parameter, wherein said second set of instructions comprises a set of instructions for defining said second parameter according to the following equation:

$$C = \frac{rV^{Max}e^{-r(P-(\phi+P^*))}}{(1 + e^{-r(P-(\phi+P^*))})^2}$$

wherein C is said second parameter, $r>0$, $V^{Max}$ is a maximum volume of said vessel, P is the pressure inside said vessel, $P^*$ is the pressure outside said vessel, and $\phi$ is said first parameter; and a third set of instructions for relating said first parameter and said second parameter via a differential equation, wherein said third set of instructions comprises a set of instructions for relating said first parameter and said second parameter according to the following equation:

$\dot{V} = C \cdot (\dot{P} - (\dot{\phi} + \dot{P}^*))$ wherein $\dot{V}$ is a time derivative of a volume of said vessel, $\dot{P}$ is a time derivative of the pressure inside said vessel, $\dot{\phi}$ is a time derivative of said first parameter, $\dot{P}^*$ is a time derivative of the pressure outside of said vessel, and C is said second parameter.

27. A computer readable medium according to claim 26, further comprising a sixth set of instructions for using said first parameter and said second parameter in modeling a circulatory system.

28. A method of modeling a circulatory system using a programmed computer, the method comprising:
  providing a circulatory system model in the computer, the model including one or more time-dependent pressure functions, each of said one or more time-dependent pressure functions representing a pressure in a portion of the circulatory system;
  using a logistic function in the computer to represent a regulatory mechanism parameter, said regulatory mechanism parameter representing a regulatory mechanism having an impact on circulatory system function, said using a logistic function including using a logistic function to represent a cerebral blood flow parameter according to the following logistic function:

$$Q_1 = L_{inc}(P_{AV} - \overline{P}_{AV}, 0.15, 1.0001, 0) \cdot \overline{Q}_1$$

wherein $Q_1$ is said cerebral blood flow parameter, $P_{AV}$ is a pressure difference $P_A - P_V$, wherein $P_A$ is said time-dependent pressure function for said arterial compartment and $P_V$ is said time-dependent pressure function for said venous compartment, $\overline{P}_{AV}$ is a mean systemic indicative pressure, $\overline{Q}_1$ is a mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, $r > 0$, $-\infty < x < \infty$, and $\min < L_{inc}$;
  dividing the circulatory system into a plurality of compartments and a heart pump, said plurality of compartments representing a portion of the circulatory system, said heart pump interacting with at least one of said plurality of compartments, wherein said dividing step divides said circulatory system into a set of compartments comprising of an arterial compartment and a venous compartment, and a heart pump;
  assigning, using the computer, one of said one or more time-dependent pressure functions to each of said plurality of compartments;
  using a smooth muscle contraction parameter, said smooth muscle contraction parameter representing an autonomic nervous system effect on smooth muscle contraction in a wall of one of said plurality of compartments; and
  solving, using the computer, one or more equations for said one or more time-dependent pressure functions and said logistic function to determine a circulatory system dynamic.

29. A method of modeling a circulatory system using a programmed computer, the method comprising:
  providing a circulatory system model in the computer, the model including one or more time-dependent pressure functions, each of said one or more time-dependent pressure functions representing a pressure in a portion of the circulatory system;
  using a logistic function in the computer to represent a regulatory mechanism parameter, said regulatory mechanism parameter representing a regulatory mechanism having an impact on circulatory system function, said using a logistic function including using a logistic function to represent an output versus pressure parameter, said output versus pressure parameter representing an effect of venous pressure on cardiac uptake according to the following logistic function:

$$OVP(P_V) = L_{inc}(P_V - \overline{P}_V, 0.5, 2.5, 0)$$

wherein OVP is said output versus pressure parameter, $P_V$ is said time-dependent pressure function for said venous compartment, $\overline{P}_V$ is the mean systemic venous pressure, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, $r > 0$, $-\infty < x < \infty$, and $\min < L_{inc}$;
  dividing the circulatory system into a plurality of compartments and a heart pump, said plurality of compartments representing a portion of the circulatory system, said heart pump interacting with at least one of said plurality of compartments, wherein said dividing step divides said circulatory system into a set of compartments comprising of an arterial compartment and a venous compartment, and a heart pump;
  assigning, using the computer, one of said one or more time-dependent pressure functions to each of said plurality of compartments;
  using a smooth muscle contraction parameter, said smooth muscle contraction parameter representing an autonomic nervous system effect on smooth muscle contraction in a wall of one of said plurality of compartments; and
  solving, using the computer, one or more equations for said one or more time-dependent pressure functions and said logistic function to determine a circulatory system dynamic.

30. A method of modeling a circulatory system using a programmed computer, the method comprising:
  providing a circulatory system model in the computer, the model including one or more time-dependent pressure functions, each of said one or more time-dependent pressure functions representing a pressure in a portion of the circulatory system;
  using a logistic function in the computer to represent a regulatory mechanism parameter, said regulatory mechanism parameter representing a regulatory mechanism having an impact on circulatory system function, wherein said regulatory mechanism parameter represents an autonomic nervous system effect on cardiac output according to the following equation:

$$ANSo = L_{dec}(P_A - \overline{P}_A, 0.1, 2, 0)$$

wherein $ANS_O$ is said regulatory mechanism parameter representing said autonomic nervous system effect on cardiac output, $P_A$ is said time-dependent pressure function for said arterial compartment, $\overline{P}_A$ is an initial mean arterial pressure, and $L_{dec}$ is a decreasing logistic function represented by the following equation:

$$L_{dec}(x, r, \max, \min) = \max + \frac{\min - \max}{1 + \frac{1 - \min}{\max - 1} e^{-rx}}$$

wherein max is a maximum value for x, min is a minimum value for x, r>0, −∞<x<∞, and $L_{dec}$<max;

dividing the circulatory system into a plurality of compartments and a heart pump, said plurality of compartments representing a portion of the circulatory system, said heart pump interacting with at least one of said plurality of compartments, wherein said dividing step divides said circulatory system into a set of compartments comprising of an arterial compartment and a venous compartment, and a heart pump;

assigning, using the computer, one of said one or more time-dependent pressure functions to each of said plurality of compartments;

using a smooth muscle contraction parameter, said smooth muscle contraction parameter representing an autonomic nervous system effect on smooth muscle contraction in a wall of one of said plurality of compartments; and solving, using the computer, one or more equations for said one or more time-dependent pressure functions and said logistic function to determine a circulatory system dynamic.

31. A method of modeling a circulatory system using a programmed computer, the method comprising:

providing a circulatory system model in the computer, the model including one or more time-dependent pressure functions, each of said one or more time-dependent pressure functions representing a pressure in a portion of the circulatory system;

using a logistic function in the computer to represent a regulatory mechanism parameter, said regulatory mechanism parameter representing a regulatory mechanism having an impact on circulatory system function, wherein said regulatory mechanism parameter represents an autonomic nervous system effect on non-cerebral blood flow according to the following equation:

$ANSz = L_{inc}(P_A - \overline{P}_A, 0.3, 1.1, 0.7)$ wherein ANSz is said regulatory mechanism parameter representing said autonomic nervous system effect on non-cerebral blood flow, $P_A$ is said time-dependent pressure function for said arterial compartment, $\overline{P}_A$ is an initial mean arterial pressure, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, r>0, −∞<x<∞, and min<$L_{inc}$;

dividing the circulatory system into a plurality of compartments and a heart pump, said plurality of compartments representing a portion of the circulatory system, said heart pump interacting with at least one of said plurality of compartments, wherein said dividing step divides said circulatory system into a set of compartments comprising of an arterial compartment and a venous compartment, and a heart pump;

assigning, using the computer, one of said one or more time-dependent pressure functions to each of said plurality of compartments;

using a smooth muscle contraction parameter, said smooth muscle contraction parameter representing an autonomic nervous system effect on smooth muscle contraction in a wall of one of said plurality of compartments; and solving, using the computer, one or more equations for said one or more time-dependent pressure functions and said logistic function to determine a circulatory system dynamic.

32. A method of modeling a circulatory system using a programmed computer, the method comprising:

providing a circulatory system model in the computer, the model including one or more time-dependent pressure functions, each of said one or more time-dependent pressure functions representing a pressure in a portion of the circulatory system;

using a logistic function in the computer to represent a regulatory mechanism parameter, said regulatory mechanism parameter representing a regulatory mechanism having an impact on circulatory system function, wherein said regulatory mechanism parameter represents a central nervous system effect on cardiac output according to the following equation:

$CNSo = L_{dec}(Q_1 - \overline{Q}_1, 0.01, 5, 0.9)$ wherein $Q_1$ is cerebral blood flow, $\overline{Q}_1$ is mean cerebral blood flow, and $L_{dec}$ is a decreasing logistic function represented by the following equation:

$$L_{dec}(x, r, \max, \min) = \max + \frac{\min - \max}{1 + \frac{1 - \min}{\max - 1} e^{-rx}}$$

wherein max is a maximum value for x, min is a minimum value for x, r>0, −∞<x<∞, and $L_{dec}$<max;

dividing the circulatory system into a plurality of compartments and a heart pump, said plurality of compartments representing a portion of the circulatory system, said heart pump interacting with at least one of said plurality of compartments, wherein said dividing step divides said circulatory system into a set of compartments comprising of an arterial compartment and a venous compartment, and a heart pump;

assigning, using the computer, one of said one or more time-dependent pressure functions to each of said plurality of compartments;

using a smooth muscle contraction parameter, said smooth muscle contraction parameter representing an autonomic nervous system effect on smooth muscle contraction in a wall of one of said plurality of compartments; and solving, using the computer, one or more equations for said one or more time-dependent pressure functions and said logistic function to determine a circulatory system dynamic.

33. A method of modeling a circulatory system using a programmed computer, the method comprising:

providing a circulatory system model in the computer, the model including one or more time-dependent pressure functions, each of said one or more time-dependent pressure functions representing a pressure in a portion of the circulatory system;

using a logistic function in the computer to represent a regulatory mechanism parameter, said regulatory mechanism parameter representing a regulatory mechanism having an impact on circulatory system function, wherein said regulatory mechanism parameter represents a central nervous system effects on non-cerebral blood flow according to the following equation:

$$CNSz = L_{inc}(Q_1 - \overline{Q}_1, 0.01, 1.01, 0.1)$$

wherein $Q_1$ is cerebral blood flow, $\overline{Q}_1$ is mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, r>0, $-\infty < x < \infty$, and $\min < L_{inc}$;

dividing the circulatory system into a plurality of compartments and a heart pump, said plurality of compartments representing a portion of the circulatory system, said heart pump interacting with at least one of said plurality of compartments, wherein said dividing step divides said circulatory system into a set of compartments comprising of an arterial compartment and a venous compartment, and a heart pump;

assigning, using the computer, one of said one or more time-dependent pressure functions to each of said plurality of compartments;

using a smooth muscle contraction parameter, said smooth muscle contraction parameter representing an autonomic nervous system effect on smooth muscle contraction in a wall of one of said plurality of compartments; and solving, using the computer, one or more equations for said one or more time-dependent pressure functions and said logistic function to determine a circulatory system dynamic.

34. A non-transitory computer readable medium containing computer executable instructions implementing a method of modeling a circulatory system, the instructions comprising:

a set of instructions for providing a circulatory system model including one or more time-dependent pressure functions, each of said one or more time-dependent pressure functions representing a pressure of a portion of the circulatory system;

a set of instructions for using a logistic function to represent a regulatory mechanism parameter, said regulatory mechanism parameter representing a regulatory mechanism having an impact on circulatory system function;

a set of instructions for using a logistic function to represent a cerebral blood flow parameter according to the following logistic function:

$$Q_1 = L_{inc}(P_{AV}, \overline{P}_{AV}, 0.15, 1.0001, 0) \cdot \overline{Q}_1$$

wherein $Q_1$ is said cerebral blood flow parameter, $P_{AV}$ is a pressure difference $P_A - P_V$, wherein $P_A$ is said time-dependent pressure function for said arterial compartment and $P_V$ is said time-dependent pressure function for said venous compartment, $\overline{P}_{AV}$ is a mean systemic indicative pressure, $\overline{Q}_1$ is a mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, r>0, $-\infty < x < \infty$, and $\min < L_{inc}$ a set of instructions for solving one or more equations for said one or more time-dependent pressure functions and said logistic function to determine a circulatory system dynamic;

a set of instructions for dividing the circulatory system into a plurality of compartments and a heart pump, said plurality of compartments representing a portion of the circulatory system, said heart pump interacting with at least one of said plurality of compartments, wherein the plurality of compartments includes an arterial compartment and a venous compartment;

a set of instructions for assigning a time-dependent pressure function to each of said plurality of compartments; and a set of instructions for using a smooth muscle contraction parameter, said smooth muscle contraction parameter representing an autonomic nervous system effect on smooth muscle contraction in a wall of one of said plurality of compartments.

35. A non-transitory computer readable medium containing computer executable instructions implementing a method of modeling a circulatory system, the instructions comprising:

a set of instructions for providing a circulatory system model including one or more time-dependent pressure functions, each of said one or more time-dependent pressure functions representing a pressure of a portion of the circulatory system;

a set of instructions for using a logistic function to represent a regulatory mechanism parameter, said regulatory mechanism parameter representing a regulatory mechanism having an impact on circulatory system function;

a set of instructions for using a logistic function to represent an output versus pressure parameter that represents an effect of venous pressure on cardiac uptake wherein the representing the output versus pressure parameter includes the following logistic function:

$$OVP(P_V) = L_{inc}(P_V - \overline{P}_V, 0.5, 2.5, 0)$$

wherein OVP is said output versus pressure parameter, $P_V$ is said time-dependent pressure function for said venous compartment, $\overline{P}_V$ is the mean systemic venous pressure, and $L_{inc}$ is an increasing logistic function represented by the following equation:

$$L_{inc}(x, r, \max, \min) = \max + \frac{\min - \max}{1 + \frac{1 - \min}{\max - 1} e^{rx}}$$

wherein max is a maximum value for x, min is a minimum value for x, r>0, $-\infty < x < \infty$, and $\min < L_{inc}$ a set of instructions for solving one or more equations for said one or more time-dependent pressure functions and said logistic function to determine a circulatory system dynamic;

a set of instructions for dividing the circulatory system into a plurality of compartments and a heart pump, said plurality of compartments representing a portion of the circulatory system, said heart pump interacting with at least one of said plurality of compartments, wherein the plurality of compartments includes an arterial compartment and a venous compartment;

a set of instructions for assigning a time-dependent pressure function to each of said plurality of compartments; and a set of instructions for using a smooth muscle contraction parameter, said smooth muscle contraction parameter representing an autonomic nervous system effect on smooth muscle contraction in a wall of one of said plurality of compartments.

36. A non-transitory computer readable medium containing computer executable instructions implementing a method of modeling a circulatory system, the instructions comprising:

a set of instructions for providing a circulatory system model including one or more time-dependent pressure functions, each of said one or more time-dependent pressure functions representing a pressure of a portion of the circulatory system;

a set of instructions for using a logistic function to represent a regulatory mechanism parameter, said regulatory mechanism parameter representing a regulatory mechanism having an impact on circulatory system function, said regulatory mechanism parameter representing an autonomic nervous system effect on cardiac output according to the following equation:

$$ANSo = L_{dec}(P_A - \overline{P}_A, 0.1, 2, 0)$$

wherein $ANS_o$ is said regulatory mechanism parameter representing said autonomic nervous system effect on cardiac output, $P_A$ is said time-dependent pressure function for said arterial compartment, $\overline{P}_A$ is an initial mean arterial pressure, and $L_{dec}$ is a decreasing logistic function represented by the following equation:

$$L_{dec}(x, r, \max, \min) = \max + \frac{\min - \max}{1 + \frac{1 - \min}{\max - 1}e^{-rx}}$$

wherein max is a maximum value for x, min is a minimum value for x, r>0, $-\infty < x < \infty$, and $L_{dec} < \max$;

a set of instructions for solving one or more equations for said one or more time-dependent pressure functions and said logistic function to determine a circulatory system dynamic;

a set of instructions for dividing the circulatory system into a plurality of compartments and a heart pump, said plurality of compartments representing a portion of the circulatory system, said heart pump interacting with at least one of said plurality of compartments, wherein the plurality of compartments includes an arterial compartment and a venous compartment;

a set of instructions for assigning a time-dependent pressure function to each of said plurality of compartments; and a set of instructions for using a smooth muscle contraction parameter, said smooth muscle contraction parameter representing an autonomic nervous system effect on smooth muscle contraction in a wall of one of said plurality of compartments.

37. A non-transitory computer readable medium containing computer executable instructions implementing a method of modeling a circulatory system, the instructions comprising:

a set of instructions for providing a circulatory system model including one or more time-dependent pressure functions, each of said one or more time-dependent pressure functions representing a pressure of a portion of the circulatory system;

a set of instructions for using a logistic function to represent a regulatory mechanism parameter, said regulatory mechanism parameter representing a regulatory mechanism having an impact on circulatory system function, said regulatory mechanism parameter representing an autonomic nervous system effect on non-cerebral blood flow according to the following equation:

$$ANSz = L_{inc}(P_A - \overline{P}_A, 0.3, 1.1, 0.7)$$

wherein ANSz is said regulatory mechanism parameter representing said autonomic nervous system effect on non-cerebral blood flow, $P_A$ is said time-dependent pressure function for said arterial compartment, $\overline{P}_A$ is an initial mean arterial pressure, and $L_{inc}$ is an increasing logistic function represented by the following equation:

$$L_{inc}(x, r, \max, \min) = \max + \frac{\min - \max}{1 + \frac{1 - \min}{\max - 1}e^{rx}}$$

wherein max is a maximum value for x, min is a minimum value for x, r>0, $-\infty < x < \infty$, and $\min < L_{inc}$.

a set of instructions for solving one or more equations for said one or more time-Dependent pressure functions and said logistic function to determine a circulatory system dynamic;

a set of instructions for dividing the circulatory system into a plurality of compartments and a heart pump, said plurality of compartments representing a portion of the circulatory system, said heart pump interacting with at least one of said plurality of compartments, wherein the plurality of compartments includes an arterial compartment and a venous compartment;

a set of instructions for assigning a time-dependent pressure function to each of said plurality of compartments; and a set of instructions for using a smooth muscle contraction parameter, said smooth muscle contraction parameter representing an autonomic nervous system effect on smooth muscle contraction in a wall of one of said plurality of compartments.

38. A non-transitory computer readable medium containing computer executable instructions implementing a method of modeling a circulatory system, the instructions comprising:

a set of instructions for providing a circulatory system model including one or more time-dependent pressure functions, each of said one or more time-dependent pressure functions representing a pressure of a portion of the circulatory system;

a set of instructions for using a logistic function to represent a regulatory mechanism parameter, said regulatory mechanism parameter representing a regulatory mechanism having an impact on circulatory system function, said regulatory mechanism parameter representing an a central nervous system effects on cardiac output according to the following equation:

$$CNSo = L_{dec}(Q_1 - \overline{Q}_1, 0.01, 5, 0.9)$$

wherein $Q_1$ is cerebral blood flow, $\overline{Q}_1$ is mean cerebral blood flow, and $L_{dec}$ is a decreasing logistic function represented by the following equation:

$$L_{dec}(x, r, \max, \min) = \max + \frac{\min - \max}{1 + \frac{1 - \min}{\max - 1}e^{-rx}}$$

wherein max is a maximum value for x, min is a minimum value for x, r>0, $-\infty < x < \infty$, and $L_{dec} < \max$;

a set of instructions for solving one or more equations for said one or more time-dependent pressure functions and said logistic function to determine a circulatory system dynamic;

a set of instructions for dividing the circulatory system into a plurality of compartments and a heart pump, said plurality of compartments representing a portion of the circulatory system, said heart pump interacting with at least one of said plurality of compartments, wherein the plurality of compartments includes an arterial compartment and a venous compartment;

a set of instructions for assigning a time-dependent pressure function to each of said plurality of compartments; and a set of instructions for using a smooth muscle contraction parameter, said smooth muscle contraction parameter representing an autonomic nervous system effect on smooth muscle contraction in a wall of one of said plurality of compartments.

39. A non-transitory computer readable medium containing computer executable instructions implementing a method of modeling a circulatory system, the instructions comprising:

a set of instructions for providing a circulatory system model including one or more time-dependent pressure functions, each of said one or more time-dependent pressure functions representing a pressure of a portion of the circulatory system;

a set of instructions for using a logistic function to represent a regulatory mechanism parameter, said regulatory mechanism parameter representing a regulatory mechanism having an impact on circulatory system function, said regulatory mechanism parameter representing an a central nervous system effects on non-cerebral blood flow according to the following equation:

$$CNSz = L_{inc}(Q_1 - \overline{Q}_1, 0.01, 1.01, 0.1)$$

wherein $Q_1$ is cerebral blood flow, $\overline{Q}_1$ is mean cerebral blood flow, and $L_{inc}$ is an increasing logistic function represented by the following equation:

$$L_{inc}(x, r, \max, \min) = \max + \frac{\min - \max}{1 + \frac{1 - \min}{\max - 1}e^{rx}}$$

wherein max is a maximum value for x, min is a minimum value for x, r>0, $-\infty < x < \infty$, and $\min < L_{inc}$;

a set of instructions for solving one or more equations for said one or more time-dependent pressure functions and said logistic function to determine a circulatory system dynamic;

a set of instructions for dividing the circulatory system into a plurality of compartments and a heart pump, said plurality of compartments representing a portion of the circulatory system, said heart pump interacting with at least one of said plurality of compartments, wherein the plurality of compartments includes an arterial compartment and a venous compartment;

a set of instructions for assigning a time-dependent pressure function to each of said plurality of compartments; and a set of instructions for using a smooth muscle contraction parameter, said smooth muscle contraction parameter representing an autonomic nervous system effect on smooth muscle contraction in a wall of one of said plurality of compartment.

* * * * *

UNITED STATES PATENT AND TRADEMARK OFFICE
CERTIFICATE OF CORRECTION

PATENT NO. : 7,794,230 B2
APPLICATION NO. : 11/387397
DATED : September 14, 2010
INVENTOR(S) : William D. Lakin et al.

It is certified that error appears in the above-identified patent and that said Letters Patent is hereby corrected as shown below:

In column 48, claim 10, line 39, after "r>0," delete "-∞<x<" and insert "-∞<x<∞" therefore;

In column 48, claim 12, line 58, after "circulatory" delete ",";

In column 49, claim 14, line 34, delete " $\dot{V} = C \cdot (\dot{P}(\dot{\phi} + \dot{P}^*))$ ," and insert -- $\dot{V} = C \cdot (\dot{P} - (\dot{\phi} + \dot{P}^*))$ -- therefore;

In column 51, claim 23, line 43, delete " $CNSz = L_{inc}(Q_1 \bar{Q}_1, 0.01, 1.01, .1)$ ," and insert -- $CNSz = L_{inc}(Q_1 - \bar{Q}_1, 0.01, 1.01, .1)$ -- therefore;

In column 52, claim 24, line 17, delete " $\dot{V} = C \cdot (P^{\cdot} - (\dot{\phi} = \dot{P}^*))$ ," and insert -- $\dot{V} = C \cdot (\dot{P} - (\dot{\phi} + \dot{P}^*))$ -- therefore;

In column 57, claim 34, line 58, delete " $Q_1 = L_{inc}(P_{AV} \bar{P}_{AV}, 0.15, 1.0001, 0) \cdot \bar{Q}_1$ " and insert -- $Q_1 = L_{inc}(P_{AV} - \bar{P}_{AV}, 0.15, 1.0001, 0) \cdot \bar{Q}_1$ -- therefore; and In column 60, claim 37, line 34, after "and min<L_{inc}" insert ";"

In column 60, claim 37, line 36, delete "time-Dependent" and insert "time-dependent" therefore.

Signed and Sealed this
Fifth Day of July, 2011

David J. Kappos
*Director of the United States Patent and Trademark Office*